US006514700B1

(12) United States Patent
Singh

(10) Patent No.: US 6,514,700 B1
(45) Date of Patent: *Feb. 4, 2003

(54) NUCLEIC ACID DETECTION USING DEGRADATION OF A TAGGED SEQUENCE

(75) Inventor: Sharat Singh, San Jose, CA (US)

(73) Assignee: ACLARA BioSciences, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/602,586

(22) Filed: Jun. 21, 2000

Related U.S. Application Data

(63) Continuation-in-part of application No. 09/561,579, filed on Apr. 28, 2000, now abandoned, which is a continuation-in-part of application No. 09/303,029, filed on Apr. 30, 1999, now Pat. No. 6,322,980.

(51) Int. Cl.$^7$ .................................................. C12Q 1/68
(52) U.S. Cl. ......................................................... 435/6
(58) Field of Search ..................... 435/6, 91.2; 536/22.1

(56) References Cited

U.S. PATENT DOCUMENTS

| | | |
|---|---|---|
| 4,274,240 A | 6/1981 | Soum |
| 4,675,300 A | 6/1987 | Zare et al. |
| 5,324,401 A | 6/1994 | Yeung et al. |
| 5,470,705 A | 11/1995 | Grossman et al. |
| 5,552,028 A | 9/1996 | Madabhushi et al. |
| 5,560,811 A | 10/1996 | Briggs et al. |
| 5,565,324 A | 10/1996 | Still et al. |
| 5,567,292 A | 10/1996 | Madabhushi et al. |
| 5,580,732 A | 12/1996 | Grossman et al. |
| 5,624,800 A | 4/1997 | Grossman et al. |
| 5,703,222 A | 12/1997 | Grossman et al. |
| 5,721,099 A | 2/1998 | Still et al. |
| 5,807,682 A | 9/1998 | Grossman et al. |
| 5,874,213 A | 2/1999 | Cummins et al. |
| 5,916,426 A | 6/1999 | Madabhushi et al. |
| 5,989,871 A | 11/1999 | Grossman et al. |
| 6,045,676 A | 4/2000 | Mathies et al. |

FOREIGN PATENT DOCUMENTS

| | | |
|---|---|---|
| WO | WO 00/55368 | 9/2000 |

OTHER PUBLICATIONS

Brenner et al., "Encoded Combinatorial Chemistry", *Proc. Natl. Acad. Sci. USA* 89:5381–5383, 1992.

Ross et al., "Discrimination of Single–Nucleotide Polymorphisms in Human DNA Using Peptide Nucleic Acid Probes Detected by MALDI–TOF Mass Spectrometry", *Anal. Chem.* 69:4197–4202, 1997.

Still, W.C., "Discovery of Sequence–Selective Peptide Binding by Sunthetic Receptors Using Encoded Combinatorial Libraries", *Accounts of Chem. Res.* 29:155–163, 1996.

Wang et al., "Large–Scale Identification, Mapping, Genotyping of Single–Nucleotide Polymorphisms in the Human Genome", *Science* 280(5366):1077–1082, 1997.

Woolley et al., "Functional Integration of PCR Amplification and Capillary Electrophoresis in a Microfabricated DNA Analysis Device", *Anal. Chem.* 68:4081–4086, 1996.

Hacia, *Nat. Genet.* (1996), 14:441–47.

Haff, *Nucleic Acids Res.* (1997), 25:3749–50.

Holland, *Proc. Natl. Acad. Sci. USA* (1991), 88:7276–80.

Houghten, et al., *Int. J. Pep. Prot. Res.* (1980), 16:311–20.

Lee, *Nucleic Acid Research* (1993), 21:16 3761–66.

Marglin, et al., *Ann. Rev. Biochem.* (1970), 39:841–66.

Marino, *Electrophoresis* (1996), 17:1499–04.

Matthews, et al., *Anal. Biochem.* (1988), 169:1–25.

Merrifield, *J. Am. Chem. Soc.* (1980), 85:2149–54.

Pastinen, *Clin. Chem.* (1996), 42:1391–97.

Wetmur, *Critical Rev. in Biochem. And Molecular Biol.* (1991), 26:277–59.

White, *Trends Biotechnology* (1996), 14(12):478–83.

*Primary Examiner*—Gary Benzion
*Assistant Examiner*—Joyce Tung
(74) *Attorney, Agent, or Firm*—Jacqueline F. Mahoney; Peter J. Dehlinger; Perkins Coie LLP

(57) ABSTRACT

Methods and compositions are provided for detecting target molecules, e.g. DNA sequences, particularly single nucleotide polymorphisms, using a pair of nucleotide sequences, a primer and a snp detection sequence, where the snp detection sequence binds downstream from the primer to the target DNA in the direction of primer extension, or ligands and receptors. The methods employ e-tags comprising a mobility-identifying region joined to a detectable label and a target-binding region. The result of the binding of the target-binding region to the target is to have a bond cleaved in the starting material with the production of a detectable product with a different mobility from the starting material, where the different e-tags can be separated and detected.

7 Claims, 14 Drawing Sheets

CCA GCA ACC AAT GAT GCC CGT T-TAMARA-3'
CA GCA ACC ATT GAT GCC CGT T-TAMARA-3'

CCA GCA AGC ACT GAT GCC TGT T-TAMARA-3'
CA GCA AGC ACT GAT GCC TGT T-TAMARA-3'

Fig. 1B

| | Absorbance Maxima | Emission Maxima |
|---|---|---|
| Fluorescein | 494 nm | 525 nm |
| Tetrtachloro Fluorescein | 521 nm | 536 nm |
| TAMRA | 565 nm | 580 nm |

Fig. 1C

SEQUENCE LISTING

```
<160> NUMBER OF SEQ ID NOS: 56

<210> SEQ ID NO 1
<211> LENGTH: 16
<212> TYPE: DNA
<213> ORGANISM: Artificial Sequence
<220> FEATURE:
<223> OTHER INFORMATION: primer

<400> SEQUENCE: 1
tcaccacatc ccagtg                                                   16

<210> SEQ ID NO 2
<211> LENGTH: 16
<212> TYPE: DNA
<213> ORGANISM: Artificial Sequence
<220> FEATURE:
<223> OTHER INFORMATION: primer

<400> SEQUENCE: 2
gagggaggtt tggctg                                                   16

<210> SEQ ID NO 3
<211> LENGTH: 22
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)...(1)
<223> OTHER INFORMATION: 5' nucleotide linked to tetrachlorofluorescein
<220> FEATURE:
<221> NAME/KEY: misc_feature
<222> LOCATION: (22)...(22)
<223> OTHER INFORMATION: 3' nucleotide linked to tetramethyl rhodamine

<400> SEQUENCE: 3
ccagcaacca atgatgcccg tt                                            22

<210> SEQ ID NO 4
<211> LENGTH: 22
<212> TYPE: DNA
<213> ORGANISM: Artificial Sequence
<220> FEATURE:
<223> OTHER INFORMATION: probe
<220> FEATURE:
<221> NAME/KEY: misc_binding
<222> LOCATION: (1)...(1)
<223> OTHER INFORMATION: 5' nucleotide linked to fluorescein
```

```
<220> FEATURE:
<221> NAME/KEY: misc_binding
<222> LOCATION: (22)...(22)
<223> OTHER INFORMATION: 3' nucleotide linked to tetramethyl rhodamine

<400> SEQUENCE: 4
ccagcaagca ctgatgcctg tt                                               22

<210> SEQ ID NO 5
<211> LENGTH: 4
<212> TYPE: PRT
<213> ORGANISM: Artificial Sequence
<220> FEATURE:
<223> OTHER INFORMATION: peptide linker

<400> SEQUENCE: 5

Lys Lys Ala Ala
 1

<210> SEQ ID NO 6
<211> LENGTH: 4
<212> TYPE: PRT
<213> ORGANISM: Artificial Sequence
<220> FEATURE:
<223> OTHER INFORMATION: peptide linker

<400> SEQUENCE: 6

Lys Lys Lys Ala
 1

<210> SEQ ID NO 7
<211> LENGTH: 4
<212> TYPE: PRT
<213> ORGANISM: Artificial Sequence
<220> FEATURE:
<223> OTHER INFORMATION: peptide linker

<400> SEQUENCE: 7

Lys Lys Lys Lys
 1

<210> SEQ ID NO 8
<211> LENGTH: 26
<212> TYPE: DNA
<213> ORGANISM: Artificial Sequence
<220> FEATURE:
<223> OTHER INFORMATION: probe

<400> SEQUENCE: 8
gtggaggtca acgagcaaga atttct                                           26

<210> SEQ ID NO 9
<211> LENGTH: 25
<212> TYPE: DNA
<213> ORGANISM: Artificial Sequence
<220> FEATURE:
<223> OTHER INFORMATION: probe

<400> SEQUENCE: 9
agatgcgatc tgtgagccga gtctt                                            25

<210> SEQ ID NO 10
<211> LENGTH: 32
<212> TYPE: DNA
<213> ORGANISM: Artificial Sequence
<220> FEATURE:
<223> OTHER INFORMATION: probe
```

<400> SEQUENCE: 10
ttctggagat ttatgttcta tggaatcttt tt                          32

<210> SEQ ID NO 11
<211> LENGTH: 21
<212> TYPE: DNA
<213> ORGANISM: Artificial Sequence
<220> FEATURE:
<223> OTHER INFORMATION: probe

<400> SEQUENCE: 11
aaggaggaac gctctatcgc g                                      21

<210> SEQ ID NO 12
<211> LENGTH: 20
<212> TYPE: DNA
<213> ORGANISM: Artificial Sequence
<220> FEATURE:
<223> OTHER INFORMATION: probe

<400> SEQUENCE: 12
attgttctgc gcatggcggt                                        20

<210> SEQ ID NO 13
<211> LENGTH: 25
<212> TYPE: DNA
<213> ORGANISM: Artificial Sequence
<220> FEATURE:
<223> OTHER INFORMATION: probe

<400> SEQUENCE: 13
atacagaagc gtcatcaaag catgc                                  25

<210> SEQ ID NO 14
<211> LENGTH: 29
<212> TYPE: DNA
<213> ORGANISM: Artificial Sequence
<220> FEATURE:
<223> OTHER INFORMATION: probe

<400> SEQUENCE: 14
caatatagtt cttggagaag gtggaatca                              29

<210> SEQ ID NO 15
<211> LENGTH: 26
<212> TYPE: DNA
<213> ORGANISM: Artificial Sequence
<220> FEATURE:
<223> OTHER INFORMATION: probe

<400> SEQUENCE: 15
ctgagtggag gtcaacgagc aagaat                                 26

<210> SEQ ID NO 16
<211> LENGTH: 32
<212> TYPE: DNA
<213> ORGANISM: Artificial Sequence
<220> FEATURE:
<223> OTHER INFORMATION: probe

<400> SEQUENCE: 16
ttccattttc tttttagagc agtatacaaa ga                          32

<210> SEQ ID NO 17

<211> LENGTH: 28
<212> TYPE: DNA
<213> ORGANISM: Artificial Sequence
<220> FEATURE:
<223> OTHER INFORMATION: probe

<400> SEQUENCE: 17
aaactccagc atagatgtgg atagcttg                               28

<210> SEQ ID NO 18
<211> LENGTH: 23
<212> TYPE: DNA
<213> ORGANISM: Artificial Sequence
<220> FEATURE:
<223> OTHER INFORMATION: probe

<400> SEQUENCE: 18
ctaagccatg gccacaagca gtt                                    23

<210> SEQ ID NO 19
<211> LENGTH: 25
<212> TYPE: DNA
<213> ORGANISM: Artificial Sequence
<220> FEATURE:
<223> OTHER INFORMATION: probe

<400> SEQUENCE: 19
cctttcaaat tcagattgag catac                                  25

<210> SEQ ID NO 20
<211> LENGTH: 23
<212> TYPE: DNA
<213> ORGANISM: Artificial Sequence
<220> FEATURE:
<223> OTHER INFORMATION: probe

<400> SEQUENCE: 20
tgtgaaattg tctgccattc tta                                    23

<210> SEQ ID NO 21
<211> LENGTH: 23
<212> TYPE: DNA
<213> ORGANISM: Artificial Sequence
<220> FEATURE:
<223> OTHER INFORMATION: probe

<400> SEQUENCE: 21
tcttttgcag agaatgggat aga                                    23

<210> SEQ ID NO 22
<211> LENGTH: 23
<212> TYPE: DNA
<213> ORGANISM: Artificial Sequence
<220> FEATURE:
<223> OTHER INFORMATION: probe

<400> SEQUENCE: 22
ccaaagcagt acagcctctc tta                                    23

<210> SEQ ID NO 23
<211> LENGTH: 22
<212> TYPE: DNA
<213> ORGANISM: Artificial Sequence
<220> FEATURE:
<223> OTHER INFORMATION: probe

<400> SEQUENCE: 23

```
tctgtgcttc cctatgcact aa                                          22

<210> SEQ ID NO 24
<211> LENGTH: 20
<212> TYPE: DNA
<213> ORGANISM: Artificial Sequence
<220> FEATURE:
<223> OTHER INFORMATION: probe

<400> SEQUENCE: 24
tggagccttc agagggtaaa                                             20

<210> SEQ ID NO 25
<211> LENGTH: 25
<212> TYPE: DNA
<213> ORGANISM: Artificial Sequence
<220> FEATURE:
<223> OTHER INFORMATION: probe

<400> SEQUENCE: 25
cctttcaaat tcagattgag catac                                       25

<210> SEQ ID NO 26
<211> LENGTH: 25
<212> TYPE: DNA
<213> ORGANISM: Artificial Sequence
<220> FEATURE:
<223> OTHER INFORMATION: probe

<400> SEQUENCE: 26
cctttcaaat tcagattgag catac                                       25

<210> SEQ ID NO 27
<211> LENGTH: 25
<212> TYPE: DNA
<213> ORGANISM: Artificial Sequence
<220> FEATURE:
<223> OTHER INFORMATION: probe

<400> SEQUENCE: 27
gaccaggaaa tagagaggaa atgta                                       25

<210> SEQ ID NO 28
<211> LENGTH: 27
<212> TYPE: DNA
<213> ORGANISM: Artificial Sequence
<220> FEATURE:
<223> OTHER INFORMATION: probe

<400> SEQUENCE: 28
gaaggagaag gaagagttgg tattatc                                     27

<210> SEQ ID NO 29
<211> LENGTH: 21
<212> TYPE: DNA
<213> ORGANISM: Artificial Sequence
<220> FEATURE:
<223> OTHER INFORMATION: probe

<400> SEQUENCE: 29
ttgggctcag atctgtgata g                                           21

<210> SEQ ID NO 30
<211> LENGTH: 26
<212> TYPE: DNA
```

-continued

```
<213> ORGANISM: Artificial Sequence
<220> FEATURE:
<223> OTHER INFORMATION: probe antisense

<400> SEQUENCE: 30
agaaattctt gctcgttgac ctccac                                              26

<210> SEQ ID NO 31
<211> LENGTH: 25
<212> TYPE: DNA
<213> ORGANISM: Artificial Sequence
<220> FEATURE:
<223> OTHER INFORMATION: probe antisense

<400> SEQUENCE: 31
aagactcggc tcacagatcg catct                                               25

<210> SEQ ID NO 32
<211> LENGTH: 32
<212> TYPE: DNA
<213> ORGANISM: Artificial Sequence
<220> FEATURE:
<223> OTHER INFORMATION: probe antisense

<400> SEQUENCE: 32
aaaaagattc catagaacat aaatctccag aa                                       32

<210> SEQ ID NO 33
<211> LENGTH: 21
<212> TYPE: DNA
<213> ORGANISM: Artificial Sequence
<220> FEATURE:
<223> OTHER INFORMATION: probe antisense

<400> SEQUENCE: 33
cgcgatagag cgttcctcct t                                                   21

<210> SEQ ID NO 34
<211> LENGTH: 20
<212> TYPE: DNA
<213> ORGANISM: Artificial Sequence
<220> FEATURE:
<223> OTHER INFORMATION: probe antisense

<400> SEQUENCE: 34
accgccatgc gcagaacaat                                                     20

<210> SEQ ID NO 35
<211> LENGTH: 25
<212> TYPE: DNA
<213> ORGANISM: Artificial Sequence
<220> FEATURE:
<223> OTHER INFORMATION: probe antisense

<400> SEQUENCE: 35
gcatgctttg atgacgcttc tgtat                                               25

<210> SEQ ID NO 36
<211> LENGTH: 29
<212> TYPE: DNA
<213> ORGANISM: Artificial Sequence
<220> FEATURE:
<223> OTHER INFORMATION: probe antisense

<400> SEQUENCE: 36
tgattccacc ttctccaaga actatattg                                           29
```

<210> SEQ ID NO 37
<211> LENGTH: 26
<212> TYPE: DNA
<213> ORGANISM: Artificial Sequence
<220> FEATURE:
<223> OTHER INFORMATION: probe antisense

<400> SEQUENCE: 37
attcttgctc gttgacctcc actcag                                              26

<210> SEQ ID NO 38
<211> LENGTH: 32
<212> TYPE: DNA
<213> ORGANISM: Artificial Sequence
<220> FEATURE:
<223> OTHER INFORMATION: probe antisense

<400> SEQUENCE: 38
tctttgtata ctgctctaaa aagaaaatgg aa                                       32

<210> SEQ ID NO 39
<211> LENGTH: 28
<212> TYPE: DNA
<213> ORGANISM: Artificial Sequence
<220> FEATURE:
<223> OTHER INFORMATION: probe antisense

<400> SEQUENCE: 39
caagctatcc acatctatgc tggagttt                                            28

<210> SEQ ID NO 40
<211> LENGTH: 23
<212> TYPE: DNA
<213> ORGANISM: Artificial Sequence
<220> FEATURE:
<223> OTHER INFORMATION: probe antisense

<400> SEQUENCE: 40
aactgcttgt ggccatggct tag                                                 23

<210> SEQ ID NO 41
<211> LENGTH: 23
<212> TYPE: DNA
<213> ORGANISM: Artificial Sequence
<220> FEATURE:
<223> OTHER INFORMATION: probe

<400> SEQUENCE: 41
tttacagcaa atgcttgcta gac                                                 23

<210> SEQ ID NO 42
<211> LENGTH: 24
<212> TYPE: DNA
<213> ORGANISM: Artificial Sequence
<220> FEATURE:
<223> OTHER INFORMATION: probe

<400> SEQUENCE: 42
ggtttggttg acttggtagg ttta                                                24

<210> SEQ ID NO 43
<211> LENGTH: 25
<212> TYPE: DNA
<213> ORGANISM: Artificial Sequence
<220> FEATURE:

<223> OTHER INFORMATION: probe

<400> SEQUENCE: 43
tggagttgga ttcatccttt atatt                                           25

<210> SEQ ID NO 44
<211> LENGTH: 20
<212> TYPE: DNA
<213> ORGANISM: Artificial Sequence
<220> FEATURE:
<223> OTHER INFORMATION: probe

<400> SEQUENCE: 44
ccaaaaatgg ctgggtgtag                                                 20

<210> SEQ ID NO 45
<211> LENGTH: 25
<212> TYPE: DNA
<213> ORGANISM: Artificial Sequence
<220> FEATURE:
<223> OTHER INFORMATION: probe

<400> SEQUENCE: 45
ccaagagagt cataccatgt ttgta                                           25

<210> SEQ ID NO 46
<211> LENGTH: 21
<212> TYPE: DNA
<213> ORGANISM: Artificial Sequence
<220> FEATURE:
<223> OTHER INFORMATION: probe

<400> SEQUENCE: 46
tgctttgatg acgcttctgt a                                               21

<210> SEQ ID NO 47
<211> LENGTH: 23
<212> TYPE: DNA
<213> ORGANISM: Artificial Sequence
<220> FEATURE:
<223> OTHER INFORMATION: probe

<400> SEQUENCE: 47
tttacagcaa atgcttgcta gac                                             23

<210> SEQ ID NO 48
<211> LENGTH: 23
<212> TYPE: DNA
<213> ORGANISM: Artificial Sequence
<220> FEATURE:
<223> OTHER INFORMATION: probe

<400> SEQUENCE: 48
tttacagcaa atgcttgcta gac                                             23

<210> SEQ ID NO 49
<211> LENGTH: 27
<212> TYPE: DNA
<213> ORGANISM: Artificial Sequence
<220> FEATURE:
<223> OTHER INFORMATION: probe

<400> SEQUENCE: 49
catctaggta tccaaaagga gagtcta                                         27

```
<210> SEQ ID NO 50
<211> LENGTH: 27
<212> TYPE: DNA
<213> ORGANISM: Artificial Sequence
<220> FEATURE:
<223> OTHER INFORMATION: probe

<400> SEQUENCE: 50
cggtatatag ttcttcctca tgctatt                                         27

<210> SEQ ID NO 51
<211> LENGTH: 20
<212> TYPE: DNA
<213> ORGANISM: Artificial Sequence
<220> FEATURE:
<223> OTHER INFORMATION: probe

<400> SEQUENCE: 51
gcaagatctt cgccttactg                                                 20

<210> SEQ ID NO 52
<211> LENGTH: 21
<212> TYPE: DNA
<213> ORGANISM: Artificial Sequence
<220> FEATURE:
<223> OTHER INFORMATION: snp detection sequence
<220> FEATURE:
<221> NAME/KEY: misc_feature
<222> LOCATION: (21)...(21)
<223> OTHER INFORMATION: 3' nucleotide linked to tetramethyl rhodamine

<400> SEQUENCE: 52
cagcaaccat tgatgcccgt t                                               21

<210> SEQ ID NO 53
<211> LENGTH: 21
<212> TYPE: DNA
<213> ORGANISM: Artificial Sequence
<220> FEATURE:
<223> OTHER INFORMATION: snp detection sequence
<220> FEATURE:
<221> NAME/KEY: misc_feature
<222> LOCATION: (21)...(21)
<223> OTHER INFORMATION: 3' nucleotide linked to tetramethyl rhodamine

<400> SEQUENCE: 53
cagcaagcac tgatgcctgt t                                               21

<210> SEQ ID NO 54
<211> LENGTH: 4
<212> TYPE: PRT
<213> ORGANISM: Artificial Sequence
<220> FEATURE:
<223> OTHER INFORMATION: peptide linker
<220> FEATURE:
<221> NAME/KEY: misc_feature
<222> LOCATION: (1)...(1)
<223> OTHER INFORMATION: 5' nucleotide reacted with fluorescein
      N-hydroxysuccinimide

<400> SEQUENCE: 54

Lys Lys Ala Ala
 1

<210> SEQ ID NO 55
<211> LENGTH: 4
<212> TYPE: PRT
<213> ORGANISM: Artificial Sequence
<220> FEATURE:
```

```
-continued

<223> OTHER INFORMATION: peptide linker
<220> FEATURE:
<221> NAME/KEY: misc_feature
<222> LOCATION: (1)...(1)
<223> OTHER INFORMATION: 5' nucleotide reacted with fluorescein
      N-hydroxysuccinimide

<400> SEQUENCE: 55

Lys Lys Lys Ala
 1

<210> SEQ ID NO 56
<211> LENGTH: 4
<212> TYPE: PRT
<213> ORGANISM: Artificial Sequence
<220> FEATURE:
<223> OTHER INFORMATION: peptide linker
<220> FEATURE:
<221> NAME/KEY: misc_feature
<222> LOCATION: (1)...(1)
<223> OTHER INFORMATION: 5' nucleotide reacted with fluorescein
      N-hydroxysuccinimide

<400> SEQUENCE: 56

Lys Lys Lys Lys
 1
```

NUCLEIC ACID DETECTION USING DEGRADATION OF A TAGGED SEQUENCE

CROSS-REFERENCE TO RELATED APPLICATIONS

This application is a continuation-in-part of application Ser. No. 09/561,579, filed Apr. 28, 2000 now abandoned, which is a continuation-in-part of application Ser. No. 09/303,029, filed Apr. 30, 1999, now U.S. Pat. No. 6,322,980 which disclosure is incorporated herein by reference.

INTRODUCTION

FIELD OF THE INVENTION

The field of this invention is electrophoretically separable compositions for use in multiplex detection.

BACKGROUND OF THE INVENTION

As the human genome is elucidated, there will be numerous opportunities for performing assays to determine the presence of specific sequences, distinguishing between alleles in homozygotes and heterozygotes, determining the presence of mutations, evaluating cellular expression patterns, etc. In many of these cases one will wish to determine in a single reaction, a number of different characteristics of the same sample. Also, there will be an interest in determining the presence of one or more pathogens, their antibiotic resistance genes, genetic subtype and the like.

In many assays, there will be an interest in determining the presence of specific sequences, whether genomic, synthetic or cDNA. These sequences may be associated particularly with genes, regulatory sequences, repeats, multimeric regions, expression patterns, and the like There is and will continue to be comparisons of the sequences of different individuals. It is believed that there will be about one polymorphism per 1,000 bases, so that one may anticipate that there will be an extensive number of differences between individuals. By single nucleotide polymorphism (snp's) is intended that there will be a prevalent nucleotide at the site, with one or more of the remaining bases being present in substantially smaller percent of the population.

For the most part, the snp's will be in non-coding regions, primarily between genes, but will also be present in exons and introns. In addition, the great proportion of the snp's will not affect the phenotype of the individual, but will clearly affect the genotype. The snp's have a number of properties of interest. Since the snp's will be inherited, individual snp's and/or snp patterns may be related to genetic defects, such as delections, insertions and mutations involving one or more bases in genes. Rather than isolating and sequencing the target gene, it will be sufficient to identify the snp's involved.

In addition, the snp's may be used in forensic medicine to identify individuals. While other genetic markers are available, the large number of snp's and their extensive distribution in the chromosomes, make the snp's an attractive target. Also, by determining a plurality of snp's associated with a specific phenotype, one may use the snp pattern as an indication of the phenotype, rather than requiring a determination of the genes associated with the phenotype.

The need to determine many analytes or nucleic acid sequences (for example multiple pathogens or multiple genes or multiple genetic variants) in blood or other biological fluids has become increasingly apparent in many branches of medicine. The need to study differential expression of multiple genes to determine toxicologically-relevant outcomes or the need to screen transfused blood for viral contaminants with high sensitivity is clearly evident. Thus most multi-analyte assays or assays which detect multiple nucleic acid sequences involve mutiple steps, have poor sensitivity and poor dynamic range (2 to 100-fold differences in concentration of the analytes is determined) and some require sophisticated instrumentation.

Some of the known classical methods for multianalyte assays include the following:
  a. The use of two different radioisotope labels to distinguish two different analytes.
  b. The use of two or more different fluorescent labels to distinguish two or more analytes.
  c. The use of lanthanide chelates where both lifetime and wavelength are used to distinguish two or more analytes.
  d. The use of fluorescent and chemiluminescent labels to distinguish two or more analytes.
  e. The use of two different enzymes to distinguish two or more analytes.
  f. The use of enzyme and acridinium esters to distinguish two or more analytes.
  g. Spatial resolution of different analytes, for example, on arrays to identify and quantify multiple analytes.
  h. The use of acridinium ester labels where lifetime or dioxetanone formation is used to quantify two different viral targets.

Thus an assay that has higher sensitivity, large dynamic range ($10^3$ to $10^4$-fold differences in target nucleic acids levels), greater degree of multiplexing, and fewer and more stable reagents would increase the simplicity and reliability of multianalyte assays.

The need to identify and quantify a large number of bases or sequences potentially distributed over centimorgans of DNA offers a major challenge. Any method should be accurate, reasonably economical in limiting the amount of reagents required and providing for a single assay, which allows for differentiation of the different snp's or differentiation and quantitation of multiple genes.

Finally, while nucleic acid sequences provide extreme diversity for situations that may be of biological or other interest, there are other types of compounds, such as proteins in proteomics that may also offer opportunities for multiplexed determinations.

BRIEF DESCRIPTION OF THE RELATED ART

Holland (*Proc. Natl. Acad. Sci. USA* (1991) 88:7276) discloses that the exonuclease activity of the thermostable enzyme Thermus aquaticus DNA polymerase in PCR amplification to generate specific detectable signal concomitantly with amplification.

The TaqMan assay is discussed by Lee in *Nucleic Acid Research* (1993) 21:16 3761).

White (Trends Biotechnology (1996) 14(12):478–483) discusses the problems of multiplexing in the Taqman assay.

Marino, *Electrophoresis* (1996) 17:1499 describes low-stringency-sequence specific PCR (LSSP-PCR). A PCR amplified sequence is subjected to single primer amplification under conditions of low stringency to produce a range of different length amplicons. Different patterns are obtained when there are differences in sequence. The patterns are unique to an individual and of possible value for identity testing.

Single strand conformational polymorphism (SSCP) yields similar results. In this method the PCR amplified DNA is denatured and sequence dependent conformations of the single strands are detected by their differing rates of migration during gel electrophoresis. As with LSSP-PCR above, different patterns are obtained that signal differences in sequence. However, neither LSSP-PCR nor SSCP gives specific sequence information and both depend on the questionable assumption that any base that is changed in a sequence will give rise to a conformational change that can be detected.

Pastinen, *Clin. Chem.* (1996) 42:1391 amplifies the target DNA and immobilizes the amplicons. Multiple primers are then allowed to hybridize to sites 3' and contiguous to an SNP site of interest. Each primer has a different size that serves as a code. The hybridized primers are extended by one base using a fluorescently labeled dideoxynucleoside triphosphate. The size of each of the fluorescent products that is produced, determined by gel electrophoresis, indicates the sequence and, thus, the location of the SNP. The identity of the base at the SNP site is defined by the triphosphate that is used. A similar approach is taken by Haff, *Nucleic Acids Res.* (1997) 25:3749 except that the sizing is carried out by mass spectroscopy and thus avoids the need for a label. However, both methods have the serious limitation that screening for a large number of sites will require large, very pure primers that can have troublesome secondary structures and be very expensive to synthesize.

Hacia, *Nat. Genet.* (1996) 14:441 uses a high density array of oligonucleotides. Labeled DNA samples were allowed to bind to 96,600 20-base oligonucleotides and the binding patterns produced from different individuals were compared. The method is attractive in that SNP's can be directly identified, but the cost of the arrays is high and non-specific hybridization may confound the accuracy of the genetic information.

Fan (Oct. 6–8, 1997, IBC, Annapolis Md.) has reported results of a large scale screening of human sequence-tagged sites. The accuracy of single nucleotide polymorphism screening was determined by conventional ABI resequencing.

Allele specific oligonucleotide hybridization along with mass spectroscopy has been discussed by Ross in *Anal. Chem.* (1997) 69:4197.

Holland, et al., PNAS USA (1991) 88, 7276–7280, describes use of DNA polymerase 5'-3' exonuclease activity for detection of PCR products. U.S. Pat. No. 5,807,682 describes probe compositions for detecting a plurality of nucleic acid targets.

SUMMARY OF THE INVENTION

Systems are provided comprising libraries of compositions for linking to or linked to assay reagents for performing simultaneous determinations in a single container. The systems combine entities that comprise e-tags (electrophoretic tags capable of being separated electrophoretically with the entities to which they are attached in a specific determination) that include mobility-identifying regions comprising a first functionality bonded to an assay reagent and a second functionality bonded to or for bonding to a detectable label, with a sample under conditions which produce an analyte-dependent detectable change in the mobility of the entities, means for moving the modified entities to an electrophoretic device, and a data processor for processing the data from the electrophoretic device. Libraries are employed comprising a plurality of e-tag containing compositions, where the e-tags are joined to assay reagents, a unit of an assay reagent or provide a functionality for linking to an assay reagent, where the linkage may be cleavable. The assays employ reagents for homogeneous (no required separation step) or heterogeneous (a separation step required) protocols.

The libraries comprise entities comprising electrophoretic tags that are small molecules (molecular weight of 150 to 5,000), usually other than oligomers; which can be used in any measurement technique that permits identification by mass, e.g. mass spectrometry, and or mass/charge ratio, as in mobility in electrophoresis. Simple variations in mass and/or mobility of the e-tag leads to generation of a library of e-tags, that can then be used to detect a plurality of individual events associated with different molecular species, generally related species. The e-tags are designed to be easily and rapidly separated, particularly in free solution without the need for a polymeric separation media. Quantitation is achieved using internal controls. Enhanced separation of the e-tags comprising a nucleotide in electrophoresis is achieved by modifying the tags with positively charged moieties.

DESCRIPTION OF THE SPECIFIC EMBODIMENTS

Figure 1A:
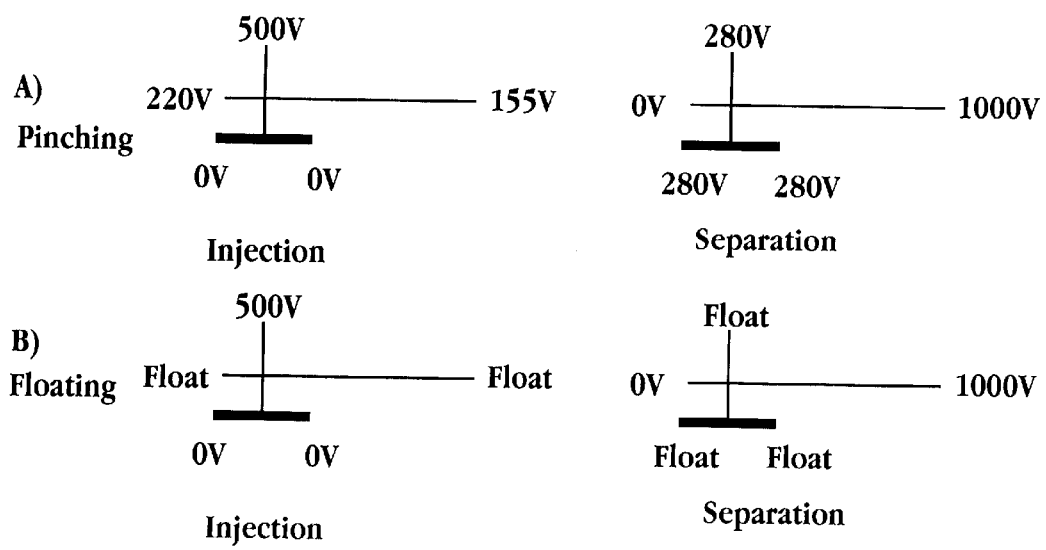
FIG. 1 depicts a high-voltage configuration for a $CE^2$ LabCard assay.
FIGS. 1B–1D depict the specific sequences of the snp detection sequences for the two alleles, the optical characteristics of the fluorescent dyes, and the cleaved fragments from the snp detection sequences, respectively.
Figure 1D:
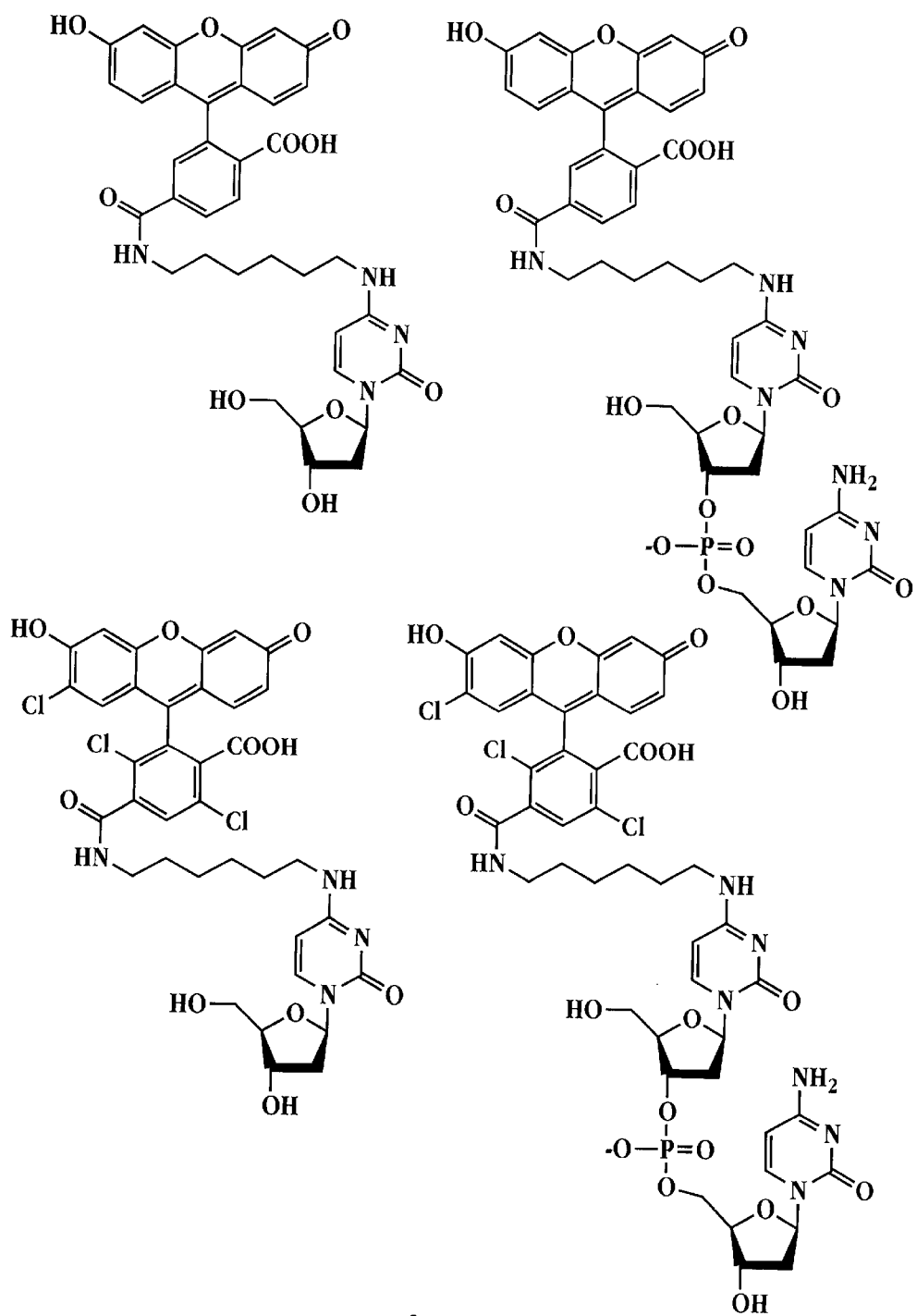

A system is provided for the simultaneous multiplexed determination of a plurality of events employing electrophoresis to distinguish the events, comprising an electrophoretic device for electrophoretic separation and detection, a container containing a first set of first agents, referred to as "e-tags," comprising differing mobility regions and a second reagent composition comprising at least one active second agent, under conditions where said second agent modifies at least one member of said first agent set resulting in a change of electrophoretic mobility of said at least one member to provide a modified member retaining said mobility region, and transfer of said at least one modified member to said electrophoretic device for separation and detection of said at least one modified member. The electrophoretic device may be connected to a data processor for receiving and processing data from the device, as well as operating the electrophoretic device The systems are based on having libraries available comprising a plurality of e-tags that comprise at least a plurality of different mobility-identifying regions, so as to be separable in an electrophoresis with the entities to which the mobility-identifying regions are attached. The mobility-identifying regions are retained in the product of the reaction, where the product is modified by the gain and/or loss of a group that changes the mass and may also change the charge of the product, as compared to the starting material. In some instances, the mobility-identifying region may be joined to a target-binding region by a cleavable bond, so that the mobility-identifying region is released for analysis subsequent to the modification of the target-binding region, e.g. complex formation.

The subject invention provides compositions and methods for improved analysis of complex mixtures, where one is interested in the simultaneous identification of a plurality of entities, such as nucleic acid or amino acid sequences, snps, alleles, mutations, proteins, haptens, protein family members, expression products, etc., analysis of the response of a plurality of entities to an agent that can affect the mobility of the entities, and the like. Libraries of differentiable compounds are provided, where the compounds comprise a mobility-identifying region (including mass-identifying region) ("mir"), that provides for ready identification by electrophoresis or mass spectrometry (differentiation by mobility in an electrical field or magnetic field), by itself or in conjunction with a detectable label. Depending on the determination the product may also include one or more nucleotides or their equivalent, one or more amino acids or their equivalent, a functionality resulting from the release of the target-binding region or a modified functionality as a result of the action of an agent on the target-binding region.

The methodology involves employing detectable tags that can be differentiated by electrophoretic mobility or mass. The tags comprise mobility-identifying regions joined to a moiety that will undergo a change to produce a product. Depending on the nature of the change, the change may involve a change in mass and/or charge of the mir, the release of the mir from all or a portion of the target-binding region or may provide for the ability to sequester the mir from the starting material for preferential release of the mir. The differentiable tags, whether identified by electrophoresis or mass spectrometry, comprising the mir, with or without the detectable label and a portion of the target-binding region will be referred to as "e-tags."

In addition, the subject invention employs a variety of reagent systems, where a binding event results in a change in mobility of the e-tag. The binding event is between a target-binding region and a target, and the reagent system recognizes this event and, changes the nature of the e-tag containing target-binding region, so that the mobility and/or mass of the product is different from the starting material. The reagent system will frequently involve an enzyme and the reagent system may comprise the target. The effect of the reagent system is to make or break, a bond by physical, chemical or enzymatic means. Each of the products of the different e-tag containing target-binding regions can be accurately detected, so as to determine the occurrence of the binding event.

The subject invention may be used for a variety of multiplexed analyses involving the action of one or more agents on a plurality of reagents comprising the mir and a target-binding region that undergoes a change as a result of a chemical reaction, resulting in a change in mobility of the product as compared to the starting material. The reaction may be the result of addition or deletion in relation to the target-binding region, so that the resulting product may be sequestered from the starting material. The subject systems find use in nucleic acid and protein analyses, reactions, particularly enzyme reactions, where one or more enzymes are acting on a group of different potential or actual substrates, and the like.

The e-tags are a group of reagents having a mir that with the other regions to which the mir is attached during separation provide for unique identification of an entity of interest. The mir of the e-tags can vary from a bond to about 100 atoms in a chain, usually not more than about 60 atoms, more usually not more than about 30 atoms, where the atoms are carbon, oxygen, nitrogen, phosphorous, boron and sulfur. Generally, when other than a bond, the mir will have from 0 to 40, more usually from 0 to 30 heteroatoms, which in addition to the heteroatoms indicated above will include halogen or other heteroatom. The total number of atoms other than hydrogen will generally be fewer than 200 atoms, usually fewer than 100 atoms. Where acid groups are present, depending upon the pH of the medium in which the mir is present, various cations may be associated with the acid group. The acids may be organic or inorganic, including carboxyl, thionocarboxyl, thiocarboxyl, hydroxamic, phosphate, phosphite, phosphonate, sulfonate, sulfinate, boronic; nitric, nitrous, etc. For positive charges, substituents will include amino (includes ammonium), phosphonium, sulfonium, oxonium,; etc., where substituents will generally be aliphatic of from about 1–6 carbon atoms, the total number of carbon atoms per heteroatom, usually be less than about 12, usually, less than about: 9. The mir may be neutral or charged depending on the other regions to which the mir is attached, at least one of the regions having at least one charge. Neutral mirs will generally be polymethylene, halo- or polyhaloalkylene or aralkylene (a combination of aromatic—includes heterocyclcic—and aliphatic groups), where halogen will generally be fluorine, chlorine, bromine or iodine, polyethers, particularly, polyoxyalkylene, wherein alkyl is of from 2–3 carbon atoms, polyesters, e.g. polyglycolide and polylactide, dendrimers, comprising ethers or thioethers, oligomers of addition and condensation monomers, e.g. acrylates, diacids and diols, etc. The side chains include amines, ammonium salts, hydroxyl groups, including phenolic groups, carboxyl groups, esters, amides, phosphates, heterocycles, particularly nitrogen heterocycles, such as the nucleoside bases and the amino acid side chains, such as imidazole and quinoline, thioethers, thiols, or other groups of interest to change the mobility of the e-tag. The mir may be a homooligomer or a heterooligomer, having different monomers of the same or different chemical characteristics, e.g., nucleotides and amino acids. Desirably neutral mass differentiating groups will be combined with short charged sequences to provide the mir.

The charged mirs will generally have only negative or positive charges, although, one may have a combination of charges, particularly where a region to which the mir is attached is charged and the mir has the opposite charge. The mirs may have a single monomer that provides the different functionalities for oligomerization and carry a charge or two monomers may be employed, generally two monomers. One may use substituted diols, where the substituents are charged and dibasic acids. Illustrative of such oligomers are the combination of diols or diamino, such as 2,3-dihydroxypropionic acid, 2,3-dihydroxysuccinic acid, 2,3-diaminosuccinic acid, 2,4-:dihydroxyglutaric acid, etc. The diols or diamino compounds can be linked by dibasic acids, which dibasic acids include the inorganic dibasic acids indicated above, as well as dibasic acids, such as oxalic acid, malonic acid, succinic acid, maleic acid, furmaric acid, carbonic acid; etc. Instead of using esters, one may use amides, where amino acids or diamines and diacids may be employed. Alternatively, one may link the hydroxyls or amines with alkylene or arylene groups.

By employing monomers that have substituents that provide for charges or which may be modified to provide charges, one can provide for mirs having the desired mass/charge ratio. For example, by using serine or threonine, one may modify the hydroxyl groups with phosphate to provide negatively charged mirs. With arginine, lysine and histidine, one provides for positively charged mirs. Oligomerization may be performed in conventional ways to provide the appropriately sized mir. The different mirs having different orders of oligomers, generally having from 1 to 20 monomeric units, more usually about 1 to 12, where a unit intends a repetitive unit that may have from 1 to 2 different monomers. For the most part, oligomers will be used with other than nucleic acid target-binding regions. The polyfunctionality of the monomeric units provides for functionalities at the termini that may be used for conjugation to other moieties, so that one may use the available functionality for reaction to provide a different functionality. For example, one may react a carboxyl group with an aminoethylthiol, to replace the carboxyl group with a thiol functionality for reaction with an activated olefin.

By using monomers that have 1–3 charges, one may employ a low number of monomers and provide for mobility variation with changes in molecular weight. Of particular interest are polyolpolycarboxylic acids having from about two to four of each functionality, such as tartaric acid, 2,3-dihydroxyterephthalic acid, 3,4-dihydroxyphthalic acid, $\Delta^5$-tetrahydro-3,4-dihydroxyphthalic acid, etc. To provide for an additional negative charge, these monomers may be oligomerized with a dibasic acid, such as a phosphoric acid derivative to form the phosphate diester. Alternatively, the carboxylic acids could be used with a diamine to form a polyamide, while the hydroxyl groups could be used to form esters, such as phosphate esters, or ethers such as the ether of glycolic acid, etc. To vary the mobility, various aliphatic groups of differing molecular weight may be employed, such as polymethylenes, polyoxyalkylenes, polyhaloaliphatic or aromatic groups, polyols, e.g. sugars, where the mobility will differ by at least about 0.01, more usually at least about 0.02 and more usually at least about 0.5. Alternatively, the libraries may include oligopeptides for providing the charge, particularly oligopeptides of from 2–6, usually 2–4 monomers, either positive charges resulting from lysine, arginine and histidine or negative charges, resulting from aspartic and glutamic acid. Of course, one need not use naturally occurring amino acids, but unnatural or synthetic amino acids, such as taurine, phosphate substituted serine or threonine, S-α-succinylcysteine, co-oligomers of diamines and amino acids, etc.

Where the e-tags are used for mass detection, as with mass spectrometry, the e-tags need not be charged but merely differ in mass, since a charge will be imparted to the e-tags by the mass spectrometer. Thus, one could use the same or similar monomers, where the functionalities would be neutral or made neutral, such as esters and amides of carboxylic acids. Also, one may vary the e-tags by isotopic substitution, such as $^2H$, $^{18}O$, $^{14}C$, etc.

The libraries will ordinarily have at least about 5 members, usually at least about members, and may have 100 members or more, for convenience generally having about 50–75 members. Some members may be combined in a single container or be provided in individual containers, depending upon the region to which the mir is attached. The members of the library will be selected to provide clean separations in electrophoresis, when capillary electrophoresis is the analytical method. To that extent, mobilities will differ as described above, where the separations may be greater, the larger the larger the number of molecules in the band to be analyzed. Particularly, non-sieving media may be employed in the separation.

An e-tag will be a molecule, which is labeled with a directly detectable label or can be made so by having a functionality that can be used for bonding to a detectable label, if such label is required for detection. The e-tags will be differentiated by their electrophoretic mobility, usually their mass/charge ratio, to provide different mobilities for each e-tag. Although in some instances the e-tags may have identical mass/charge ratios, such as oligonucleotides, but differ in size or shape and therefore exhibit different electrophoretic mobilities under appropriate conditions. Therefore, the tags will be amenable to electrophoretic separation and detection, although other methods of differentiating the tags may also find use. The e-tag may be joined to any convenient site on the target binding reagent, without interfering with the synthesis, release and binding of the e-tag labeled reagent. For nucleotides, the e-tag may be bound to a site on the base, either an annular carbon atom or a hydroxyl or amino substituent.

The e-tag may be linked by a stable bond or one, which may be cleavable, thermally, photolytically or chemically. There is an interest in cleaving the e-tag from the target-binding region in situations where cleavage of the target-binding region results in significant cleavage at other than the desired site of cleavage, resulting in satellite cleavage products, such as di- and higher oligonucleotides and this family of products interferes with the separation and detection of the e-tags. However, rather than requiring an additional step in the identification of the tags by releasing them from the base to which they are attached, one can modify the target binding sequence to minimize obtaining cleavage at other than the desired bond, for example, the ultimate or penultimate phosphate link in a nucleic acid sequence. For immunoassays involving specific binding members, bonding of the e-tag will usually be through a cleavable bond to a convenient functionality, such as carboxy, hydroxy, amino or thiol, particularly as associated with proteins, lipids and saccharides.

If present, the nature of the cleavable link resulting in release of the e-tag may be varied widely. Numerous linkages are available, which are thermally, photolytically or chemically labile. See, for example, U.S. Pat. No. 5,721,099. Where detachment of the product from all or a portion of the target-binding region is desired, there are numerous functionalities and reactants, which may be used. Conveniently, ethers may be used, where substituted benzyl ether or derivatives thereof, e.g. benzhydryl ether, indanyl ether, etc. may be cleaved by acidic or mild reductive conditions. Alternatively, one may employ beta-elimination, where a mild base may serve to release the product. Acetals, including the thio analogs thereof, may be employed, where mild acid, particularly in the presence of a capturing carbonyl compound, may serve.; By combining formaldehyde, HCl and an alcohol moiety, an α-chloroether is formed. This may then be coupled with an hydroxy functionality to form the acetal. Various photolabile linkages may be , employed, such as o-nitrobenzyl, 7-nitroindanyl; 2-nitrobenzhydryl ethers or esters, etc.

For a list of cleavable linkages, see, for example, Greene and Wuts, Protective Groups in Organic Synthesis, 2$^{nd}$ ed. Wiley, 1991. The versatility of the various systems that have been developed allows for broad variation in the conditions for attachment of the e-tag entities.

Various functionalities for cleavage are illustrated by: silyl groups being cleaved with fluoride, oxidation, acid, bromine or chlorine; o-nitrobenzyl with light; catechols with cerium salts; olefins with ozone, permanganate or osmium tetroxide; sulfides with singlet oxygen or enzyme catalyzed oxidative cleavage with hydrogen peroxide, where the resulting sulfone can undergo elimination; furans with oxygen or bromine in methanol; tertiary alcohols with acid; ketals and acetals with acid; α and β-substituted ethers and esters with base, where the substituent is an electron withdrawing group, e.g., sulfone, sulfoxide, ketone, etc., and the like The mir will link the target-binding region and the detectable label molecule, usually a fluorescer, or a functionality, which may be used for linking to a detectable label molecule. By having different functionalities, which may be individually bonded to a detectable label molecule, one enhances the opportunity for diversity of the e-tags. Using different fluorescers for joining to the different functionalities, the different fluorescers can provide differences in light emission and mass/charge ratios for the e-tags.

As discussed previously, the mir may be an oligomer, where the monomers may differ as to mass and charge. For convenience and economy, monomers will generally be commercially available, but if desired, they may be originally synthesized.: Monomers: which are commercially available and readily lend themselves to oligomerization include amino acids, both natural and synthetic, monosaccharides, both natural and synthetic, while other monomers include hydroxyacids, where the acids may be organic or inorganic, e.g. carboxylic, phosphoric, boric, sulfonic, etc., and amino acids, where the acid is inorganic, and the like. In some instances, nucleotides, natural or synthetic, may find use. The monomers may be neutral, negatively charged or positively charged or modified to be charged or neutral, e.g. sugars that are phosphorylated, amino acids that are acylated. Normally, the charges of the monomers in the mir will be the same, so that in referring to the mass/charge ratio, it will be related to the same charge. Where the label has a different charge from the mir, this will be treated as if the number of charges is reduced by the number of charges on the mir. For natural amino acids, the positive charges may be obtained from lysine, arginine and histidine, while the negative charges may be obtained from aspartic and glutamic acid. For nucleotides, the charges will be obtained from the phosphate and any substituents that may be present or introduced onto the base. For sugars, sialic acid and uronic acids of the various sugars, or substituted sugars may be employed.

The mir may be joined in any convenient manner to the unit of the target-binding region, such as the base of the nucleoside or the amino acid of a protein. Various functionalities which may be used include alkylamine, amidine, thioamide, ether, urea, thiourea, guanidine, azo, thioether and carboxylate, sulfonate, and phosphate esters, amides and thioesters.

Besides the nature of the mir, as already indicated, diversity can be achieved by the chemical and optical characteristics of the label, the use of energy transfer complexes, variation in the chemical nature of the mir, which affects mobility, such as folding, interaction with the solvent and ions in the solvent, and the like. As already suggested, the mir will usually be an oligomer, where the mir may be synthesized on a support or produced by cloning or expression in an appropriate host. Conveniently, polypeptides can be produced where there is only one cysteine or serine/threonine/tyrosine, aspartic/glutamic acid, or lysine/arginine/histidine, other than an end group, so that there is a unique functionality, which may be differentially functionalized. By using protective groups, one can distinguish a side chain functionality from a terminal amino acid functionality. Also, by appropriate design, one may provide for preferential reaction between the same functionalities present at different sites on the mir. Whether one uses synthesis or cloning for preparation of oligopeptides, will to a substantial degree depend on the length of the mir.

The e-tag, which is detected, will comprise the mir, generally a label, and optionally a portion of the target-binding region, all of the target-binding region when the target is an enzyme and the target-binding region is the substrate. Generally, the e-tag will have a charge/mass ratio in the range of about −0.0001 to 1, usually in the range of about −0.001 to about 0.5. Mobility is proportional to $q/M^{2/3}$, where q is the charge on the molecule and M is the mass of the molecule. Desirably, the difference in mobility under the conditions of the determination between the closest electrophoretic labels will be at least about 0.001, usually 0.002, more usually at least about 0.01, and may be 0.02 or more.

Depending upon the reagent to which the e-tag is attached, there may be a single e-tag or a plurality of e-tags, generally ranging from about 1–100, more usually ranging from about 1–40, more particularly ranging from about 1–20. The number of e-tags bonded to a single target-binding region will depend upon the sensitivity required, the solubility of the e-tag conjugate, the effect on the assay of a plurality of e-tags, and the like. For oligomers or polymers, such as nucleic acids and poly(amino acids), e.g. peptides and proteins, one may have one or a plurality of e-tags, while for synthetic or naturally occurring non-oligomeric compounds, usually there will be only 1–3, more usually 1–2 e-tags.

The e-tag for use in electrophoresis may be represented by the formula:

R—L—T wherein R is a label, particularly a fluorescer L is a mir a bond or a linking group as described previously, where L and the regions to which L is attached provide for the variation in mobility of the e-tags. T comprises a portion of the target-binding region, particularly a nucleoside base, purine or pyrimidine, and is; the base, a nucleoside, nucleotide or nucleotide triphosphate, an amino acid, either naturally occurring or synthetic, or other functionality that may serve to participate in the synthesis of an oligomer, when T is retained, and is otherwise a functionality resulting from the cleavage between L, the mir, and the target-binding region. L provides a major factor in the differences in mobility between the different e-tags, in combination with the label and any residual entity, which remain with the mir. L may or may not include a cleavable bond, depending upon whether the terminal entity to which L is attached is to be retained or completely removed.

L has been substantially described as the mir and as indicated previously may include charged groups, uncharged polar groups or be non-polar. The groups may be alkylene and substituted alkylenes, oxyalkylene and polyoxyalkylene, particularly alkylene of from 2 to 3 carbon atoms, arylenes and substituted arylenes, polyamides, polyethers, polyalkylene amines, etc. Substituents may include heteroatoms, such as halo, phosphorous, nitrogen, oxygen, sulfur, etc., where the substituent may be halo, nitro, cyano, non-oxo-carbonyl, e.g. ester, acid and amide, oxo-carbonyl, e.g. aldehyde and keto, amidine, urea, urethane, guanidine, carbamyl, amino and substituted amino, particularly alkyl substituted amino, azo, oxy, e.g. hydroxyl and ether, etc., where the substituents will generally be of from about 0 to 10 carbon atoms, while L will generally be of from about 1 to 100 carbon atoms, more usually of from about 1 to 60 carbon atoms and preferably about 1 to 36 carbon atoms. L will be joined to the label and the target-binding region by any convenient functionality, such as carboxy, amino, oxy, phospo, thio, iminoether, etc., where in many cases the label and the target-binding region will have a convenient functionality for linkage.

The number of heteroatoms in L is sufficient to impart the desired charge to the label conjugate, usually from about 1 to about 200, more usually from about 2 to 100, heteroatoms. The heteroatoms in L may be substituted with atoms other than hydrogen.

The charge-imparting moieties of L may be, for example, amino acids, tetraalkylammonium, phosphonium, phosphate diesters, carboxylic acids, thioacids, sulfonic acids, sulfate groups, phosphate monoesters, and the like and combinations of one or more of the above. The number of the above components of L is such as to achieve the desired number of different charge-imparting moieties. The amino acids may be, for example, lysine, aspartic acid, alanine, gamma-aminobutyric acid, glycine, β-alanine, cysteine, glutamic acid, homocysteine, β-alanine and the like. The phosphate diesters include, for example, dimethyl phosphate diester, ethylene glycol linked phosphate diester, and so forth. The thioacids include, by way of example, thioacetic acid, thiopropionic acid, thiobutyric acid and so forth. The carboxylic acids preferably have from 1 to 30 carbon atoms, more preferably, from 2 to 15 carbon atoms and preferably comprise one or more heteroatoms and may be, for example, acetic acid derivatives, formic acid derivatives, succinic acid derivatives, citric acid derivatives, phytic acid derivatives and the like. In one embodiment of the present invention the label conjugates having different charge to mass ratios may comprise fluorescent compounds, each of which are linked to molecules that impart a charge to the fluorescent compound conjugate. As indicated previously, desirably the linking group has an overall negative charge, preferably having in the case of a plurality of groups, groups of the same charge, where the total charge may be reduced by having one or more oppositely charged moiety.

Of particular interest for L is to have two sub-regions, a common charged sub-region, which will be common to a group of e-tags, and a varying uncharged, a non-polar or polar sub-region, that will vary the mass/charge ratio. This permits ease of synthesis, provides for relatively common chemical and physical properties and permits ease of handling. For negative charges, one may use dibasic acids that are substituted with functionalities that permit low orders of oligomerization, such as hydroxy and amino, where amino will usually be present as neutral amide. These charge imparting groups provide aqueous solubility and allow for various levels of hydrophobicity in the other sub-region. Thus the uncharged sub-region could employ substituted dihydroxybenzenes, diaminobenzenes, or aminophenols, with one or greater number of aromatic rings, fused or non-fused, where substituents[]may be halo, nitro, cyano, alkyl, etc., allowing for great variation in molecular weight by using sa common building block. Where the other regions of the e-tag impart charge to the e-tag, L, may be neutral.

In some instances, where release of the e-tag results in an available functionality that can be used to react with a detectable label, there will be no need for R to be a functionality. The release of the e-tag can provide an hydroxyl, amino, carboxy or thiol group, where each may serve as the site for conjugation to the detectable label. To the extent that the e-tag is released free of a component of the target-binding region, this opportunity will be present. In that case, R is the unreactive (under the conditions of the conjugation) terminus of L and T is a functionality for release of the e-tag that may be joined to all or a portion of the target-binding region or may be available for binding to all or a portion of the target-binding region.

Combinations of particular interest comprise a fluorescent compound and a different amino acid or combinations thereof in the form of a peptide or combinations of amino acids and thioacids or other carboxylic acids. Such compounds are represented by the formula:

R'—L'—T' wherein R' is a fluorescer, L' is is an amino acid or a peptide or combinations of amino acids and thioacids or other carboxylic acids and T' is a functionality for linking to a nucleoside base or is a nucleoside, nucleotide or nucleotide triphosphate or other moiety as described above for T.

In one embodiment of the present invention, the charge-imparting moiety is conveniently composed primarily of amino acids but also may include thioacids and other carboxylic acids having from one to five carbon atoms. The charge-imparting moiety may have from 1 to 30, preferably 1 to 20, more preferably, 1 to 10 amino acids per moiety and may also comprise 1 to 3 thioacids or other carboxylic acids. However, when used with an uncharged sub-region, the charged sub-region will generally have from 1–4, frequently 1–3 amino acids. As mentioned above, any amino acid, both naturally occurring and synthetic may be employed.

In a particular embodiment the label conjugates may be represented by the formula:

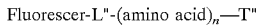

Fluorescer-L"-(amino acid)$_n$—T"

wherein L" is a bond or a linking group of from 1 to 20 atoms other than hydrogen, n is 1 to 20, and T" comprises a nucleoside base, purine or pyrimidine, including a base, a nucleoside, a nucleotide or nucleotide triphosphates, an amino acid, or functionality for linking to the target-binding region. An example of label conjugates in this embodiment, by way of illustration and not limitation, is one in which the fluorescer is fluorescein, L" is a bond in the form of an amide linkage involving the meta-carboxyl of the fluorescein and the terminal amine group of lysine, and T" is a nucleotide triphosphate. These label conjugates may be represented as follows:

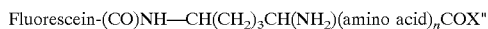
Fluorescein-(CO)NH—CH(CH$_2$)$_3$CH(NH$_2$)(amino acid)$_n$COX"

wherein X is as set forth in Table 1.

TABLE 1

| No. | X | Charge |
|---|---|---|
| 1 | OH | −2 |
| 2 | NH-lysine | −1 |
| 3 | NH-(lysine)$_2$ | neutral |
| 4 | NH-alanine | −3 |
| 5 | NH-aspartic acid | −4 |
| 6 | NH-(aspartic acid)$_2$ | −5 |
| 7 | NH-(aspartic acid)$_3$ | −6 |
| 8 | NH-(aspartic acid)$_4$ | −7 |
| 9 | NH-(aspartic acid)$_5$ | −8 |
| 10 | NH-(aspartic acid)$_6$ | −9 |
| 11 | NH-(aspartic acid)$_7$ | −10 |
| 12 | NH-alanine-lysine | −2 (unique q/M) |
| 13 | NH-aspartic acid-lysine | −3 (unique q/M) |
| 14 | NH-(aspartic acid)$_2$-lysine | −4 (unique q/M) |
| 15 | NH-(aspartic acid)$_3$-lysine | −5 (unique q/M) |
| 16 | NH-(aspartic acid)$_4$-lysine | −6 (unique q/M) |
| 17 | NH-(aspartic acid)$_5$-lysine | −7 (unique q/M) |
| 18 | NH-(aspartic acid)$_6$-lysine | −8 (unique q/M) |
| 19 | NH-(aspartic acid)$_7$-lysine | −9 (unique q/M) |
| 20 | NH-(aspartic acid)$_8$-lysine | −10 (unique q/M) |
| 21 | NH-(lysine)$_4$ | +1 |
| 22 | NH-(lysine)$_5$ | +2 | wherein q is charge, M is mass and mobility is $qEM^{2/3}$. Examples of such label conjugates are shown in FIG. 1C.

Table 2 shows various characteristics for the label conjugates.

TABLE 2

| No. | Mass(M) | Charge(q) | M$^{2/3}$ | q/M$^{2/3}$ | Mobility |
|---|---|---|---|---|---|
| 1 | 744.82 | 0 | 82.16765 | 0 | 0 |
| 2 | 877.02 | 0 | 91.62336 | 0 | 0 |
| 3 | 828.71 | −1 | 88.22704 | −0.01133 | −0.16546 |
| 4 | 970.71 | −1 | 98.03767 | −0.0102 | −0.1489 |
| 5 | 700.82 | −2 | 78.89891 | −0.02535 | −0.37004 |
| 6 | 842.83 | −2 | 89.22639 | −0.2241 | −0.32721 |
| 7 | 815.92 | −3 | 87.31692 | −0.03436 | −0.50155 |
| 8 | 957.92 | −3 | 97.17461 | −0.03087 | −0.45067 |
| 9 | 931.02 | −4 | 95.34677 | −0.04195 | −0.61242 |
| 10 | 1073.02 | −4 | 104.8106 | −0.03816 | −0.55712 |
| 11 | 1046 | −5 | 103.0436 | −0.04852 | −0.70834 |
| 12 | 1188 | −5 | 112.1702 | −0.04458 | −0.65071 |
| 13 | 1161 | −6 | 110.4642 | −0.05432 | −0.79291 |
| 14 | 1303 | −6 | 119.297 | −0.05029 | −0.7342 |
| 15 | 1276 | −7 | 117.6433 | −0.0595 | −0.86861 |
| 16 | 1418 | −7 | 126.2169 | −0.05546 | −0.80961 |
| 17 | 1391 | −8 | 124.6096 | −0.0642 | −0.9372 |
| 18 | 1533 | −8 | 132.952 | −0.06017 | −0.87839 |
| 19 | 1506 | −9 | 131.3863 | −0.0685 | −0.99997 |
| 20 | 1648 | −9 | 139.6205 | −0.06451 | −0.94167 |
| 21 | 793.52 | 1 | 85.7114 | 0.011667 | 0.170316 |
| 22 | 935.52 | 1 | 95.65376 | 0.010454 | 0.152613 |

Another group of e-tags has a mir which is dependent on using an alkylene or aralkylene (comprising a divalent aliphatic group having 1–2 aliphatic regions and 1–2 aromatic regions, generally benzene), where the groups may be substituted or unsubstituted, usually unsubstituted, of from 2–16, more usually 2–12, carbon atoms, where the mir may link the same or different fluorescers to a monomeric unit, e.g. a nucleotide. The mir may terminate in a carboxy, hydroxy or amino group, being present as an ester or amide. By varying the substituents on the fluorophor, one can vary the mass in units of at least 5 or more, usually at least about 9, so as to be able to obtain satisfactory separation in capillary electrophoresis. To provide further variation, a thiosuccinimide group may be employed to join alkylene or aralkylene groups at the nitrogen and sulfur, so that the total number of carbon atoms may be in the range of about 2–30, more usually 2–20. Instead of or in combination with the above groups and to add hydrophilicity, one may use alkyleneoxy groups.

The label conjugates may be prepared utilizing conjugating techniques that are well known in the art. The charge-imparting moiety L may be synthesized from smaller molecules that have functional groups that provide for linking of the molecules to one another, usually in a linear chain. Such functional groups include carboxylic acids, amines, and hydroxy- or thiol-groups. In accordance with the present invention the charge-imparting moiety may have one or more side groups pending from the core chain. The side groups have a functionality to provide for linking to a label or to another molecule of the charge-imparting moiety.

Common functionalities of L resulting from the reaction of the functional groups employed are exemplified by forming a covalent bond between the molecules to be conjugated. Such functionalities are disulfide, amide, thioamide, dithiol, ether, urea, thiourea, guanidine, azo, thioether, carboxylate and esters and: amides containing sulfur and phosphorus such as, e.g. sulfonate, phosphate esters, sulfonamides, thioesters, etc., and the like.

The chemistry for performing the types of syntheses to form the charge-imparting moiety as a peptide chain is well known in the art. See, for example, Marglin, et al., *Ann. Rev. Biochem.* (1970);39:841–866. In general, such syntheses involve blocking, with an appropriate protecting group, those functional groups that are not to be involved in the reaction. The free functional groups are then reacted to form the desired linkages. The peptide can be produced on a resin as in the Merrifield synthesis (Merrifield, *J. Am. Chem. Soc.* (1980) 85:2149–2154 and Houghten et al., *Int. J. Pep. Prot. Res.* (1980) 16:311–320. The peptide is then removed from the resin according to known techniques.

A summary of the many techniques available for the synthesis of peptides may be found in J. M. Stewart, et al., "Solid Phase Peptide Synthesis, W. H. Freeman Co, San Francisco (1969); and J. Meienhofer, "Hormonal Proteins and Peptides", (1973), vol. 2, p 46., Academic Press (New York), for solid phase peptide synthesis and E. Schroder, et al., "The Peptides, vol. 1, Academic Press (New York), 1965 for solution synthesis.

In general, these methods comprise the sequential addition of one or more amino acids, or suitably protected amino acids, to a growing peptide chain. Normally, a suitable protecting group protects either the amino or carboxyl group of the first amino acid. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide. The protecting groups are removed, as desired, according to known methods depending on the particular protecting group utilized. For example, the protecting group may be removed by reduction with hydrogen and palladium on charcoal, sodium in liquid ammonia, etc.; hydrolysis with trifluoroacetic acid, hydrofluoric acid, and the like.

After the synthesis of the peptide is complete, the peptide is removed from the resin by conventional means such as ammonolysis, acidolysis and the like. The fully deprotected peptide may then be purified by techniques known in the art such as chromatography, for example, adsorption chromatography; ion exchange chromatography, partition chromatography, high performance liquid chromatography, thin layer chromatography, and so forth.

As can be seen, the selected peptide representing a charge-imparting moiety may be synthesized separately and then attached to the label either directly or by means of a linking group. On the other hand, the peptide may be synthesized as a growing chain on the label. In any of the above approaches, the linking of the peptide or amino acid to the label may be carried out using one or more of the techniques described above for the synthesis of peptides or for linking moieties to labels.

Synthesis of e-tags comprising nucleotides can be easily and effectively achieved via assembly on solid phase support during probe synthesis using standard phosphoramidite chemistries. The e-tags are assembled at the 5 end of probes after coupling of a final nucleosidic residue, which becomes part of the e-tag during the assay. In one approach, the e-tag is constructed sequentially from a single or several monomeric phosphoramidite building blocks (one containing a dye residue), which are chosen to generate tags with unique electrophoretic mobilities based on their mass to charge ratio. The e-tag is thus composed of monomeric units of variable charge to mass ratios bridged by phosphate linkers (Figure A). The separation of e-tags, which differ by 9 mass units (Table 3) has been demonstrated. The nucleosidic phosphoramidites employed for tag synthesis are initially either modified or natural residues. Fluorescein has been the initial dye employed but other dyes can be used as well. Some of the combinations of phosphoramidite building blocks with their predicted elution times are presented in Table 4. e-tags are synthesized to generate a contiguous spectrum of signals, one eluting after another with none of them coeluting (Figure B).

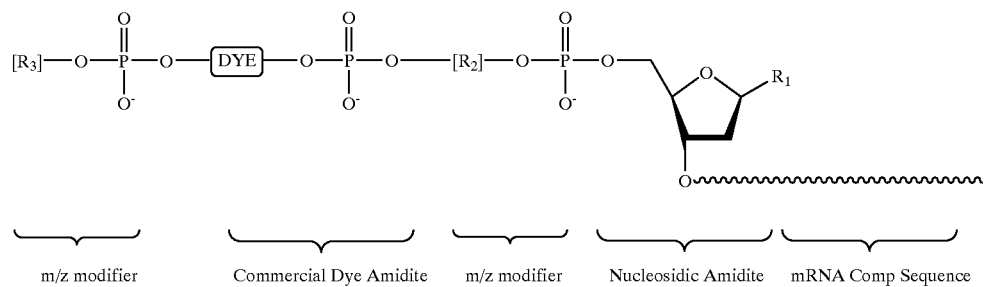

Figure A. The design and synthesis of E-Tags on solid phase support using standard phosphoramidite coupling chemistry.

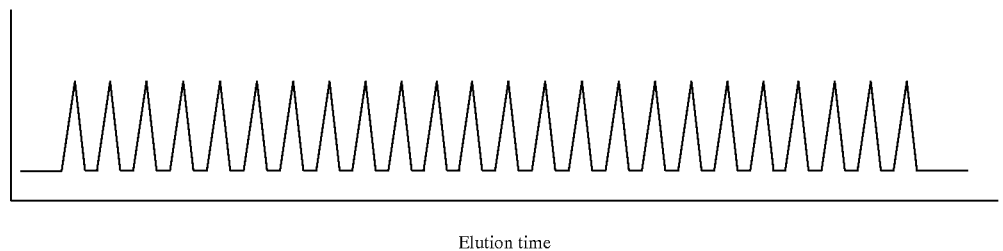

Figure B. Separation of e-tags designed to possess unique charge to mass ratios.

TABLE 3
| E-Tag | Elution time on CE (sec) | Mass |
|---|---|---|
| 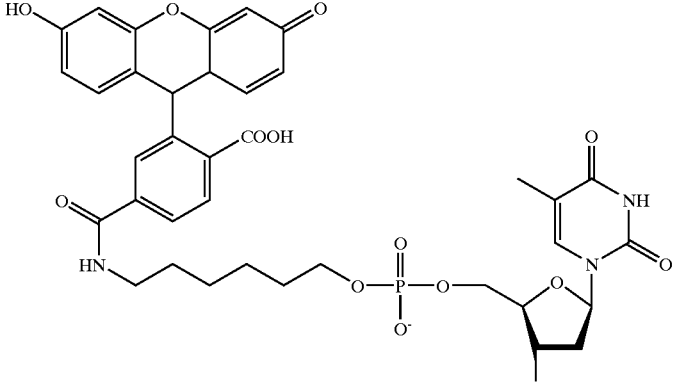 | 385 | 788 |
| 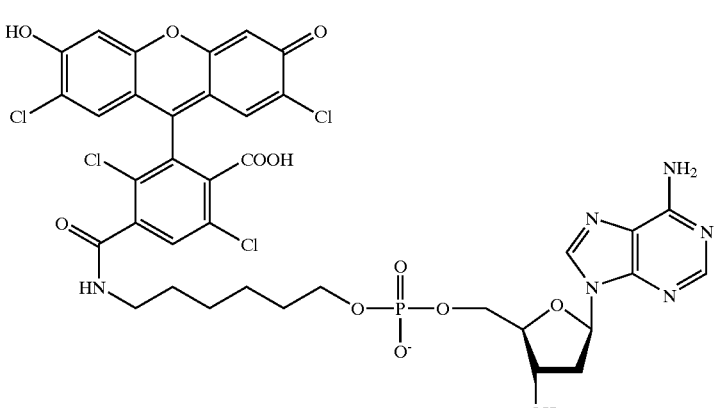 | 428 | 925 |
| 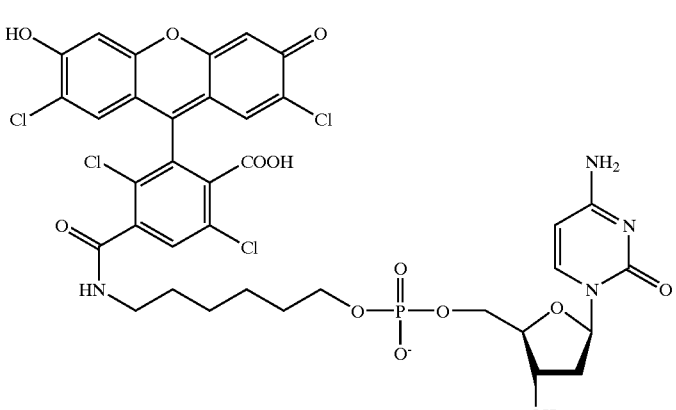 | 438 | 901 |

TABLE 3-continued

| E-Tag | Elution time on CE (sec) | Mass |
|---|---|---|
| [structure: tetrachlorofluorescein-amidohexyl-phosphate-dA] | 462 | 994 |
| [structure: tetrachlorofluorescein-amidohexyl-phosphate-dT] | 480 | 985 |
| [structure: dimethoxy-dichlorofluorescein-amidohexyl-phosphate-dC] | 555 | 961 | e-tags that have been separated on a LabCard (detection: 4.7 cm, 200 V/cm).

TABLE 4

| Etag | Charge | Elution Time |
|---|---|---|
| Fluorescein-C(=O)-NH-(CH2)5-O-P(=O)(O-)-O-C3C3C3C3C3C3-dC | −9 | 41.12 |
| Fluorescein-C(=O)-NH-(CH2)5-O-P(=O)(O-)-O-C3C3C3C3C3-dC | −8 | 43.72 |
| Fluorescein-C(=O)-NH-(CH2)5-O-P(=O)(O-)-O-C6C6C6C6C6C6-dC | −9 | 45.66 |
| Fluorescein-C(=O)-NH-(CH2)5-O-P(=O)(O-)-O-C6C6C6C6C6-dC | −8 | 48.14 |
| Fluorescein-C(=O)-NH-(CH2)5-O-P(=O)(O-)-O-C6C6C6C6-dC | −7 | 51.21 |
| Fluorescein-C(=O)-NH-(CH2)5-O-P(=O)(O-)-O-C3C3C9-dC | −6 | 53.53 |
| Fluorescein-C(=O)-NH-(CH2)5-O-P(=O)(O-)-O-C6C6C6-dC | −6 | 55.13 |
| Fluorescein-C(=O)-NH-(CH2)5-O-P(=O)(O-)-O-C3C3-dC | −5 | 57.66 |
| Fluorescein-C(=O)-NH-(CH2)5-O-P(=O)(O-)-O-C3C9-dC | −5 | 60.00 |
| Fluorescein-C(=O)-NH-(CH2)5-O-P(=O)(O-)-O-C9C9-dC | −5 | 62.86 |
| Fluorescein-C(=O)-NH-(CH2)5-O-P(=O)(O-)-O-TTTdC | −6 | 65.00* |
| Fluorescein-C(=O)-NH-(CH2)5-O-P(=O)(O-)-O-TTdC | −5 | 67.50* |
| Fluorescein-C(=O)-NH-(CH2)5-O-P(=O)(O-)-O-C9-dT | −4 | 69.61 |
| Fluorescein-C(=O)-NH-(CH2)5-O-P(=O)(O-)-O-TdC | −4 | 72.00* |

Predicted and experimental (*) elution times of e-tags. $C_3$, $C_6$, $C_9$, $C_{18}$, are commercially available phosphoramidite spacers from Glen Research, Sterling VA. The units are derivatives of N,N-diisopropyl, O-cyanoethyl phosphoramidite, which in the following formulas will be indicated by "Q".

$C_3$ is DMT (dimethoxytrityl)oxypropyl Q; $C_6$ is DMToxyhexyl Q; $C_9$ is DMToxy(triethyleneoxy) Q; $C_{12}$ is DMToxydodecyl Q; $C_{18}$ is DMToxy(hexaethyleneoxy) Q.

All of the above e-tags work well and are easily separable and elute after 40 minutes. To generate tags that elute faster, highly charged low molecular weight tags are required. Several types of phosphoramidite monomers allow for the synthesis of highly charged tags with early elution times. Use of dicarboxylate phosphoramidites (FIG. 5A) allows for the addition of 3 negative charges per coupling of monomer. A variety of fluorescein derivatives (FIG. 5B) allow the dye component of the tag to carry a higher mass than standard fluorescein. Polyhydroxylated phosphoramidites (FIG. 6) in combination with a common phosphorylation reagent enable the synthesis of highly phosphorylated tags. Combinations of these reagents with other mass modifier linker phosphoramidites allow for the synthesis of tags with early elution times.

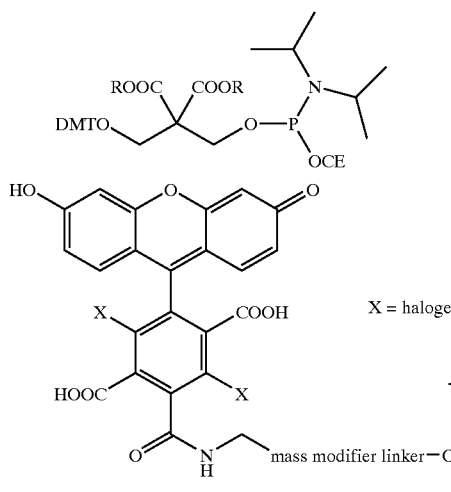

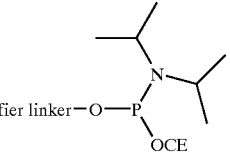

Figure C. Charge modifier phosphoramidites. (EC or CE is cyanoethyl)

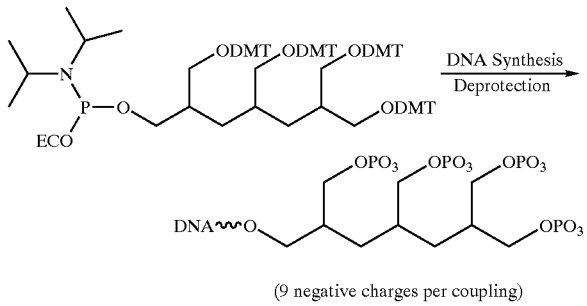

(9 negative charges per coupling)

Figure D. Polyhydroxylated charge modifier phosphoramidites.

The aforementioned label conjugates with different electrophoretic mobility permit a multiplexed amplification and detection of multiple targets, e.g. nucleic acid targets. The label conjugates are linked to oligonucleotides in a manner similar to that for labels in general, by means of linkages that are enzymatically cleavable. It is, of course, within the purview of the present invention to prepare any number of label conjugates for performing multiplexed determinations. Accordingly, for example, with 40 to 50 different label conjugates separated in a single separation channel and 96 different amplification reactions with 96 separation channels on a single plastic chip, one can detect 4000 to 5000 single nucleotide polymorphisms.

The separation of e-tags, which differ by 9 mass units (Table 3) has been demonstrated as shown in FIG. 7. The penultimate coupling during probe synthesis is initially carried out using commercially available modified (and unmodified) phosphoramidites (Table 4). This residue is able to form hydrogen bonds to its partner in the target strand and is considered a mass modifier but could potentially be a charge modifier as well. The phosphate bridge formed during this coupling is the linkage severed during a 5'-nuclease assay. The final coupling is done using a phosphoramidite analogue of a dye. Fluorescein is conveniently employed, but other dyes can be used as well.

One synthetic approach is outlined in Scheme 1. Starting with commercially available 6-carboxy fluorescein, the phenolic hydroxyl groups are protected using an anhydride. Isobutyric anhydride in pyridine was employed but other variants are equally suitable. It is important to note the significance of choosing; an ester functionality as the protecting group. This species remains intact though the phosphoramidite monomer synthesis as well as during oligonucleotide construction. These groups are not removed until the synthesized oligo is deprotected using ammonia. After protection the crude material is then activated in situ via formation of an N-hydroxy succinimide ester (NHS-ester) using DCC as a coupling agent. The DCU byproduct is filtered away and an amino alcohol is added. Many amino alcohols are commercially available some of which are derived from reduction of amino acids. Only the amine is reactive enough to displace N-hydroxy succinimide.

Scheme 1

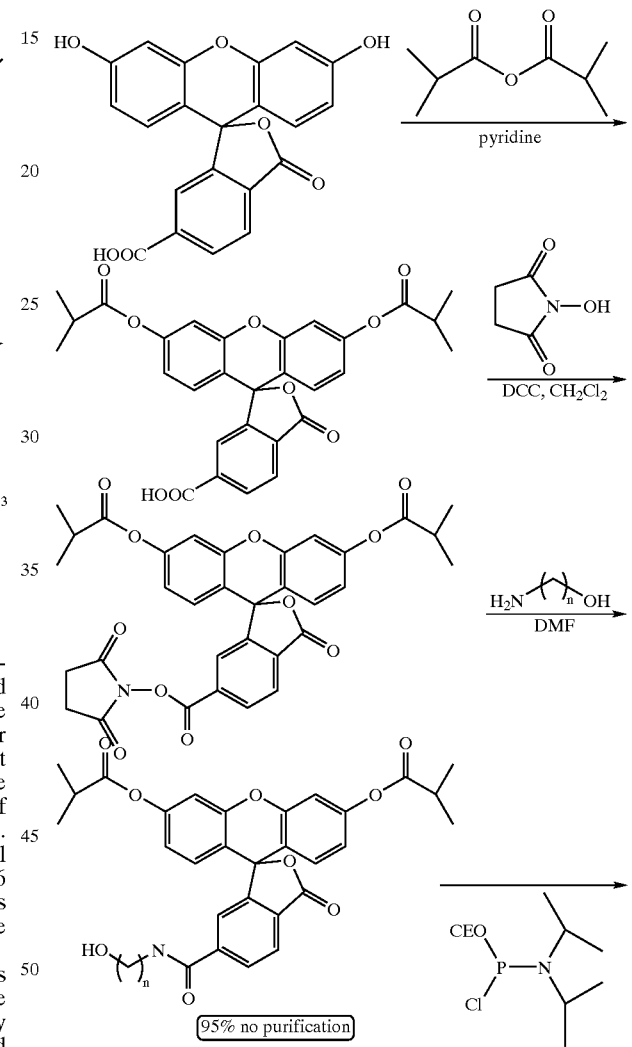

Upon standard extractive workup, a 95% yield of product is obtained. This material is phosphitylated to generate the phosphoramidite monomer (Scheme 1). For the synthesis of additional e-tags, a symmetrical bisamino alcohol linker is used as the amino alcohol (Scheme 2). As such the second amine is then coupled with a multitude of carboxylic acid derivatives (Table 3) prior to the phosphitylation reaction. Using this methodology hundreds if not thousands of e-tags with varying charge to mass ratios can easily be assembled during probe synthesis on a DNA synthesizer using standard chemistries.

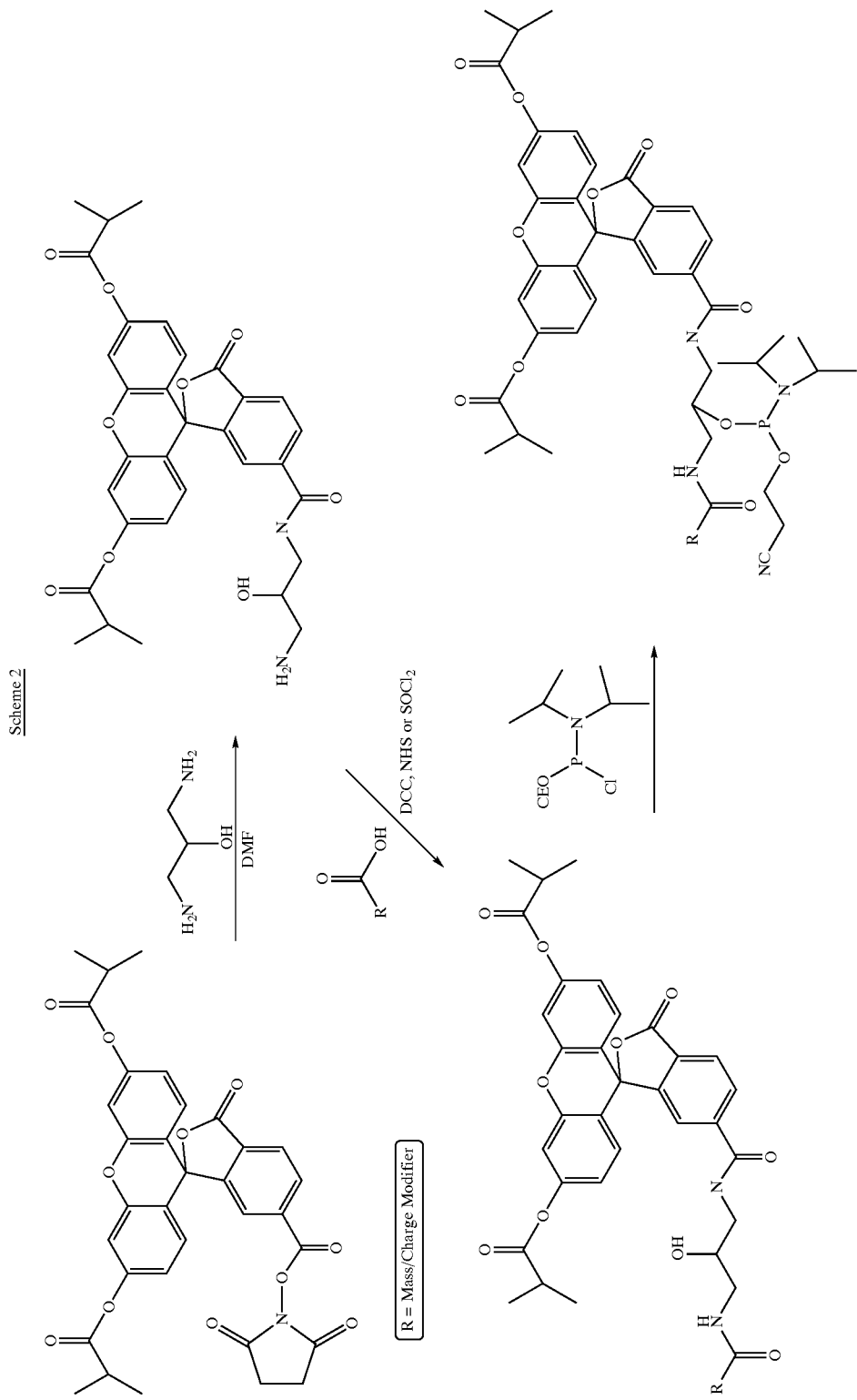

Additional e-tags are accessed via an alternative strategy which uses 5-aminofluorescein as starting material (Scheme 3). Addition of 5-aminofluorescein to a great excess of a diacid chloride in a large volume of solvent allows for the predominant formation of the monoacylated product over dimer formation. The phenolic groups are not reactive under these conditions. Aqueous workup converts the terminal acid chloride to a carboxylic acid. This product is analogous to 6-carboxy fluorescein and using the same series of steps is converted to its protected phosphoramidite monomer (Scheme 3). There are many commercially available di(acid chorides) and diacids, which can be converted to diacid chlorides using $SOCl_2$ or acetyl chloride. This methodology is highly attractive in that a second mass modifier is used. As such, if one has access to 10 commercial modified phosphoramidites and 10 diacid chlorides and 10 amino alcohols there is a potential for 1000 different e-tags. There are many commercial diacid chlorides and amino alcohols (Table 6). These synthetic approaches are ideally suited for combinatorial chemistry.

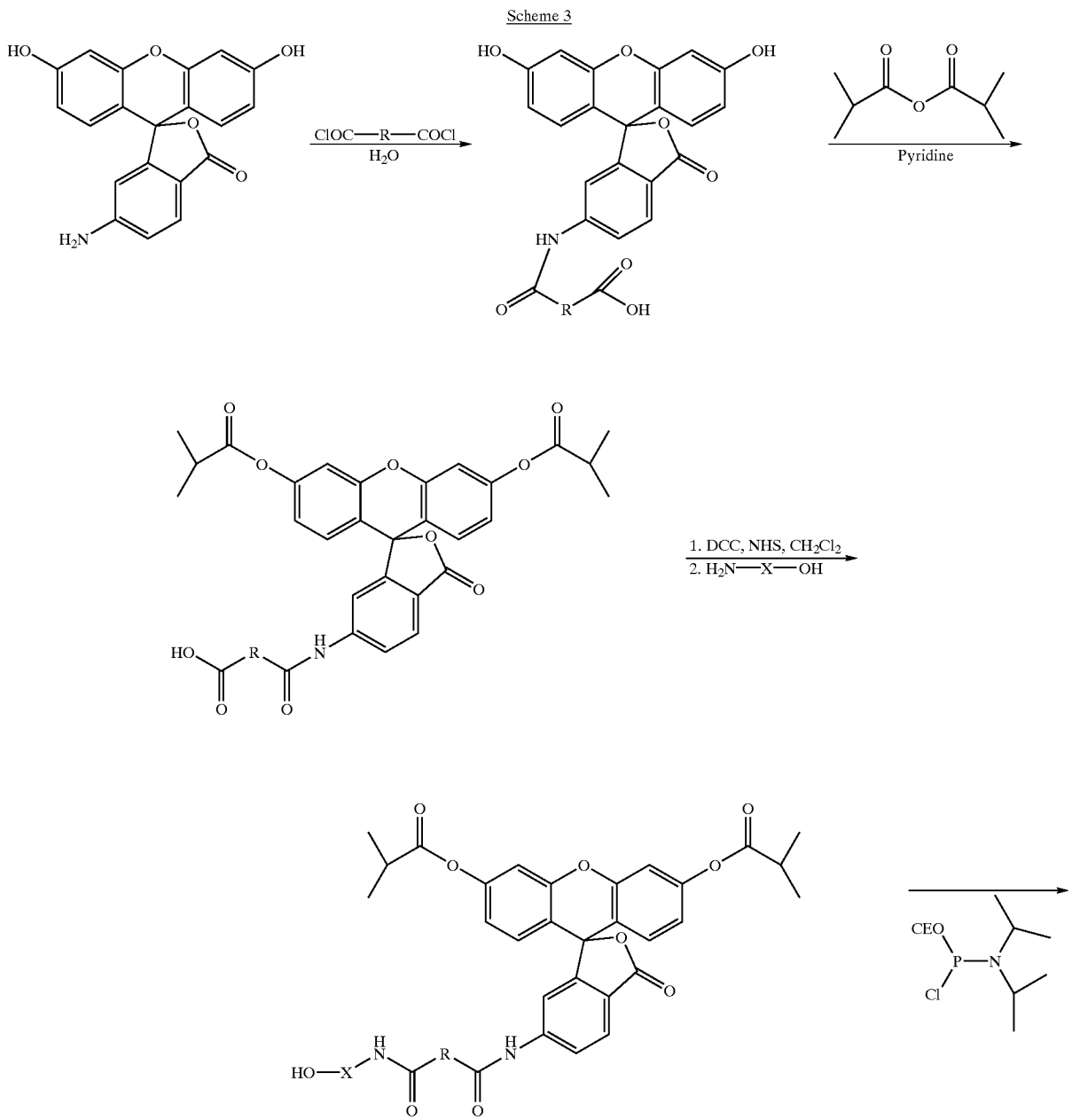

Scheme 3

R = commercial diacidchloride
X = commercial amino alcohol

TABLE 5
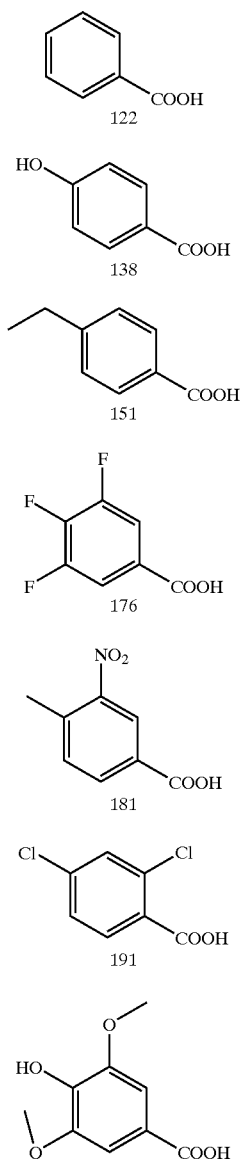
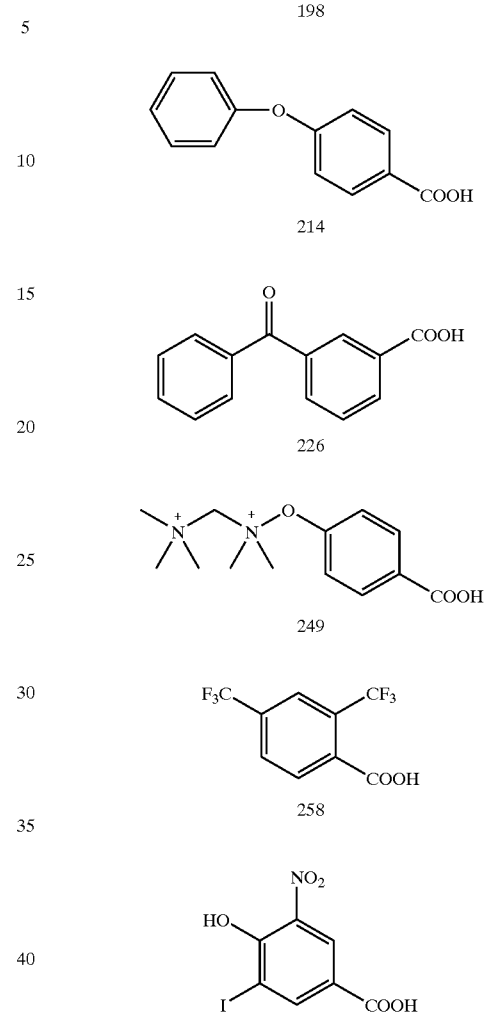
Benzoic acid derivatives as mass and charge modifiers. (Mass is written below each modifier)
TABLE 6
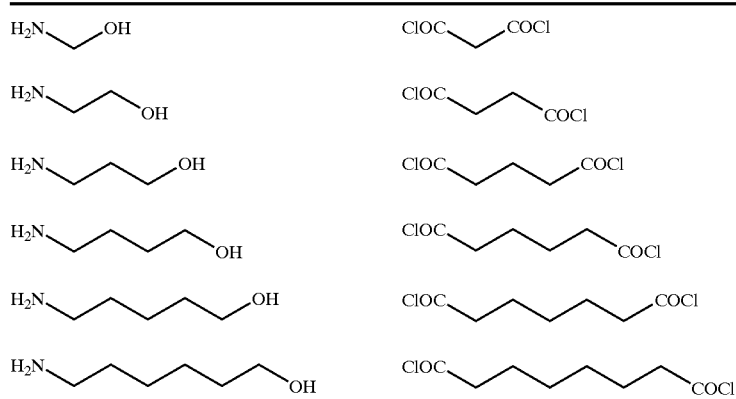

TABLE 6-continued

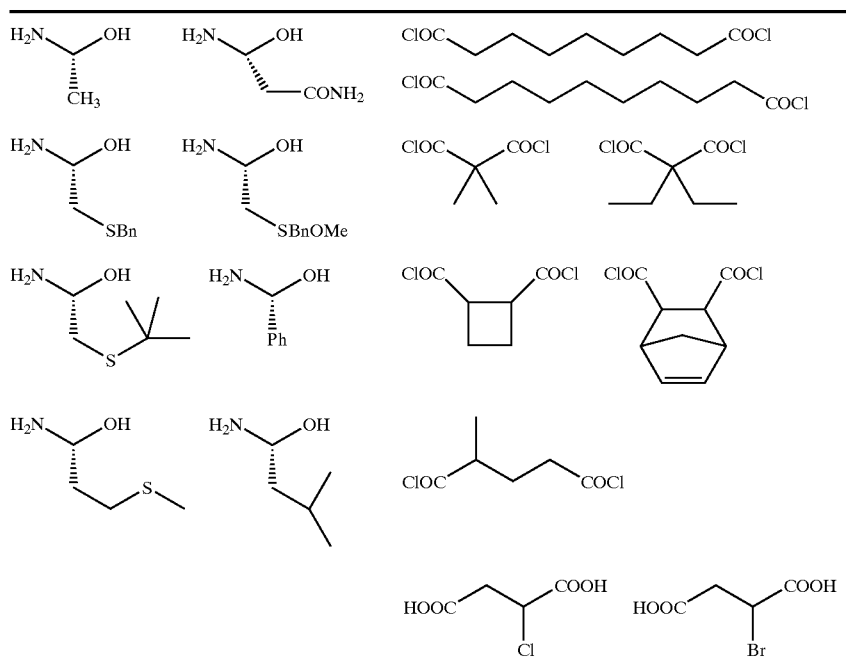

Mass and charge modifiers that can be used for conversion of amino dyes into e-tag phosphoramidite monomers.

A variety of maleimide derivatized e-tags have also been synthesized. These compounds were subsequently bioconjugated to 5'-thiol adorned DNA sequences and subjected to the 5'-nuclease assay. The species formed upon cleavage are depicted in Table 7.

TABLE 7

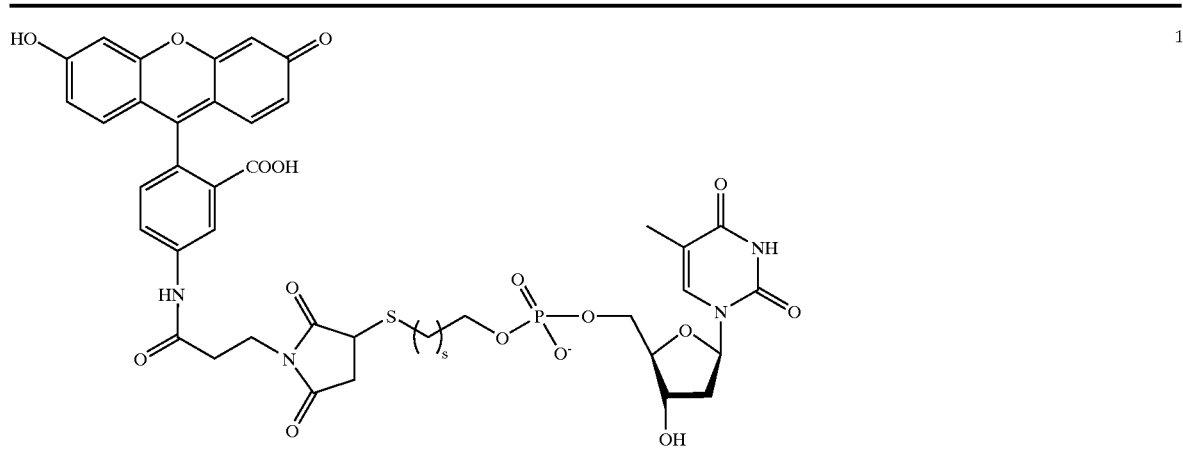

1

TABLE 7-continued
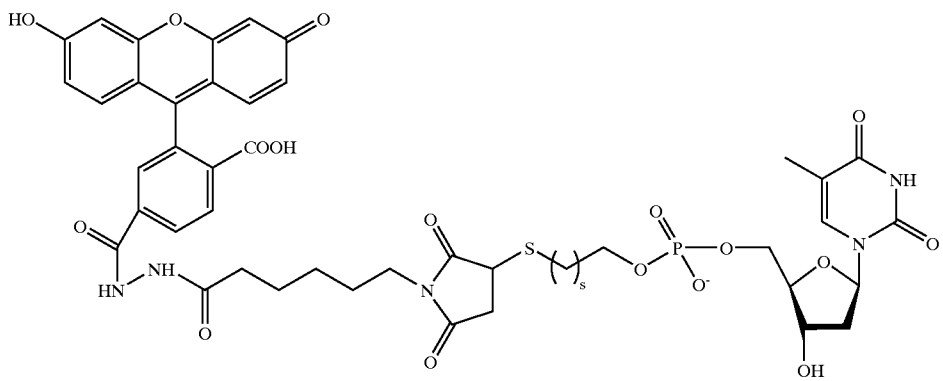
2
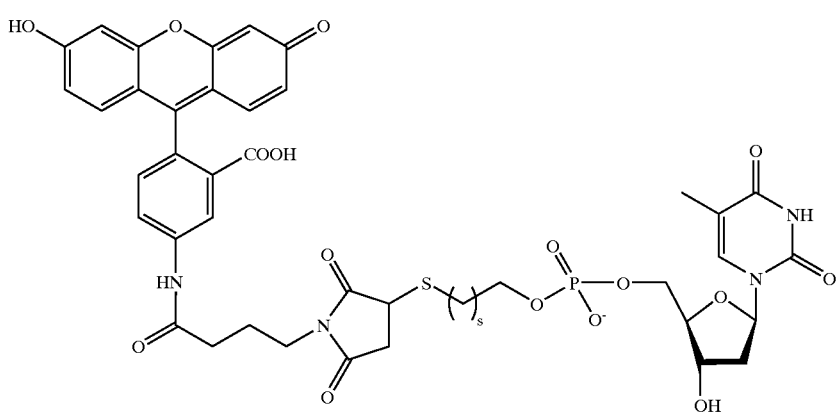
3
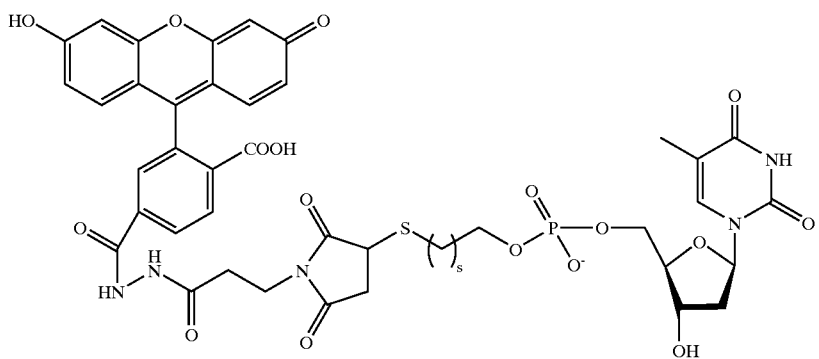
4
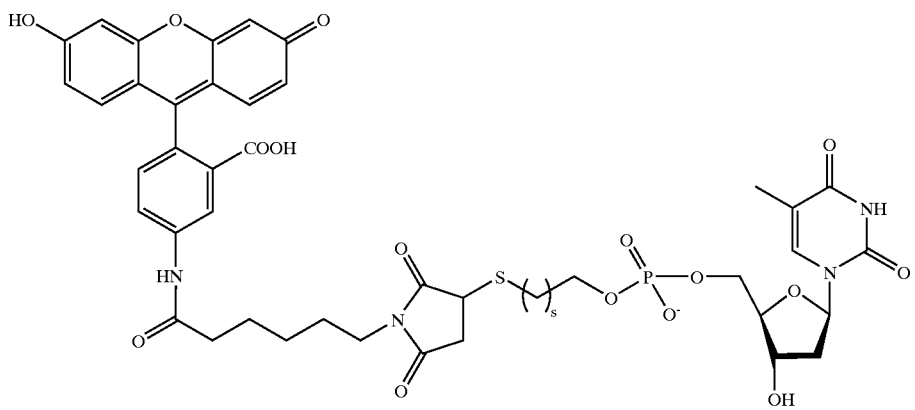
5

TABLE 7-continued
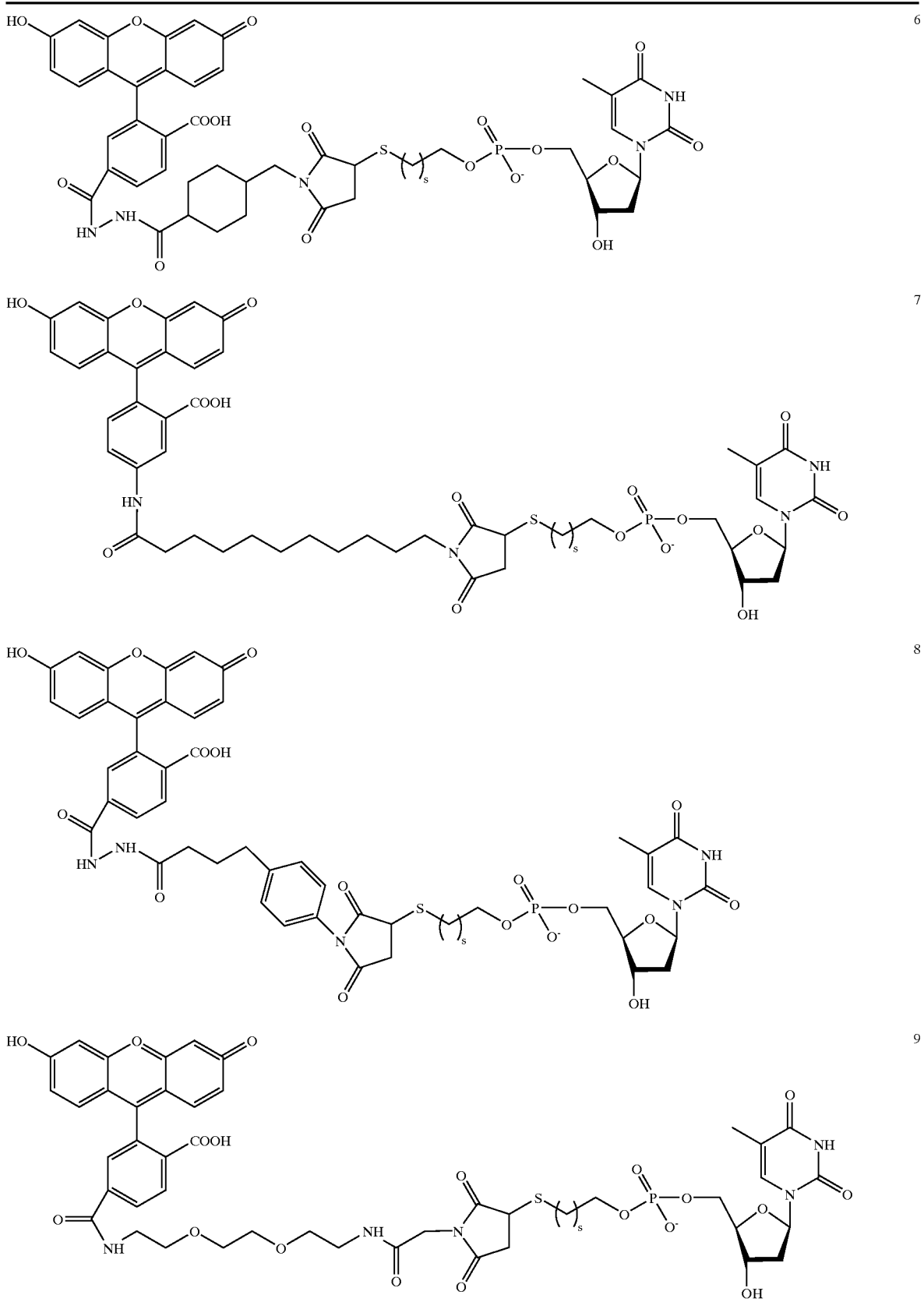

TABLE 7-continued

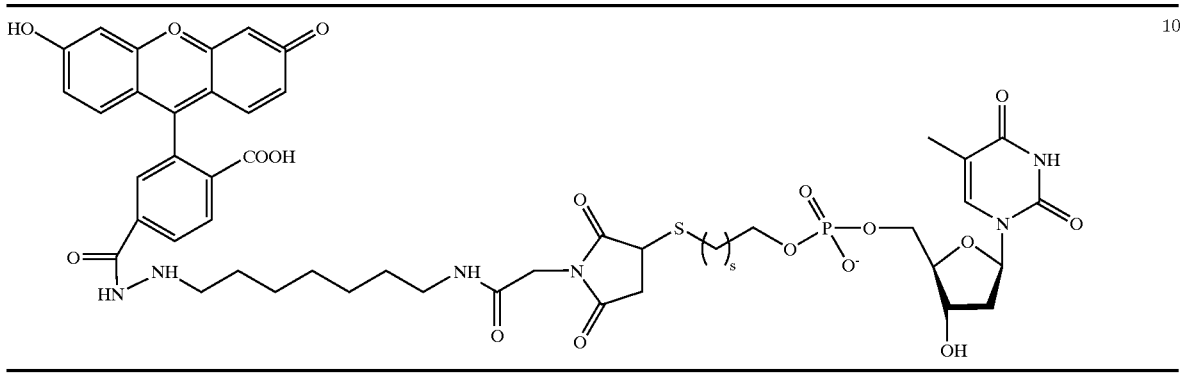

E-tags derived from maleimide linked precursors

As a matter of convenience, predetermined amounts of reagents employed in the present invention can be provided in a kit in packaged combination. A kit can comprise in packaged combination a target-binding region, e.g. oligonucleotide primer for each polynucleotide suspected of being in said set wherein each of said primers is hybridizable to a first sequence of a respective polynucleotide if present, a template dependent polynucleotide polymerase, nucleoside triphosphates, and a set of oligonucleotide snp detection sequences, each of said oligonucleotide probes having a fluorescent label at its 5'-end and having a sequence at its 5'-end that is hybridizable to a respective polynucleotide wherein each of said labels is cleavable from said oligonucleotide probe. Alternatively, the target-binding region may be an antibody for detecting ligands or enzyme substrate for detecting enzymes.

The kit may further comprise a device for conducting capillary electrophoresis. For nucleic acid determinations, the e-tag is releasable by a template dependent polynucleotide polymerase having 5' to 3' exonuclease activity. The kit can further include various buffered media, some of which may contain one or more of the above reagents.

The relative amounts of the various reagents in the kits can be varied widely to provide for concentrations of the reagents necessary to achieve the objects of the present invention. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit. The kits may also include a written description of a method in accordance with the present invention as described above.

In one embodiment of the kit, the e-tags are fluorescent conjugates represented by the formula:

R—L—T wherein R is a fluorescer, L is a mir, as described previously, and T is a functionality for binding to a nucleoside base, purine or pyrimidine, or a nucleoside base, a nucleoside, nucleotide or nucleotide triphosphates, or other member of the target-binding region.

In another embodiment of a kit, the e-tags are fluorescent conjugates represented by the formula:

R'—L'—T' wherein R' is a fluorescer, L' is a bond,, a combination of a neutral sub-region and a charged sub-region, an amino acid or a peptide or combinations of amino acids and thioacids or other carboxylic acids and T' is a nucleotide, nucleotide triphosphates or: functionality for binding to a member of the target-binding region.

In another embodiment of a kit, the e-tag is a fluorescent conjugate represented by the formula:

Fluorescer-L"-(amino acid)$_n$ wherein L" with (amino acid)$_n$ is a mir, where L" is a bond or a linking group of from 1 to 20 atoms in the chain and n is 1 to 100, usually 1 to 20, more usually 1 to 10.

The fluorescer may be fluorescein, the amino acid may be lysine and L" may be a bond in the form of an amide linkage involving the meta-carboxyl of the fluorescein and the terminal amine group of lysine.

In another embodiment of a kit in accordance with the invention, the e-tag is a label conjugate represented by the formula:

Fluorescein-(CO)NH—CH(CH$_2$)$_3$CH(NH$_2$)COX wherein X is selected from the group consisting of: OH, NH-lysine, NH-(lysine)$_2$, NH-alanine, NH-aspartic acid, NH-(aspartic acid)$_2$, NH-(aspartic acid)$_3$, NH-(aspartic acid)$_4$, NH-(aspartic acid)$_5$, NH-(aspartic acid)$_6$, NH-(aspartic acid)$_7$, NH-alanine-lysine, NH-aspartic acid-lysine, NH-(aspartic acid)$_2$-lysine, NH-(aspartic acid)$_3$-lysine, NH-(aspartic acid)$_4$-lysine, NH-(aspartic acid)$_5$-lysine, NH-(aspartic acid)$_6$-lysine, NH-(aspartic acid)$_7$-lysine, NH-(aspartic acid)$_8$-lysine, NH-(lysine)$_4$, and NH-(lysine)$_5$.

The kits will usually have at least about 5 different e-tags for conjugation, more usually at least about 10, frequently at least about 25 and may have 50 or more, usually not more than about 1,000. The e-tags will differ as to mobility, including mass/charge ratio and nature of charge, e.g. overall positive or negative, detectable moiety, e.g. fluorophore, electrochemical, etc, or functionality for linking a detectable moiety, e.g. maleimide, mercaptan, aldehyde, ketone, etc.

The e-tags described above may terminate in an appropriate functionality for linking to a nucleotide, nucleotide triphosphate or other molecule of interest or may terminate in such moieties.

The methodologies that may be employed involve heterogeneous and homogeneous techniques, where heterogeneous normally involves a separation step, where unbound label is separated from bound label, where homogeneous assays do not require, but may employ a separation step. One group of assays will involve nucleic acid detection, which includes sequence recognition, snp detection and scoring, transcription analysis, allele determinations, HLA determinations, or other determination associated with variations in sequence. The use of the determination may be forensic, mRNA determinations, mutation determinations, allele determinations, MHC determinations, haplotype determinations, single nucleotide polymorphism determinations, etc. The methodology may include assays dependent on 5'-nuclease activity, as in the use of the polymerase chain reaction or in Invader technology, 3'-nuclease activity, restriction enzymes and ribonuclease H, all of these methods involving catalytic cleavage of a phosphate linkage, where one to two oligonucleotides are bound to the target template. Alternatively, one may use channeling, where first and second agents are bound to first and second oligonucleotides, which bind proximally to the same target nucleic acid template. By having a label generating a mediator active in the cleavage of a bond present in the second agent to which an e-tag is linked, the e-tag will be released only when the two agents are proximally bound to the target template. The mediator may be physical, e.g. electromagnetic radiation or chemical, e.g. singlet oxygen or hydrogen peroxide. By providing for release of the agent to which the e-tag is bonded from the template, one can amplify the number of e-tags for a single target. Alternatively, one may have a plurality of e-tags that are bonded to the agent bound to the target, where binding to the target permits separation from e-tag labeled agent that is unbound. The e-tags bound to the target may then be released providing for a plurality of ;e-tags for a single target.

Instead of nucleic acid pairing, one may employ specific binding member pairing. There are a large number of specific binding pairs associated with receptors, such as antibodies, poly- and monoclonal, enzymes, surface membrane receptors, lectins, etc., and ligands for the receptors, which may be naturally occurring or synthetic molecules, protein or non-protein, such as drugs, hormones, enzymes, ligands, etc. The specific binding pair has many similarities to the binding of homologous nucleic acids, significant differences being that one normally cannot cycle between the target and the agent and one does not have convenient phosphate bonds to cleave. For heterogeneous assays, the binding of the specific binding pair is employed to separate the bound from the unbound e-tag bonded agents, while with homogeneous assays, the proximity of the specific binding pairs allow for release of the e-tags from the complex.

For an inclusive but not exclusive listing of the various manners in which the subject invention may be used, the following table is provided.

Recognition event leads to generation or modification of e-tags.

| Recognition Event | e-tag Activation | Amplification Mode | Format |
|---|---|---|---|
| Binding Assays (solution Phase e-tag generation followed by separation by CE, HPLC or Mass Spectra) | | | Multiplexed assays (2–1000) leading to release of library of e-tags. Every e-tag codes for a unique binding event or assay. |
| Hybridization followed by enzyme recognition | 5' Nuclease assay | PCR, Invader | Sequence recognition for example for multiplexed gene expression, SNP's scoring etc. . . |
| | 3' Nuclease assay | | Multiplexed assays Sequence recognition |
| | Restriction enzymes | | Multiplexed assays Sequence recognition |
| | Ribonuclease H | | Multiplexed assays Sequence recognition |
| Hybridization followed by channeling | Singlet Oxygen | Single e-tag release per binding event | Multiplexed assays Sequence recognition |
| Hybridization followed by channeling | Singlet Oxygen | Amplification due to turnover of e-tag binding moiety | Multiplexed assays Sequence recognition |
| | | Amplification due to release of multiple e-tags (10 to 100,000) per binding event | Multiplexed assays Sequence recognition |
| | Hydrogen peroxide | Amplification due to turnover of e-tag binding moiety | Multiplexed assays Sequence recognition |
| | | Amplification due to release of Multiple e-tags (10 to 100,000) per binding event | Multiplexed assays Sequence recognition |
| | Light; Energy Transfer | Amplification due to turnover (Photocleavage)of e-tag binding moiety | Multiplexed assays Sequence recognition |
| | | Amplification due to release of multiple e-tags (10 to 100,000) per binding event | Multiplexed assays Sequence recognition |
| IMMUNO-ASSYS Sandwich assays Antibody-1decoratedwith Sensitizerwhileantibody-2 Is decorated with singlet oxygen cleavable e-tags | Singlet Oxygen | A few (2–10) e-tags release per binding event | Proteomics Multiplexed Immunoassays |
| | Singlet Oxygen | Amplification due to release of multiple e-tags (10 to 100,000) per binding event | Proteomics Multiplexed Immunoassays |
| Sandwich assays | Hydrogen Peroxide | A few (2–10) e-tags release per | Proteomics |

-continued

| Recognition Event | e-tag Activation | Amplification Mode | Format |
|---|---|---|---|
| Antibody-1decoratedwith Glucoseoxidasewhileantibody-2 Is decorated with hydrogen peroxide cleavable e-tags | | binding event | Multiplexed Immunoassays |
| | Hydrogen Peroxide | Amplification due to release of multiple e-tags (10 to 100,000) per binding event | Proteomics Multiplexed Immunoassays |
| Competition assays Antibody-1decoratedwith Sensitizer while Antigen Is decorated with singlet oxygen cleavable e-tags | Singlet Oxygen | A few (2–10) e-tags release per binding event | |
| | Singlet Oxygen | Amplification due to release of multiple e-tags (10 to 100,000) per binding event | |
| Competition assays Antibody-1decoratedwith Glucoseoxidasewhileantigen Is decorated with hydrogen peroxide cleavable e-tags | | | |
| | Hydrogen Peroxide | A few (2–10) e-tags release per binding event | |
| | Hydrogen Peroxide | Amplification due to release of multiple e-tags (10 to 100,000) per binding event | |
| Binding Assays (Solid Phase e-tag generation followed by separation by CE, HPLC or Mass Spectra) | | | Multiplexed assays (2–1000) leading to release of library of e-tags. Every e-tag codes for a unique binding event or assay. |
| Hybridization Capture of Target on solid Surface. A number of e-tag labeled probes are hybridized to the target. Unhybridized e-tag labeled probes are removed. E-tag is released and separated and identified. | Light; Enzymes, Singlet oxygen, Hydrogen Peroxide Fluoride, Reducing agents, Mass Spectra Others | As an alternative to Branched chain assay; Digene's RNA:DNA duplex; High Sensitivity sequence identification assay. Amplification due to release of multiple e-tags (10 to 100,000) per binding event[3] | Sequence recognition for example for gene expression, SNP's scoring; Pathogen detection; etc. . . Can be carried out on Patches in Microfluidic channels. . . Integrated assay and separation device |
| Immunoassays Sandwich assays Antibody-1 is attached to a solid surface while antibody-2 is decorated with cleavable e-tags | Light; Enzymes, Singlet oxygen, Hydrogen Peroxide Fluoride, Reducing agents, Mass Spectra Others | A few (2–10) e-tags release per binding event Amplification due to release of multiple e-tags (10 to 100,000) per binding event | Proteomics Multiplexed Immunoassays Can be carried out on Patches in Microfluidic channels. . . Integrated assay and separation device |
| Competition assays Antibody-1 is attached to solid surface while Antigen Is decorated with cleavable e-tags | Light; Enzymes, Singlet oxygen, Hydrogen Peroxide Fluoride, Reducing agents, Mass Spectra Others | few (2–10) e-tags release per binding event Amplification due to release of multiple e-tags (10 to 100,00) per binding event | Proteomics Multiplexed Immunoassays Can be carried out on Patches in Microfluidic channels. . . Integrated assay and separation device |

As indicated in the table, for amplification one may use thermal cycling. The cleavage of the nucleic acid bound to the template results in a change in the melting temperature of the e-tag residue with release of the e-tag. By appropriate choice of the primer and/or protocol, one can retain the primer bound to the template and the e-tag containing sequence can be cleaved and released from the template to be replaced by an e-tag containing probe.

In determinations involving nucleic acids, since snp detection is, for the most part, the most stringent in its requirements, most of the description will be directed toward the multiplexed detection of snps. For other nucleic acid analyses, frequently the protocols will be substantially the same, although in some instances somewhat different protocols will be employed for snps, because of the greater demands snps make on fidelity. For proteins, the protocols will be substantially different and will be described independently of the snp protocols.

As exemplary of the subject invention, four target polynucleotides T1, T2, T3 and T4 are employed. Oligonucleotide primers PR1, PR2, PR3 and PR4 are employed, each respectively capable of hybridizing to a sequence in the respective target polynucleotides. Also employed are four oligonucleotide snp detection sequences, PB1, PB2, PB3 and PB4. Each of the snp detection sequences comprises a fluorescent label F1, F2, F3 and F4, respectively. In this example, there is a mismatch between PB2 and T2, which comprises a single nucleotide polymorphism. The reaction medium comprising the above reagents and nucleoside triphosphates and a template: dependent polynucleotide polymerase having 5' to 3' exonuclease activity is treated under amplification conditions. Primers PR1, PR2, PR3 and PR4 hybridize to their respective target polynucleotides and are extended to yield extended primers EPR1, EPR2, EPR3 and EPR4. snp detection sequences PB1, PB3 and PB4, which hybridize with their respective target polynucleotides, are acted upon by the exonuclease to cleave a single nucleotide bearing the respective fluorescent label. PB2, which does not bind to the target polynucleotide, is not cleaved. Cleaved fragments F1, F3 and F4 are injected into a separation channel in a chip for conducting electroseparation. The labels are identified by their specific mobility and fluorescence upon irradiation. The separated labels are related to the presence and amount of the respective target polynucleotide.

One, usually a plurality, of snp's, is simultaneously determined by combining target DNA with one or a plurality, respectively, of reagent pairs under conditions of primer extension. Each pair of reagents includes a primer which binds to target DNA and a snp detection sequence, normally labeled, which binds to the site of the snp and has an e-tag, usually at its 5'-end and the base complementary to the snp, usually at other than a terminus of the snp detection sequence. The conditions of primer extension employ a polymerase having 5'-3' exonuclease activity, dNTP's and auxiliary reagents to permit efficient primer extension. The primer extension is performed, whereby detector sequences bound to the target DNA are degraded with release of the e-tag. By having each snp associated with its own e-tag, one can determine the snp's, which are present in the target DNA for which pairs of reagents have been provided.

The pairs of reagents are DNA sequences, which are related to a snp site. The primer binds to the target DNA upstream from the snp site in the direction of extension. The labeled detector sequence binds downstream from the primer in the direction of extension and binds to a sequence, which includes the snp. The primer sequence will usually be at least about 12 bases long, more usually at least 18 bases long and usually fewer than 100 bases, and more usually fewer than 60 bases. The primer will be chosen to bind substantially uniquely to a target sequence under the conditions of primer extension, so that the sequence will normally be one that is conserved or the primer is long enough to bind in the presence of a few mismatches, usually fewer than about 10 number % mismatches. By knowing the sequence, which is upstream from the snp of interest, one may select a sequence, which has a high G-C ratio, so as to have a high binding affinity for the target sequence. In addition, the primer should bind reasonably close to the snp, usually not more than about 200 bases away, more usually not more than about 100 bases away, and preferably within about 50 bases. Since the farther away the primer is from the snp, the greater amount of dNTP's, which will be expended, there will usually be no advantage in having a significant distance between the primer and the snp detection sequence. Generally, the primer will be at least about 5 bases away from the snp.

The number of reagent pairs may be varied widely, from a single pair to two or more pairs, usually at least about 5 pairs, more usually at least about 9 pairs and may be pairs or more. By virtue of the use of different e-tags, which have different mobilities and are readily resolvable under conventional capillary electrophoretic conditions, the subject pairs may be used to perform multiplexed operations in a single vessel, where a family of snps may be identified. Usually, the total, number of different reagent pairs or different target sequences in a single determination will be under 200, more usually under 100 and in many cases will not exceed 50.

In one snp determination protocol, the primer includes the complementary base of the snp. This protocol is referred to as "Invader" technology and is described in U.S. Pat. No. 6,001,567. The protocol involves providing: (a) (i) a cleavage means, which is normally an enzyme, referred to as a cleavase, that recognizes a triplex consisting of the target sequence, a primer which binds to the target sequence and terminates at the snp position and a labeled probe that binds immediately adjacent to the primer and is. displaced from the target at the snp position, when a snp is present; the cleavase clips the labeled probe at the site of displacement, releasing the label; ii) a source of target nucleic acid, the target nucleic acid having a first region, a second region and a third region, wherein the first region is downstream from the second region and the second region is contiguous to and downstream from the third region; and (iii) first and second oligonucleotides having 3' and 5' portions, wherein the 3' portion of the first oligonucleotide contains a sequence complementary to the third region of the target nucleic acid and the 5' portion of the first oligonucleotide and the 3' portion of the second oligonucleotide each contain sequences usually fully complementary to the second region of the target nucleic acid, and the 5' portion of the second oligonucleotide contains sequence complementary to the first region of said target nucleic acid; (b) mixing, in any order, the cleavage means, the target nucleic acid, and the first and second oligonucleotides under hybridization conditions that at least the 3' portion of the first oligonucleotide is annealed to the target nucleic acid and at least the 5' portion of the second oligonucleotide is annealed to any target nucleic acid to from a cleavage structure, where the combined melting temperature of the complementary regions within the 5' and 3' portions of the first oligonucleotide when annealed to the target nucleic acid is greater than the melting temperature of the 3' portion of the first oligonucleotide and cleavage of the cleavage structure occurs to generate labeled products; and (c) detecting the labeled cleavage products.

Thus, in an Invader assay attachment of an e-tag to the 5' end of the detector sequence results in the formation of e-tag labeled nucleotide when target sequence is present. The e-tag labeled nucleotide is separated and detected. By having a different e-tag for each nucleic acid sequence of interest, having a different electrophoretic mobility, which may require further treatment depending on the total number of snp's or target sequences to be detected, one can readily determine the snp's or measure multiple sequences, which are present in a sample.

In another snp detection protocol, an alternative method of cleavage is used and various detectable tags may be employed, the most common using a fluorescent label. The difference in protocol between a fluorescent label and another type of label, such as an electrochemical label, is the method of detection. Otherwise, the protocols will be substantially the same. The tagged snp detection sequence will be chosen to bind to the target sequence comprising the snp. The length of the snp detector sequence is in part related to the length and binding affinity of the primer. The two sequences act together to ensure that the pair of reagents bind to the proper target sequence. The greater the fidelity of binding of one member of the pair, the less fidelity that is required for the other member of the pair. Since the observed signal will be dependent upon both members of the pair being present, each member serves as a check on the other member for production of the signal. However, since except for the cost, it is relatively easy to make reasonably long oligonucleotides, usually both members of the pair will provide for unique binding to their respective target sequences. Therefore, the length of the snp detector sequence will come within the parameters indicated for the primer, but the total number of bases for the two pair members will usually be at least 36, more usually at least about 40.

Each snp detection sequence will have at least one nucleotide modified with an e-tag, which is labeled, which is fluorescent or can be subsequently made fluorescent, or can be detected electrochemically or by other convenient detection methodologies. Usually, the modified nucleotide will be at the 5'-end of the sequence, but the modified nucleotide may be anywhere in the sequence, particularly where there is a single nuclease susceptible linkage in the detection sequence. Since the determination is based on the at least partial degradation of the snp detector sequence, having the modified nucleotide at the end ensures that if degradation occurs, the e-tag will be released. Since nucleases may clip at other than the terminal phosphate link, it is desirable to prevent cleavage at other than the terminal phosphate link. In this way one avoids the confusion of having the same e-tag joined to different numbers of nucleotides after cleavage. Cleavage at the terminal phosphate can be relatively assured by using a linker at the penultimate nucleoside, which is not cleaved by the nuclease, more particularly having only the ultimate linkage susceptible to hydrolysis by a nuclease. For example, one may use a thiophosphate, phosphinate, phosphoramidate, or a linker other than a phosphorous acid derivative, such as an amide, boronate, or the like. The particular hydrolase resistive linker will be primarily one of synthetic convenience, so long as degradation of the binding affinity is not sacrificed. If desired all of the linkers other than the ultimate linker may be resistant to nuclease hydrolysis.

If desired, the snp detection sequence may have a combination of a quencher and a fluorescer. In this instance the fluorescer would be in proximity to the nucleoside to which the linker is bonded, as well as the quencher, so that in the primer extension mixture, fluorescence from fluorescer bound to the snp detection sequence would be quenched. As the reaction proceeds and fluorescer is released from the snp detection sequence and, therefore, removed from the quencher, it would then be capable of fluorescence. By monitoring the primer extension mixture for fluorescence, one would be able to determine when there would probably be a sufficient amount of individual e-tags to provide a detectable signal for analysis. In this way, one could save time and reagent by terminating the primer extension reaction at the appropriate time. There are many quenchers that are not fluorescers, so as to minimize fluorescent background from the snp detection sequence. Alternatively, one could take small aliquots and monitor the reaction for observable e-tags.

The snp detection sequence may be further modified to improve separation and detection of the e-tags. By virtue of the difference in mobility of the e-tags, the snp detection sequences will also have different mobilities. Furthermore, these molecules will be present in much larger amounts than the released e-tags, so that they may obscure detection of the released e-tags. Also, it is desirable to have negatively charged snp detection sequence molecules, since they provide for higher enzymatic activity and decrease capillary wall interaction. Therefore, by providing that the intact snp detection sequence molecule can be modified with a positively charged moiety, but not the released e-tag, one can change the electrostatic nature of the snp detection sequence molecules during the separation. By providing for a ligand on the snp detection sequence molecule to which a positively charged molecule can bind, one need only add the positively charged molecule to change the electrostatic nature of the snp detection sequence molecule. Conveniently, one will usually haven a ligand of under about 1 kDal. This may be exemplified by the use of biotin as the ligand and avidin, which is highly positively :charged, as the receptor/positively charged molecule. Instead of biotin/avidin, one may have other pairs, where the receptor, e.g. antibody, is naturally positively charged or is made so by conjugation with one or more positively charged entities, such as arginine, lysine or histidine, ammonium, etc. The presence of the positively charged moiety has many advantages in substantially removing the snp detection sequence molecules from the electropherogram. In carrying out the process, the positively charged moiety is added at or after the completion of the digestion.

If desired, the receptor may be used to physically sequester the molecules to which it binds, removing entirely intact e-tags containing the target-binding region or modified target-binding regions retaining the ligand. These modified target-binding regions may be as a result of degradation of the starting material, contaminants during the preparation, aberrant cleavage, etc. or other nonspecific degradation products of the target binding sequence. As above, a ligand, exemplified by biotin, is attached to the target-binding region, e.g. the penultimate nucleoside, so as to be separated from the e-tag upon cleavage. After the 5' nuclease assay, a receptor for the ligand, for biotin exemplified by strept/avidin (hereafter "avidin") is added to the assay mixture. Other receptors include natural or synthetic receptors, such as immunoglobulins, lectins, enzymes, etc. Desirably, the receptor is positively charged, naturally as in the case of avidin, or is made so, by the addition of a positively charged moiety or moieties, such as ammonium groups, basic amino acids, etc. Avidin binds to the biotin attached to the detection probe and its degradation products. Avidin is positively charged, while the cleaved e-tag is negatively charged. Thus the separation of the cleaved e-tag from, not only uncleaved probe, but also its degradation products, is easily achieved by using conventional separation methods. Alternatively, the receptor may be bound to a solid support or high molecular weight macromolecule, such as a vessel wall, particles, e.g. magnetic particles, cellulose, agarose; etc., and separated by physical separation or centrifugation, dialysis, etc. This method further enhances the specificity of the assay and allows for a higher degree of multiplexing.

While the ligand may be present at a position other than the penultimate position,, and one may make the ultimate linkage nuclease resistant, so that cleavage is directed to the penultimate linkage, this will not be as efficient as having cleavage at the ultimate linkage. The efficiency would be even worse where the ligand is at a more distant nucleotide from the e-tag. Therefore, while such protocols are feasible, and may be used, they will not be preferred.

As a general matter, one may have two ligands, if the nature of the target-binding region permits. As describedabove, one ligand can be used for sequestering e-tags bound to target-binding region retaining the first ligand from products lacking the first ligand. Isolation and concentration of the e-tags bound to a modified target-binding region lacking the first ligand would then be performed. In using the two ligands, one would first combine the reaction mixture with a first receptor for the first ligand for removing target-binding region retaining the first ligand. One could either separate the first receptor from the composition or the first receptor would be retained in the composition, as described. This would be followed by combining the resulting composition, where the target-binding region containing the first ligand is bound to the first receptor, with the second receptor, which would serve to isolate or enrich for modified target-binding region lacking the first ligand, but retaining the second ligand. The second ligand could be the detectable label; a small molecule for which a receptor is available, e.g. a hapten, or a portion of the e-tag could serve as the second ligand. After the product is isolated or enriched, the e-tag could be released by denaturation of the receptor, displacement of the product, high salt concentrations and/or organic solvents, etc.

For e-tags associated with nucleic acids sequences, improvements include employing a blocking linkage between nucleotides in the sequence, particularly at least one of the links between the second to fourth nucleotides to inhibit cleavage at this or subsequent sites, and using control sequences for quantitation. Further improvements in the e-tags provide for having a positively multicharged moiety joined to the e-tag probe during separation.

The above three methods are generally applicable not only to generating a single e-tag per sequence detected but also to generation of a single oligonucleotide fragment for fragment separation and identification by electrophoresis or by mass spectra as it is essential to get one fragment per sequence detected. For purpose of explanation, these methods are illustrated below.

1.
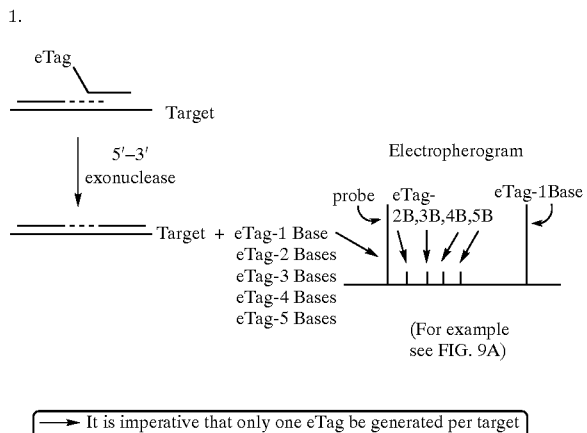
2. Depurination results in degradation of signal probes.
3. Signal probe is also degraded by the enzyme (5'–3' nuclease activity).
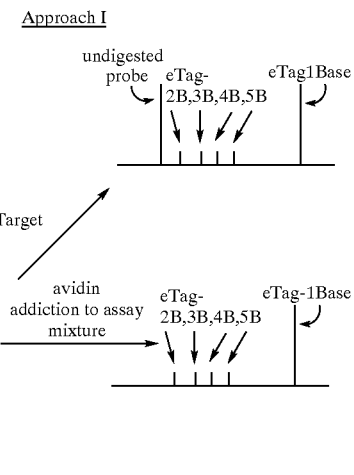
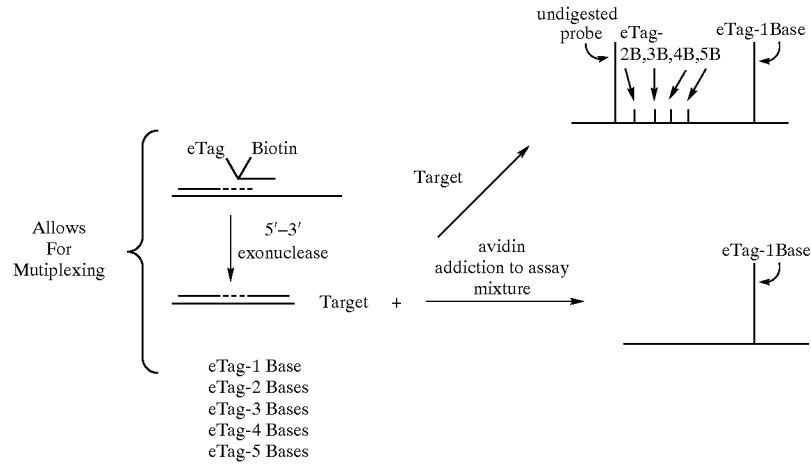

Approach III

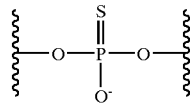
Nuclease resistant modifications to backbone.
Ex. Phosphorothioates.

The complementary base to the snp may be anywhere in the detector sequence, desirably at other than the terminal nucleoside to enhance the fidelity of binding. The snp detector sequence will be designed to include adjacent nucleotides, which provide the desired affinity for the hybridization conditions. The snp detection sequence may be synthesized by any convenient means, such as described in Matthews, et al., Anal Biochem. (1988) 169:1–25; Keller, et al., "DNA Probes," $2^{nd}$ edition (1993) Stockton Press, New York, N.Y.; and Wetmur, Critical Reviews in Biochemistry and Molecular Biology (1991) 26:227–259.

The extension reaction is performed by bringing together the necessary combination of reagents and subjecting the mixture to conditions for carrying out the desired primer extension. Such conditions depend on the nature of the extension, e.g., PCR, single primer amplification, LCR, NASBA, 3SR and so forth, where the enzyme which is used for the extension has 5'-3' nuclease activity. The extension reaction may be carried out as to both strands or as to only a single strand. Where pairs of primer and snp detection sequence are used for both strands, conveniently, the e-tag will be the same, but the bases will be different. In this situation, one may wish to have a cleavable linkage to the base, so that for the same snp, one would obtain the same e-tag. Alternatively, if the number of snps to be determined is not too high, one could use different e-tags for each of the strands. Usually, the reaction will be carried out by using amplifying conditions, so as to provide an amplified signal for each snp. Amplification conditions normally employ thermal cycling, where after the primer extension and release of e-tags associated with snps which are present, the mixture is heated to denature the double-stranded DNA, cooled, where the primer and snp detection sequence can rehybridize and the extension repeated.

Depending on the protocol, the e-tags or e-tag, will be separated from a portion or substantially all of the detection sequence, usually retaining not more than about 3 nucleotides, more usually not more than about 2 nucleotides and preferably from 0 to 1 nucleotide. By having a cleavable linker between the e-tag and the detection sequence, the e-tag may be freed of all the nucleotides. By having a nuclease resistant penultimate link, a single nucleotide may be bonded to the e-tag.

Reagents for conducting the primer extension are substantially the same reaction materials for carrying out an amplification, such as an amplification indicated above. The nature and amounts of these reagents are dependent on the type of amplification conducted. In addition to oligonucleotide primers the reagents also comprise nucleoside triphosphates and a nucleotide polymerase having 5'-3' nuclease activity.

The nucleoside triphosphates employed as reagents in an amplification reaction include deoxyribonucleoside triphosphates such as the four common deoxyribonucleoside triphosphates dATP, dCTP, dGTP and dTTP. The term "nucleoside triphosphates" also includes derivatives and analogs thereof, which are exemplified by those derivatives that are recognized and polymerized in a similar manner to the underivatized nucleoside triphosphates.

The nucleotide polymerase employed is a catalyst, usually an enzyme, for forming an extension of an oligonucleotide primer along a polynucleotide such as a DNA template, where the extension is complementary thereto. The nucleotide polymerase is a template dependent polynucleotide polymerase and utilizes nucleoside triphosphates as building blocks for extending the 3'-end of a polynucleotide to provide a sequence complementary with the polynucleotide template. Usually, the catalysts are enzymes, such as DNA polymerases, for example, prokaryotic DNA polymerase (I, II, or III), T4 DNA polymerase, T7 DNA polymerase, Vent DNA polymerase, Pfu DNA polymerase, Taq DNA polymerase, and the like. Polymerase enzymes may be derived from any source, such as eukaryotic or prokaryotic cells, bacteria such as E. coli, plants, animals, virus, thermophilic bacteria, genetically modified enzymes, and so forth.

The conditions for the various amplification procedures are well known to those skilled in the art. In a number of amplification procedures, thermal cycling conditions as discussed above are employed to amplify the polynucleotides. The combination of reagents is subjected to conditions under which the oligonucleotide primer hybridizes to the priming sequence of, and is extended along, the corresponding polynucleotide. The exact temperatures can be varied depending on the salt concentration, pH, solvents used, length of and composition of the target polynucleotide sequence and the oligonucleotide primers.

Thermal cycling conditions are employed for conducting an amplification involving temperature or thermal cycling and primer extension, such as in PCR or single primer amplification, and the like. The pH and the temperature are selected so as to cause, either simultaneously or sequentially, dissociation of any internally hybridized sequences, hybridization or annealing of the oligonucleotide primer and the snp detection sequence with the target polynucleotide sequence, extension of the primer, release of the e-tag from snp detection sequence bound to the target polynucleotide sequence and dissociation of the extended primer. This usually involves cycling the reaction medium between two or more temperatures. In conducting such a method, the medium is cycled between two to three temperatures. The temperatures for thermal cycling generally range from about 50° C. to 100° C., more usually, from about 60° C. to 95° C. Relatively low temperatures of from about 30° C. to about 65° C. can be employed for the extension steps, while denaturation and hybridization can be carried out at a temperature of from about 50° C. to about 105° C. The reaction medium is initially at about 20° C. to about 45° C., preferably, about 25° C. to about 35° C. Relatively low temperatures of from about 50° C. to about 80° C., preferably, 50° C. to about 60° C., are employed for the hybridization or annealing steps, while denaturation is carried out at a temperature of from about 80° C. to about 100° C., preferably, 90° C. to about 95° C., and extension is carried out at a temperature of from about 70° C. to about 80° C., usually about 72° C. to about 74° C. The duration of each cycle may vary and is usually about 1 to 120 seconds, preferably, about 5 to 60 seconds for the denaturation steps, and usually about 1 to 15 seconds, preferably, about 1 to 5 seconds, for the extension steps. It is to be understood that the actual temperature and duration of the cycles employed are dependent on the particular amplification conducted and are well within the knowledge of those skilled in the art.

Generally, an aqueous medium is employed. Other polar cosolvents may also be employed, usually oxygenated organic solvents of from 1–6, more usually from 1–4, carbon atoms, including alcohols, ethers, formamide and the like. Usually, these cosolvents, if used, are present in less than about 70 weight percent, more usually in less than about 30 weight percent.

The pH for the medium is usually in the range of about 4.5 to 9.5, more usually in the-:range of about 5.5 to 8.5, and preferably in the range of about 6 to 8. Various buffers may be used to achieve the desired pH and maintain the pH during the determination. Illustrative buffers include borate, phosphate, carbonate; Tris, barbital and the like. The particular buffer employed is not critical to this invention but in individual methods one buffer may be preferred over another. The medium may also contain materials required for enzyme activity such as a divalent metal ion (usually magnesium).

The selection of the snp detection sequence will affect the stringency employed during the primer extension, particularly at the stage of hybridization. Since in a substantial number of samples, the DNA will be heterozygous for snps, rather than homozygous, one does not wish to have false positives, where the snp detection sequence may bond to the sequence comprising the prevalent nucleotide, as well as the sequence comprising the snp. Where the DNA sample is homozygous for the prevalent sequence, it is also important that the snp detection sequence does not bind to give a false positive. Therefore, the difference in $T_m$ between the snp containing sequence and the wild-type sequence will usually be at least about 3° C., more usually at least about 5° C., under the conditions of the primer extension.

Various ancillary materials will frequently be employed in the methods in accordance with the present invention. For example, in addition to buffers and salts, the medium may also comprise stabilizers for the medium and the reaction components. Frequently, the medium may also include proteins such as albumins, quaternary ammonium salts, polycations such as spermine, surfactants, particularly non-ionic surfactants, binding enhancers, e.g., polyalkylene glycols, or the like.

The reaction is conducted for a time sufficient to produce the desired number of copies of each of the polynucleotides suspected of being present as discussed below. Generally, the time period for conducting the entire method will be from about 10 to 200 minutes. As mentioned above, it is usually desirable to minimize the time period.

The concentration of the nucleotide polymerase is usually determined empirically. Preferably, a concentration is used that is sufficient such that the amplification is robust. The primary limiting factor generally is the cost of the reagent. Such enzymes include Pfu DNA polymerase (native and recombinant) from Stratagene, La Jolla, Calif., Ultma DNA polymerase from Perkin Elmer, Foster City, Calif., rBst DNA polymerase from Epicentre Technologies, Madison, Wis., VENT DNA polymerase from New England Biolabs, Beverly, Mass., Tli DNA polymerase from Promega Corp., Madison, Wis., and Pwo DNA polymerase from Boehringer Mannheim, Indianapolis; Ind., and the like.

The initial concentration of each of the polynucleotides containing the respective target snps can be as low as about 50 pg/ml in a sample. After amplification the concentration of each polynucleotide should be at least about 10 picomolar, generally in the range of about 10 pM to about 10 nM, usually from about 10 to $10^{10}$, more usually from about $10^3$ to $10^8$ molecules in a sample preferably at least $10^{-21}$M in the sample and may be $10^{10}$ to $10^{-19}$M, more usually $10^{-14}$ to $10^{-19}$M. In general, the reagents for the reaction are provided in amounts to achieve extension of the oligonucleotide primers.

The concentration of the oligonucleotide primer(s) will be about 1 to about 20 $\mu$M and is usually about 1 to about 10 $\mu$M, preferably, about 1 to about 4 $\mu$M, for a sample size that is about 10fM. Preferably, the concentration of the oligonucleotide primer(s) is substantially in excess over, preferably at least about $10^7$ to about $10^{10}$ times greater than, more preferably, at least about $10^9$ times greater than, the concentration of the corresponding target polynucleotides.

The amount of the oligonucleotide probes will be 10 to about 50 nM and is usually about 50 to about 200 nM for a sample size that is about 10 fM (10 fg/$\mu$l). Preferably, the concentration of the oligonucleotide probes is substantially in excess over, preferably at least about $10^7$ times greater than, more preferably, at least about $10^8$ times greater than, the concentration of each of the target polynucleotides.

The concentration of the nucleoside triphosphates in the medium can vary widely; preferably, these reagents are present in an excess amount. The nucleoside triphosphates are usually present in about 100 M to about 1 mM, preferably, about 20 to about 400 M.

The order of combining of the various reagents to form the combination may vary. Usually, the sample containing the polynucleotides is combined with a pre-prepared combination of nucleoside triphosphates and nucleotide polymerase. The oligonucleotide primers and the snp detection sequences may be included in the prepared combination or may be added subsequently. However, simultaneous addition of all of the above, as well as other step-wise or sequential orders of addition, may be employed provided that all of the reagents described above are combined prior to the start of the reactions. The oligonucleotide pairs may be added to the combination of the reagents at or prior to the initiation of the primer extension reaction and may be replenished from tine-to-time during the primer extension reaction.

For quantitation, one may choose to use controls, which provide a signal in relation to the amount of the target that is present or is introduced. Where one is dealing with a mixture of nucleic acid molecules, as in the case of mRNA in a lysate, one may use the known amounts of one or more different mRNAs in the particular cell types as the standards. Desirably, one would have at least two controls, preferably at least 3 controls, where the variation in number between any two controls is at least about $10^2$, and the total range is at least about $10^3$, usually at least about $10^4$. However, determining the consistent ratio of mRNAs occurring naturally will result in a large margin of error, so that one would usually rely on synthetic targets. Where a control system is added for quantitation, as compared to relying on the presence of a known amount of a plurality of endogenous nucleic acids, the control system will comprise at least two control sequences, usually at least 3 control sequences and generally not more than about 6 control sequences, where the upper limit is primarily one of convenience and economy, since additional control sequences will usually not add significant additional precision which will usually be at least about 50 nucleotides, more usually at least about 100 nucleotides. The control sequences will have a common primer sequence and different control detection sequences, which are intended to parallel the primer sequence and snp detection sequence in size, spacing and response to the primer extension conditions. In carrying out the primer extension reaction with sample nucleic acid, one would then add different number of molecules of the different control sequences, so that one could graph the result to give a signal/number relationship. This graph could then be used to relate signals observed with target molecules to the number of molecules present.

After completion of the primer extension reaction, either by monitoring the change in fluorescence as described above or taking aliquots and assaying for total free e-tags, the mixture may now be analyzed. Depending on the instrument, today from one to four different fluorescers activated by the same light source and emitting at different detectable labels may be used. With improvements, five or more different fluorescers will be available, where an additional light source may be required. Electrochemical detection is described in U.S. Pat. No. 6,045,676.

The subject assays are predicated on having a reagent that has a high affinity for a reciprocal binding member, the analyte. Usually, the binding affinity will be at least about $10^{-7}M^{-1}$, more usually, at least about $10^{-8}M^{-1}$. For the most part, the reagents will be receptors, which includes antibodies, IgA, IgD, IgG, IgE and IgM and subtypes thereof, enzymes, lectins, nucleic acids, nucleic acid binding proteins, or any other molecule that provides the desired specificity for the analyte in the assay, one of the members normally being a protein. The antibodies may be polyclonal or monoclonal or mixtures of monoclonal antibodies depending on the nature of the target composition and the targets. The targets or analytes may be any molecule, such as small organic molecules of from about 100 to 2500 Dal, poly(amino acids) including peptides of from about 3 to 100 amino acids and proteins of from about 100 to 50,000 or more amino acids, saccharides, lipids, nucleic acids, etc., where the analytes may be part of a larger assemblage, such as a cell, microsome, organelle, virus, protein complex, chromosome or fragment thereof, nucleosome, etc.

In addition, the subject heterogeneous assays require that the unbound labeled reagent be separable from the bound labeled reagent. This can be achieved in a variety of ways. Each way requires that a reagent that distinguishes between the complex of labeled reagent and target be bound to a solid support. The solid support may be a vessel wall, e.g. microtiter well plate well, capillary, plate, slide, beads, including magnetic beads, liposomes, or the like. The primary characteristics of the solid support is that it permits segregation of the bound labeled specific binding member from unbound and does not interfere with the formation of the binding complex, nor the other operations of the determination.

The solid support may have the complex directly bound to the support or indirectly bound. For directly bound one may have the binding member covalently or non-covalently bound to the support. For proteins, many surfaces provide non-diffusible binding of a protein to the support, so that one adds the protein to the support and allows the protein to bind, washes away weakly bound protein and then adds an innocuous protein to coat any actively binding areas that are still available. The surface may be activated with various functionalities that will form covalent bonds with a binding member. These groups may include imino halides, activated carboxyl groups, e.g. mixed anhydrides or acyl halides, amino groups, α-halo or pseudohaloketones, etc. The specific binding member bound to the surface of the support may be any molecule which permits the binding portion of the molecule, e.g. epitope, to be available for binding by the reciprocal member. Where the binding member is polyepitopic, e.g. proteins, this is usually less of a problem, since the protein will be polyepitopic and even with random binding of the protein to the surface, the desired epitope will be available for most of the bound molecules. For smaller molecules, particularly under 5 kDal, one will usually have an active functionality on the specific binding member that preserves the binding site, where the active functionality reacts with a functionality on the surface of the support. The same functionalities described above may find use. Conveniently, one may use the same site for preparing the conjugate immunogen to produce antibodies, as the site for the active functionality for linking to the surface.

The assays may be performed in a competitive mode or a sandwich mode. In the competitive mode, one has the target competing with a labeled binding member for the reciprocal member, which reciprocal member is bound to the support, either during the complex formation or after, e.g. where antibody is a specific binding member and anti(IgH)is bound to the support. In this mode, the binding sites of the reciprocal binding member become at least partially filled by the target, reducing the number of available binding sites for the labeled reciprocal binding member. Thus, the number of labeled binding members that bind to the reciprocal binding member will be in direct proportion to the number of target molecules present. In the sandwich mode, the target is able to bind at the same time to different binding members; a first support bound member and a second member which binds at a site of the target molecule different from the site at which the support bound member binds. The resulting complex has three components, where the target serves to link the labeled binding member to the support.

In carrying out the assays, the components are combined, usually with the target composition added first and then the labeled members in the competitive mode and in any order in the sandwich mode. Usually, the labeled member in the competitive mode will be equal to at least 50% of the highest number of target molecules anticipated, preferably at least equal and may be in 2–10 fold excess or greater. The particular ratio of target molecules to labeled molecules will depend on the binding affinities, the length of time the mixture is incubated, the off rates for the target molecule with its reciprocal binding member, the size of the sample and the like. In the case of the sandwich assays, one will have at least an equal amount of the labeled binding member to the highest expected amount of the target molecules, usually at least 1.5 fold excess, more usually at least 2 fold excess and may have 10 fold excess or more. The components are combined under binding conditions, usually in an aqueous medium, generally at a pH in the range of 5–10, with buffer at a concentration in the range of about 10 to 200 mM. These conditions are conventional, where conventional buffers may be used, such as phosphate, carbonate, HEPES, MOPS, Tris, borate, etc., as well as other conventional additives, such as salts, stabilizers, organic solvents, etc.

Usually, the unbound labeled binding member will be removed by washing the bound labeled binding member. Where particles or beads are employed, these may be separated from the supernatant before washing, by filtration, centrifugation, magnetic separation, etc. After washing, the support may be combined with a liquid into which the e-tags are to be released and/or the functionality of the e-tags is reacted with the detectable label, followed by or preceded by release. Depending on the nature of the cleavable bond and the method of cleavage, the liquid may include reagents for the cleavage. Where reagents for cleavage are not required, the liquid is conveniently an electrophoretic buffer. For example, where the cleavable linkage is photo labile, the support may be irradiated with light of appropriate wavelength to release the e-tags. Where detectable labels are not present on the e-tags, the e-tags may be reacted with the detectable labels. In some instances the detectable label may be part of the reagent cleaving the cleavable bond, e.g. a disulfide with a thiol. Where there is a plurality of different functionalities on different binding members for reaction with the label, the different labels will have functionalities that react with one of the functionalities. The different labels may be added together or individually in a sequential manner. For example, where the functionalities involve thiols, carboxyl groups, aldehydes and olefins, the labels could have activated olefins, alcohols, amines and thiol groups, respectively. By having removable protective groups for one or more of the functionalities, the protective groups may be removed stepwise and the labels added stepwise. In this way cross-reactivity may be avoided. Whether one has the detectable label present initially or one adds the detectable label is not critical to this invention and will frequently be governed by the nature of the target composition, the nature of the labeled binding members, and the nature of the detectable labels. For the most part, it will be a matter of convenience as to the particular method one chooses for providing the detectable labeled e-tag.

Where a reagent is necessary for cleavage, the e-tags may be required to be separated from the reagent solution, where the reagent interferes with the electrophoretic analysis.

Depending on the nature of the e-tags and the reagent, one may sequester the e-tags from the reagent by using ion exchange columns, liquid chromatography, an initial electrophoretic separation, and the like. Alternatively, as discussed previously, one may have a ligand bound to the e-tag or retained portion of the target-binding region for isolating the e-tag, so as to remove any interferents in the mixture. Once the solution of e-tags is prepared and free of any interfering components, the solution may be analyzed electrophoretically. The analysis may employ capillary electrophoresis devices, microfluidic devices or other devices that can separate a plurality of compounds electrophoretically, providing resolved bands of the individual e-tags.

The protocols for the subject homogeneous assays will follow the procedures for the analogous assays, which may or may not include a releasable tag. These protocols employ a signal producing system that includes the label on one of the binding members, the cleavable bond associated with the e-tag, electromagnetic radiation or other reagents involved in the reaction or for diminishing background signal. In assays involving the production of hydrogen peroxide, one may wish to have a molecule in solution that degrades hydrogen peroxide to prevent reaction between hydrogen peroxide produced by a label bound to an analyte molecule and an e-tag labeled binding member that is not bound to the same analyte molecule.

Generally, the concentrations of the various agents involved with the signal producing system will vary with the concentration range of the individual analytes in the samples to be analyzed, generally being in the range of about 10 nM to 10 mM. Buffers will ordinarily be employed at a concentration in the range of about 10 to 200 mM. The concentration of each analyte will generally be in the range of about 1 pM to about 100 $\mu$M, more usually in the range of about 100 $\mu$M to 10 $\mu$M. Although in specific situations the concentrations may be higher or lower, depending on the nature of the analyte, the affinity of the reciprocal binding members, the efficiency of release of the e-tags, the sensitivity with which the e-tags are detected, and the number of analytes, as well as other considerations.

The reactive species that is produced in the assay, analogous to the subject assay, is employed in a different way than was used in the analogous assay, but otherwise the conditions will be comparable. In many instances, the chemiluminescent compound when activated will result in cleavage of a bond, so that one may obtain release of the e-tag. Assays that find use are described in U.S. Pat. Nos. 4,233,402; 5,616,719; 5;807,675; and 6,002,000. One would combine the analyte with one or both reagents. The particular order of addition will vary with the nature of the reagents. Generally, one would prefer to combine the binding reagents and the sample and allow the mixture to incubate, generally at least about 5 min, more usually at least about 15 min, before irradiating the mixture or adding the remaining reagents.

One may also use the subject libraries to analyze the effect of an agent on a plurality of different compounds. For example, one may prepare a plurality of substrates labeled with an e-tag, where the enzyme catalyzes a reaction resulting in a change in mobility between the product and the starting material. These assays can find use in determining affinity groups or preferred substrates for hydrolases, oxidoreductases, lyases, etc. For example, with kinases and phosphatases, one adds or removes a charged group, so as to change the mobility of the product. By preparing a plurality of alcohols or phosphate esters, one can determine which of the compounds serves as a substrate. By labeling the substrates with e-tags, one can observe the shift from the substrate to the product as evidence of the activity of a candidate substrate with the enzyme. By preparing compounds as suicide inhibitors, the enzymes may be sequestered and the e-tags released to define those compounds that may serve as suicide inhibitors and, therefore, preferentially bind to the active site of the enzyme.

One may also use the subject methods for screening for the activity of one or more candidate compounds, particularly drugs, for their activity against a battery of enzymes. In this situation, one would use active substrates for each of the enzymes to be evaluated, where each of the substrates would have its own e-tag. For those enzymes for which the drug is an inhibitor, the amount of product would be diminished in relation to the amount of product in the absence of the candidate compound. In each case the product would have a different mobility from the substrate, so that the substrates and products could be readily distinguished by electrophoresis. By appropriate choice of substrates and detectable labels, one would obtain electropherograms showing the effect of the candidate compound on the activity of the different enzymes.

In those instances where a fluorescent label is not present on the e-tag bound to the product comprising the mir, the mixture may be added to functionalized fluorescent tags to label the e-tag with a fluorescer. For example, where a thiol group is present, the fluorescer could have an activated ethylene, such as maleic acid to form the thioether. For hydroxyl groups, one could use activated halogen or pseudohalogen for forming an ether, such as an $\alpha$-haloketone. For carboxyl groups, carbodiimide and appropriate amines or alcohols would form amides and esters, respectively. For an amine, one could use activated carboxylic acids, aldehydes under reducing condtions, activated halogen or pseudohalogen, etc. When synthesizing oligopeptides, protective groups are used. These could be retained while the fluorescent moiety is attached to an available functionality on the oligopeptide.

The presence of each of the released or intact e-tags is determined by the label. The separation of the mixture of labeled e-tags is carried out by electroseparation, which involves the separation of components in a liquid by application of an electric field, preferably, by electrokinesis (electrokinetic flow), electrophoretic flow, electroosmotic flow or combination thereof, with the separation of the e-tag mixture into individual fractions or bands. Electroseparation involving the migration and separation of molecules in an electric field is based on differences in mobility. Various forms of electroseparation include, by way of example and not limitation, free zone electrophoresis, gel electrophoresis, isoelectric focusing and isotachophoresis. Capillary electroseparation involves electroseparation, preferably by electrokinetic flow, including electrophoretic, dielectrophoretic and/or electroosmotic flow, conducted in a tube or channel of about 1–200 $\mu$m, usually, about 10–100 $\mu$M cross-sectional dimensions. The capillary may be a long independent capillary tube or a channel in a wafer or film comprised of silicon, quartz, glass or plastic.

In capillary electroseparation, an aliquot of the reaction mixture containing the e-tag products is subjected to electroseparation by introducing the mixture or an aliquot into an electroseparation channel that may be part of, or linked to, a capillary device in which the amplification and other reactions are performed. An electric potential-is then applied to the electrically conductive medium contained within the channel to effectuate migration of the components within the combination. Generally, the electric potential applied is sufficient to achieve electroseparation of the desired components according to practices well known in the art. One skilled in the art will be capable of determining the suitable electric potentials for a given set of reagents used in the present invention and/or the nature of the cleaved labels, the nature of the reaction medium and so forth. The parameters for the electroseparation including those for the medium and the electric potential are usually optimized to achieve maximum separation of the desired components. This may be achieved empirically and is well within the purview of the skilled artisan.

Capillary devices are known for carrying out amplification reactions such as PCR. See, for example, Analytical Chemistry (1996) 68:4081–4086. Devices are also known that provide functional integration of PCR amplification and capillary electrophoresis in a microfabricated DNA analysis device. One such device is described by Woolley, et al., in *Anal. Chem.* (1996) 68:4081–4086. The device provides a microfabricated silicon PCR reactor and glass capillary electrophoresis chips. In the device a PCR chamber and a capillary electrophoresis chip are directly linked through a photolithographically fabricated channel filled with a sieving matrix such as hydroxyethylcellulose. Electrophoretic injection directly from the PCR chamber through the cross injection channel is used as an "electrophoretic valve" to couple the PCR and capillary electrophoresis devices on a chip.

The capillary electrophoresis chip contains a sufficient number of main or secondary electrophoretic channels to receive the desired number of aliquots from the PCR reaction medium or the solutions containing the e-tags, etc., at the intervals chosen.

For capillary electrophoresis one may employ one or more detection zones to detect the separated e-tags. It is, of course, within the purview of the present invention to utilize several detection zones depending on the nature of the amplification process, the number of cycles for which a measurement is to be made and so forth. There may be any number of detection zones associated with a single channel or with multiple channels. Suitable detectors for use in the detection zones include, byway of example, photomultiplier tubes, photodiodes, photodiode arrays, avalanche photodiodes, linear and; array charge coupled device (CCD) chips, CCD camera modules, spectrofluorometers, and the like. Excitation sources include, for example, filtered lamps, LED's, laser diodes, gas, liquid and solid state lasers, and so forth. The detection may be laser scanned excitation, CCD camera detection, coaxial fiber optics, confocal back or forward fluorescence detection in single or array configurations, and the like.

Detection may be by any of the known methods associated with the analysis of capillary electrophoresis columns including the methods shown in U.S. Pat. No. 5,560,811 (column 11, lines 19–30), U.S. Pat. Nos. 4,675,300, 4,274,240 and 5,324,401, the relevant disclosures of which are incorporated herein by reference.

Those skilled in the electrophoresis arts will recognize a wide range of electric potentials or field strengths may be used, for example, fields of 10 to 1000 V/cm are used with 200–600 V/cm being more typical. The upper voltage limit for commercial systems is 30 kV, with a capillary length of 40–60 cm, giving a maximum field of about 600 V/cm. For DNA, typically the capillary is coated to reduce electroosmotic flow, and the injection end of the capillary is maintained at a negative potential, which may be reversed, as appropriate.

For ease of detection, the entire apparatus may be fabricated from a plastic material that is optically transparent, which generally allows light of wavelengths ranging from 180 to 1500 nm, usually 220 to 800 nm, more usually 450 to 700 nm, to have low transmission losses. Suitable materials include fused silica, plastics, quartz, glass, and so forth.

In mass spectrometry, the e-tags may be different from the e-tags used in electrophoresis, since the e-tags do not require a label, nor a charge. Thus, these e-tags may be differentiated solely by mass, which can be a result of atoms of different elements, isotopes of such elements, and numbers of such atoms. In the subject invention, such use of e-tags will be coupled with a process for removing the iterative extensions of the nucleic acid sequence, where degradation or cleavage has occurred at a site other than the ultimate linkage.

Figure 10:
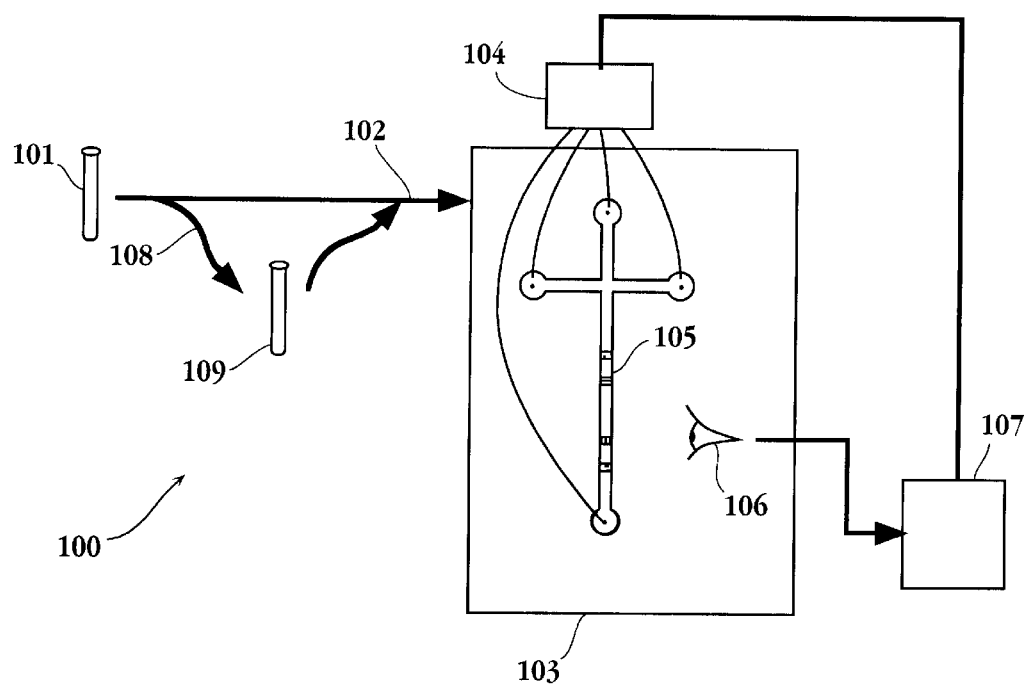
FIG. 10 is a schematic of a system for performing multiplexed determinations using e-tags.

One embodiment of a system according to the present invention is presented in FIG. 10. This figure illustrates a system (100) for the simultaneous, multiplexed determination of a plurality of events. Each event is distinguished from the others by electrophoresis. For example, a snp locus may be characterized using a pair of reagents, each specific for one allele of the locus. Each reagent is bonded to an e-tag with a unique electrophoretic mobility and an associated label. When the reagent is combined with a sample of interest in a reaction vessel (101), the associated e-tag is modified in a manner that changes its electrophoretic mobility if its specific target is present. After the reaction, the mixture is moved (102) onto an electrophoretic device (103) for separation of the e-tags contained in the mixture. A power control box (104) is used in conjunction with the device to control injection of the sample into the separation channel (105). Each e-tag species migrates down the separation channel of the device with a mobility unique to that tag, moving past a detector (106) that monitors its presence by its associated label. The data collected by the detector is sent to a data processor (107), which determines the presence of each snp allele in the sample based on the mobility of its corresponding e-tag.

In another example, a group of snp loci may be monitored in a multiplexed reaction. In this case, a plurality of pairs of e-tag reagents corresponding to the snp loci are combined with the sample in a single reaction vessel under conditions where the e-tag is released from at least a portion of the oligonucleotides sequence to which it is bonded when a pair is bonded to its target. The e-tags are either labeled for detection or the label is added by means of a reactive functionality present on the e-tag. The labeled e-tag products of the reaction are resolved from one another on the electrophoretic device, and again are monitored as they move past the detector. The level of multiplexing possible in this system is limited only by the degree of resolution that can be obtained between a designated set of e-tags on the electrophoretic device.

An additional degree of flexibility can be conferred on the assay by the stage at which the e-tags are labeled. As described above, each e-tag may already, contain a detectable label when introduced to the reaction. Alternatively, an e-tag may contain a functionality allowing it to bind to a label after reaction with the sample is complete (108). In this embodiment, an e-tag comprising a functionality for binding to a detectable label is combined with a sample (101). After a reaction to modify the mobility of the e-tag if its target is present in the sample, additional reagents are combined in a sample vessel (109) with the products of the first reaction, which will react with the modified e-tag(s) to add a detectable label.

EXAMPLES

The invention is demonstrated further by the following illustrative examples. Parts and percentages are by weight unless otherwise indicated. Temperatures are in degrees Centigrade (°C.) unless otherwise specified. The following preparations and examples illustrate the invention but are not intended to limit its scope. Unless otherwise indicated, oligonucleotides and peptides used in the following examples were prepared by synthesis using an automated synthesizer and were purified by gel electrophoresis or HPLC.

The following abbreviations have the meanings set forth below:

Tris HCl—Tris(hydroxymethyl)aminomethane-HCl (a 10× solution) from BioWhittaker, Walkersville, Md.

HPLC—high performance liquid chromatography

BSA—bovine serum albumin from Sigma Chemical Company, St. Louis Mo.

EDTA—ethylenediaminetetraacetate from Sigma Chemical Company bp—base pairs
g—grams
mM—millimolar
TET—tetrachlorofluorescein
FAM—fluorescein
TAMRA—tetramethyl rhodamine Reagents:
TET and FAMRA were purchased from Perkin Elmer (Foster City, Calif.) as were conjugates of TET, FAM and TAMRA with oligonucleotides.

Master Mix (2×): 20 mM Tris-HCl, 2.0 mM EDTA, pH 8.0 (8% Glycerol), 10 mM $MgCl_2$, dATP 400 $\mu M$, dCTP 400 $\mu M$, dGTP 400 $\mu M$, dUTP 400 $\mu M$, AmpliTaq Gold® 0.1 U/$\mu l$ (from Perkin Elmer), Amperase UNG® 0.02 U/$\mu l$ (from Perkin Elmer)

Probes and Primers: (10×)
Forward Primer: 3.5 $\mu M$ 5'-TCA CCA CAT CCC AGT G-3' (SEQ ID NO:1)
Reverse Primer 2.0 $\mu M$ 5'-GAG GGA GGTTTG GCTG-3' (SEQ ID NO:2)
Plasmid Allele 1 Probe: 2.0 $\mu M$ (200 nM per reaction)
  5' TET-CCA GCA ACC AAT GAT GCC CGT T-TAMRA-3' (SEQ ID NO:3)
Plasmid Allele 2 Probe: 2.0 $\mu M$ (200 nM per reaction)
  5' FAM-CCA GCA AGC ACT GAT GCC TGT T-TAMRA-3' (SEQ ID NO:4)

Target DNA:
Plasmid Allele-1: 10 fg/$\mu l$=approximately 1000 copies/$\mu l$
Plasmid Allele-2: 10 fg/$\mu l$=approximately 1000 copies/$\mu l$ Example 1

The Experiment was Set Up to Run in the Following Fashion (6 Samples, a Triplicate for Allele 1 and Another Triplicate for Allele-2)

22 $\mu l$ of Mastermix
13 $\mu l$ of probes and primers (both the probes are present)
4.0 $\mu l$ of Allele-1 or Allele-2
11 $\mu l$ of buffer (10 mM Tris-HCl, 1 mM EDTA, pH8.0)

The above volumes were added to a PCR tubes and the reaction mixtures were cycled in the following fashion for 40 cycles.

Initial Steps:
The reaction mixtures were kept at 50° C. for 2 minutes for optimal AmpErase UNG activity. The 10 minute, 95° C. step was requited to activate AmpliTaq Gold DNA Polymerase.

Each of the 40 cycles was performed on a Gene Amp® system 9600 thermal cycler (Perkin Elmer) in the following fashion:

| Melt | Anneal/Extend/Cleave |
|---|---|
| 15 seconds 95° C. | 60 seconds 60° C. |

Figure 2A:
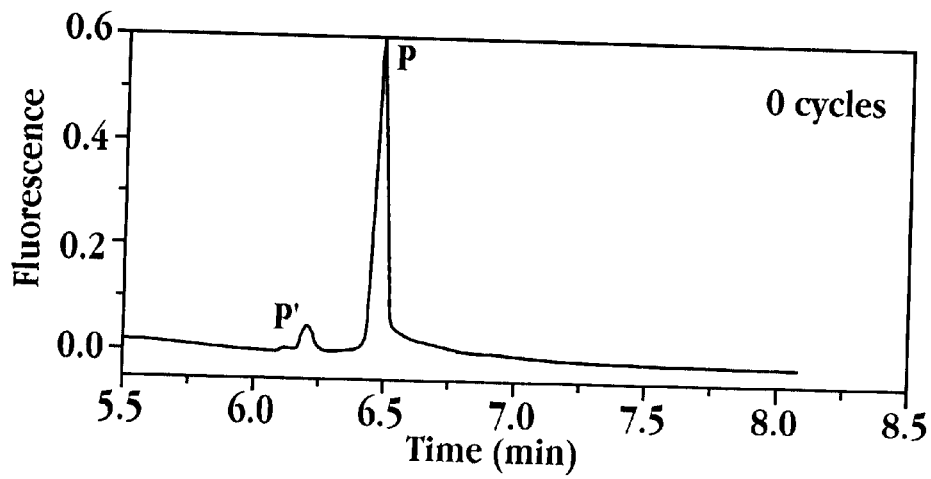
FIGS. 2A and B depict the CE separation of the reaction products of Allele 1 after 0 and 40 cycles. CE instrument: Beckman P/ACE/5000 with LIF detection. BGE: 2.5% LLD 30, 7M urea, 1×TBE. Capillary: 100 μm i.d., 375 μm o.d., Lc=27 cm, Ld=6.9 cm. Detection; $\lambda_{ex}$=488 nm, $\lambda_{em}$=520 nm. Injection: 5 s at 2.0 kV. Field strength: 100V/cm at rt. Peaks: P=unreacted snp detection sequence, P'=snp detection sequence product.
Figure 2B:
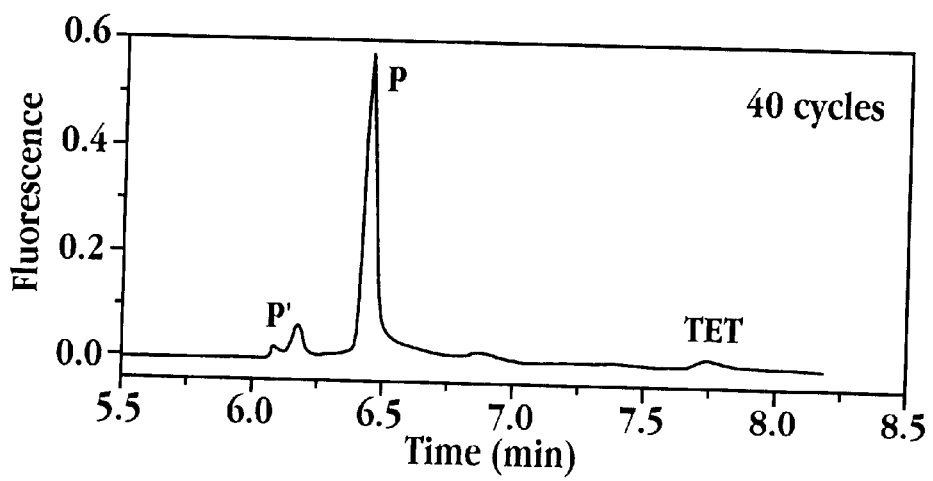

Results from experiments with Allele-1 are shown in FIG. 2. CE separation of the reaction products of Allele 1 after 0 and 40 cycles. CE instrument was Beckman P/ACE 5000 with LIF detection. BGE: 2.5% LDD30, 7 M urea, 1×TBE. Capillary: 100 $\mu m$ i.d., 375 $\mu m$ o.d., Lc=27 cm, Ld=6.9 cm. Detection: $\lambda$ex=488 nm, $\lambda$em=520 nm. Injection: 5 s at 2.0 kV. Field strength: 100 V/cm at room temperature. Peaks: P=unreacted primer, P'=primer product.

Figure 3A:
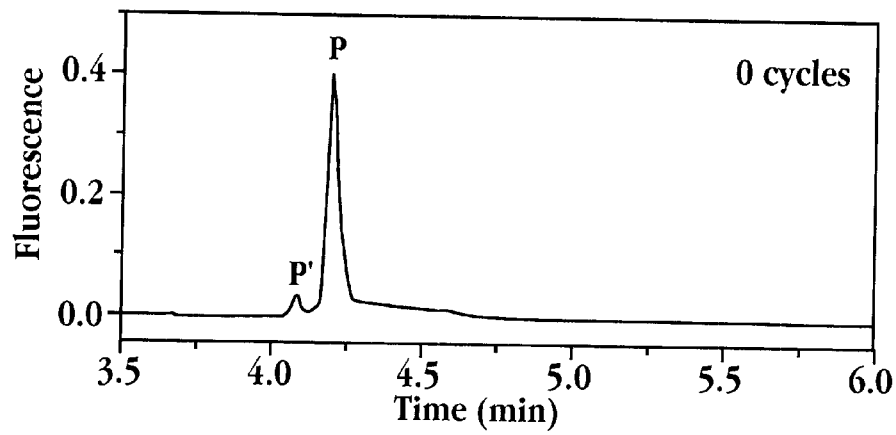
FIGS. 3A and 3B depict the CE separation of the reaction products of Allele 1 after 0 and 40 cycles. Experimental conditions are the same as FIG. 2, except for BGE composition; 2% LDD30, 1×TBE.
Figure 3B:
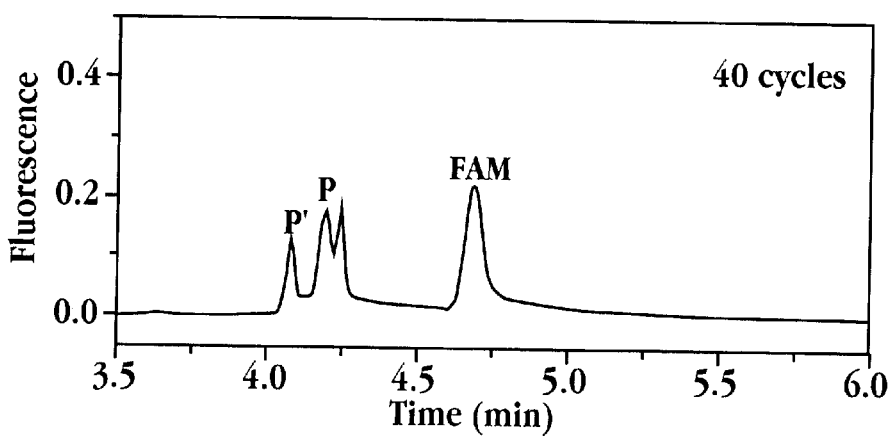

Results from experiments with Allele-2 are shown in FIG. 3. CE separation of the reaction products of Allele 2 after 0 and 40 cycles. Experimental conditions were as given above for FIG. 2 experiment except for BGE composition: 2.0% LDD30, 1×TBE.

Example 2

A Multiplexed Reaction with bBoth Allele 1 and Allele 2 Present in Equal Ratio

The experiment was set up in the following fashion (3 reaction tubes, a triplicate)

22 $\mu l$ of Mastermix
13 $\mu l$ of probes and primers (both of the probes were present)
4.0 $\mu l$ of Allele-1
4.0 $\mu l$ of Allele-2
7 $\mu l$ of buffer (10 mM Tris-HCl, 1 mM EDTA, pH8.0)

The above volumes were added to a PCR tubes and the reaction mixtures were cycled in the following fashion for 40 cycles.

Initial Steps:
The reaction mixtures are kept at 50° C. for 2 minutes for optimal AmpErase UNG activity. The 10 minute, 95° C. step is required to activate AmpliTaq Gold DNA: Polymerase.

Each of the 40 cycles is performed in the following fashion

| Melt | Anneal/Extend/Cleave |
|---|---|
| 15 seconds 95° C. | 60 seconds 60° C. |

Figure 4:
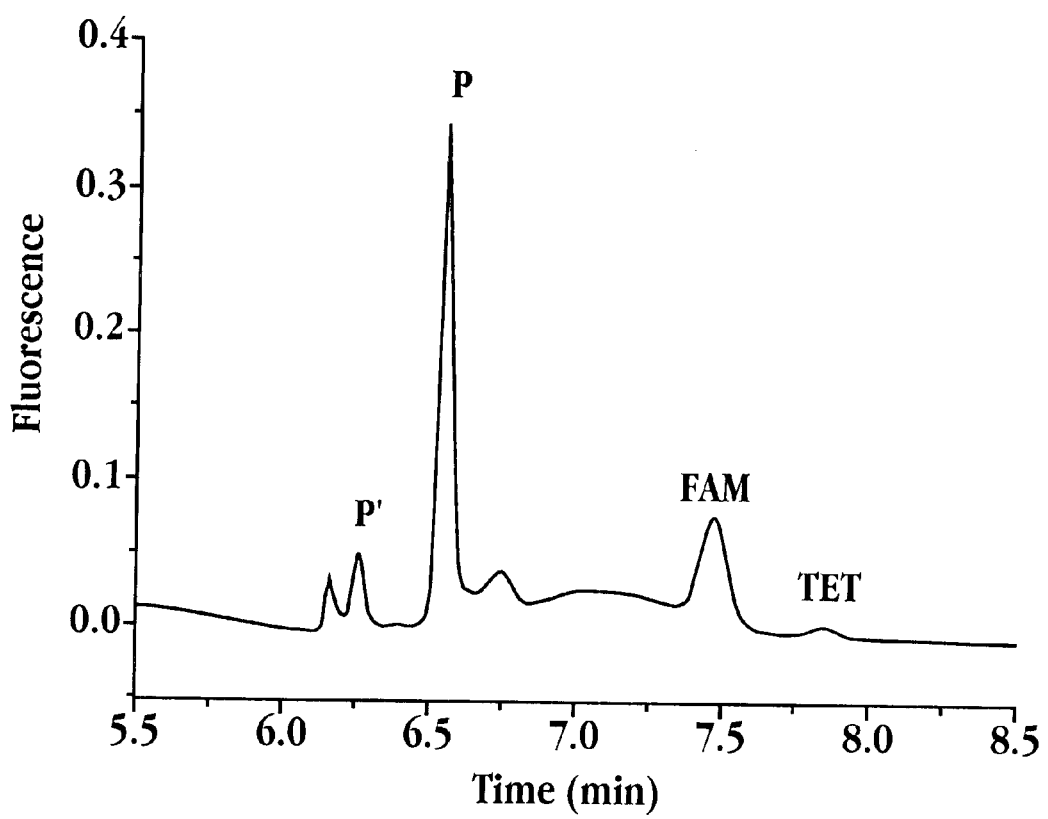
FIG. 4 is a graph of the CE separation of a 1:1 mixture of the 40 cycles products of Alleles 1 and 2, with experimental conditions as described for FIG. 2.

The results are shown in FIG. 4. CE separation of a 1:1 mixture of the 40 cycles products of Alleles 1 and 2. Experimental conditions were as given above for the experiments of FIG. 2.

Example 3

A Multiplexed Reaction with Both Allele 1 and Allele 2: Allele 1 is 10 Times More Concentrated than Allele 2.

The experiment was set up in the following fashion (3 reaction tubes, a triplicate)

22 $\mu l$ of Mastermix
13 $\mu l$ of probes and primers (both the probes were present)
5.0 $\mu l$ of Allele 1
0.5 $\mu l$ of Allele 2
9.5 tll of buffer (10 mM Tris-HCl, 11 mM EDTA, pH8.0)

The above volumes were added to respective PCR tubes and the reaction mixtures were cycled in the following fashion for 40 cycles.

Initial Steps:
The reaction mixtures were kept at 50° C. for 2 minutes for optimal AmpErase UNG activity. The 10 minute 95° C. step was required to activate AmpliTaq Gold DNA Polymerase.

Each of the 40 cycles is performed in the following fashion

| Melt | Anneal/Extend/Cleave |
|---|---|
| 15 seconds 95° C. | 60 seconds 60° C. |

Figure 5:
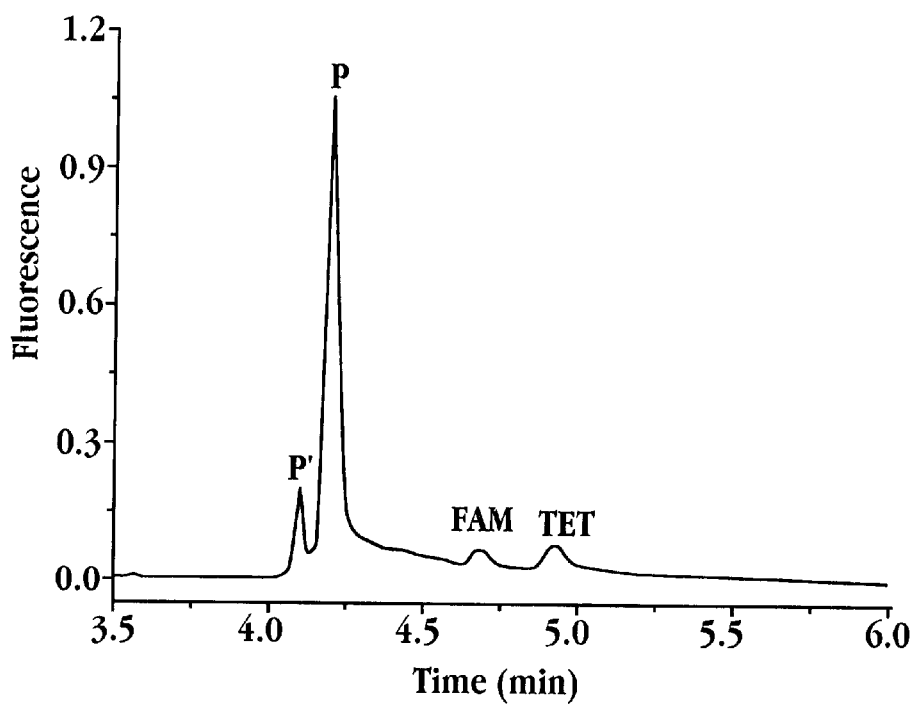
FIG. 5 is a graph of the CE separation of a 1:10 mixture of the 40 cycles products of Alleles 1 and 2, with experimental conditions as described for FIG. 2.

The results are shown in FIG. 5. CE separation of a 1:10 mixture of the 40 cycles products of Alleles 1 and 2. Experimental conditions were as given for the experiments of FIG. 2.

Example 4

Label conjugates comprising fluorescein linked to three different peptides, namely, KKAA (SEQ ID NO: 5), KKKA (SEQ ID NO: 6) and KKKK (SEQ ID NO: 7) were prepared as follows: The protected tetrapeptide was prepared on resin using Merrifield reagents. The N-terminus of the last amino acid was reacted with fluorescein N-hydroxysuccinimide (Molecular Probes). The peptides were cleaved from the resin and purified by high performance liquid chromatography (HPLC).

Figure 6:
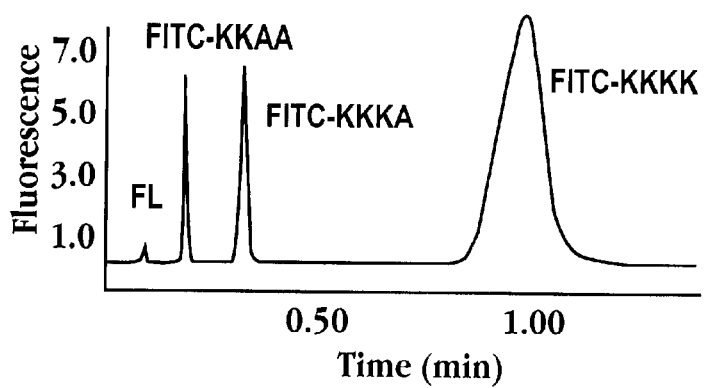
FIG. 6 is an electopherogram of e-tags, which involved a separation involving a 1000-fold difference in concentration.
Figure 7A:
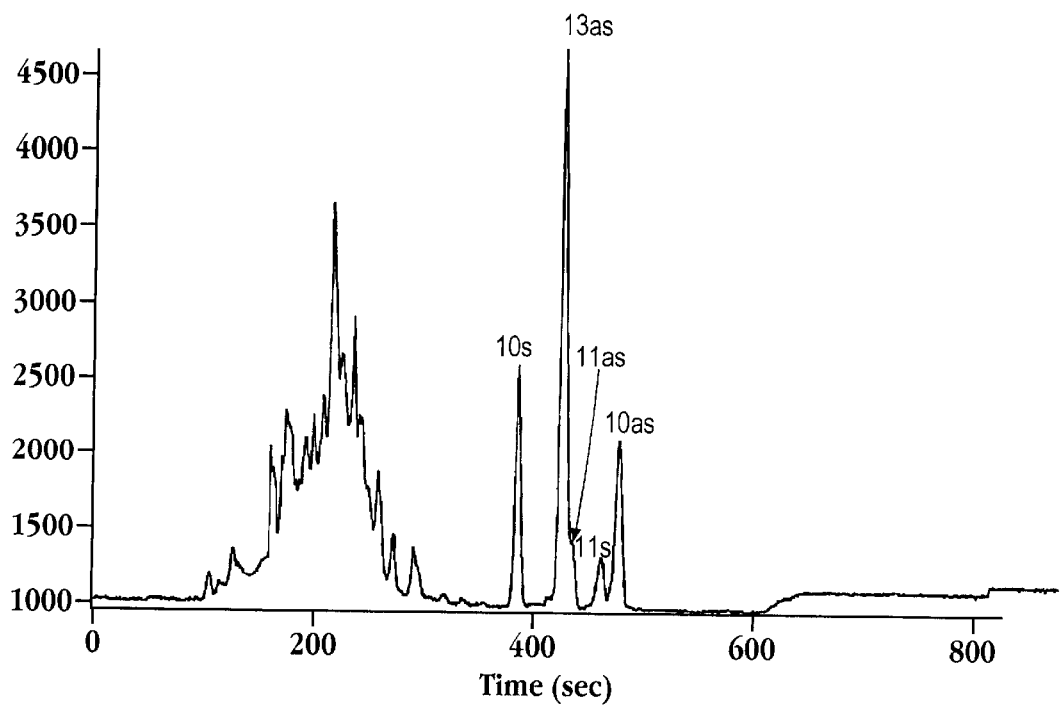
FIGS. 7A and 7B are the electropherograms of the analysis of 5 snps of the cystic fibrosis genes using multiplexed PCR and the subject e-tag probes.
Figure 7B:
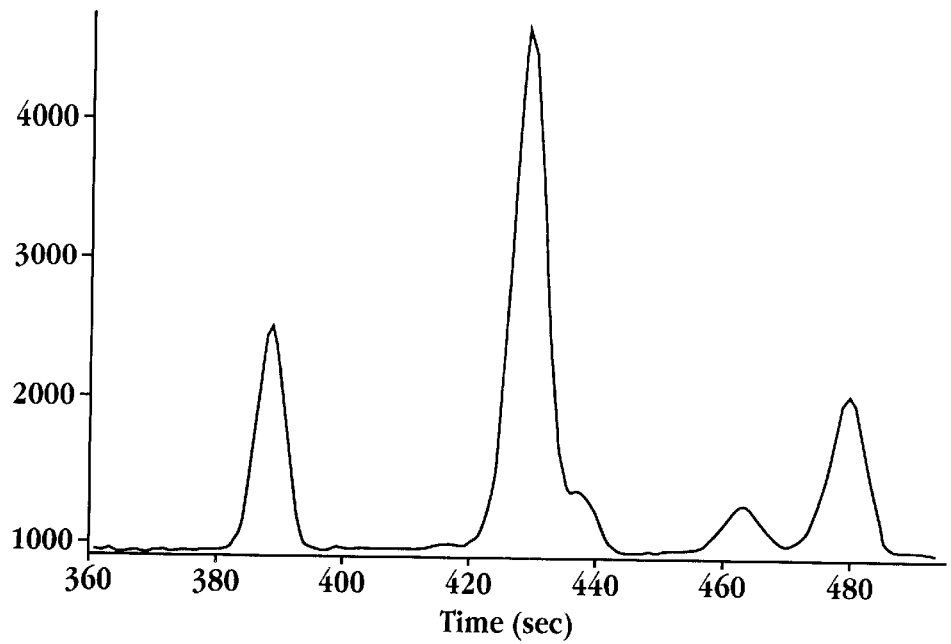
Figure 7C:
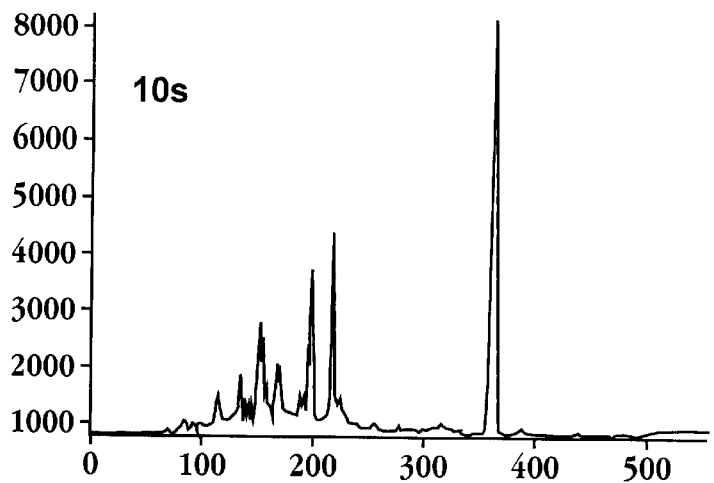
FIGS. 7C–7G are the electropherogram of the analysis of single snps and triplex snps for the cystic fibrosis genes using multiplexed PCR and the subject e-tag probes along with an agarose gel separation of the triplexPCR.
Figure 7D:
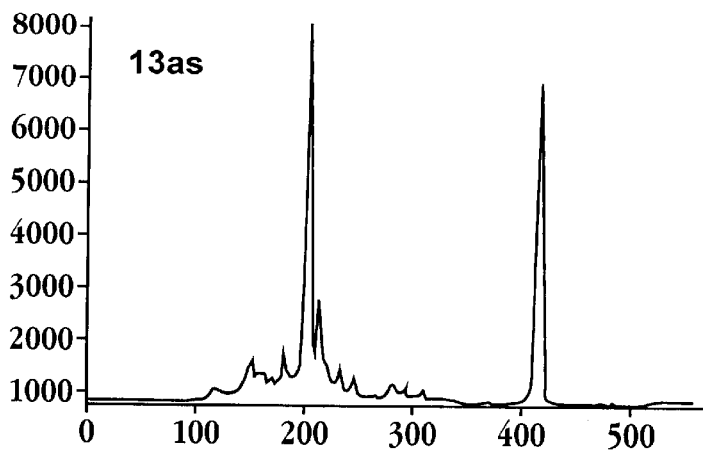
Figure 7E:
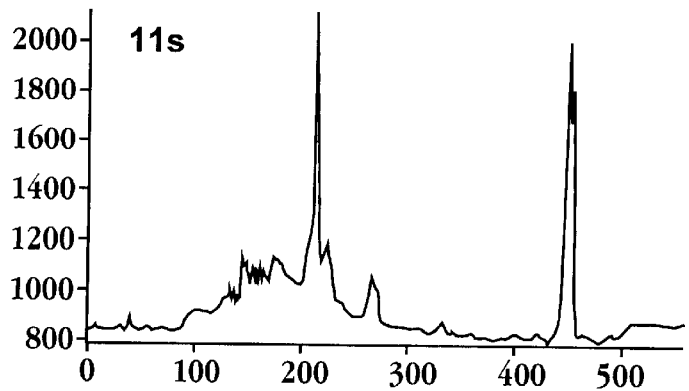
Figure 7F:
Figure 7G:
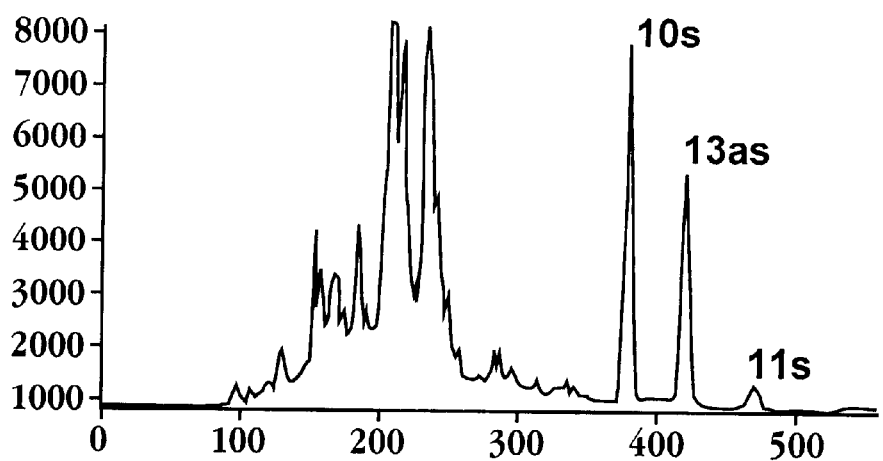

The label conjugates prepared as described above and fluorescein were combined in an aqueous buffered and were separated and detected in an electrophoresis chip. Detection was 0.5 cm for the injection point on the anodal side of an electrophoresis channel. FITC-KKKK (SEQ ID NO:54) exhibited negative charge and FITC-KKKA (SEQ ID NO:55) and FITC-KKAA (SEQ ID NO:56) exhibited positive charge as determined by the migration time relative to EOF. The net charge of FITC-KKKK (SEQ ID NO:54) was greater than +1 and FITC-KKKA (SEQ ID NO:55) and FITC-KKAA (SEQ ID NO:56) migrated electrophoretically against the EOF. The results are shown in FIG. 6.

Example 5

Capillary Electrophoresis of CFTR PCR Products with e-tag Probes on ABI 310

The following example demonstrates separation in a gel based capillary electrophoresis of cleavage of a probe. The conditions employed were: Gel: 2.5% LDD30 in IXTBE with 7M urea; CE: PE ABI 310; Capillary: 47 cm long; 36 cm to window; 75 um ID; Running Buffer: 1×TBE. (LDD30 is a linear copolymer of N,N-diethyl acrylamide and N,N-dimethylacrylamide, 70:30).

The ABI310 was set up in accordance with the directions of the manufacturer.

The parameters used were: Inj Secs 5; Inj kV 2.0; Run kV 9.4; Run C 45; Run Timel 10 min. To determine the relationship of where each probe separated, a spike in system was used. First one digested probe was separated and its peak site determined, then a second probe was spiked into the first probe and the two separated. Then, a third probe was spiked in and separated, and so on till the sites of all the six probes was determined. The single plex PCR runs were first separated followed by separation of the multiplex PCR, which was compared to the S1 digested separation.

| Sample* | Type of probe | Probe conc. (nM) | vol (µl) |
|---|---|---|---|
| 10s FAM-T | 32 mer | 20 | 10 |
| 10s FAM-T | dig | 20 | 10 |
| 10s FAM-T | pcr | 80 | 5 |
| 10as HEX-T | 32 mer | 20 | 10 |
| 10as HEX-T | dig | 20 | 10 |
| 10as HEX-T | pcr | 80 | 5 |
| 11s HEX-A | 28 mer | 20 | 10 |
| 11s HEX-A | dig | 20 | 10 |
| 11s HEX-A | pcr | 80 | 5 |
| 11as TET-C | 28 mer | 20 | 10 |
| 11as TET-C | dig | 20 | 10 |
| 11as TET-C | pcr | 80 | 5 |
| 13s FAM-C | 23 mer | 20 | 10 |
| 13s FAM-C | dig | 20 | 10 |
| 13s FAM-C | pcr | 80 | 5 |
| 13as TET-A | 23 mer | 20 | 10 |
| 13as TET-A | dig | 20 | 10 |
| 13as TET-A | pcr | 80 | 5 |
| MP10s11s13as | pcr | 80 | 5 |
| MP10as11as13a | pcr | 80 | 5 |
| MP10s10as11s11as13s13as | pcr | 80 | 5 | dig - S1 nuclease digestion; pcr - amplification;
*the particular samples are found in the above table, where as exemplary 10s FAM-T intends Exon 10 sense, which is referred to as CF7, so that one looks to CF7 for the probe sequence, FAM intends fluorescein, and T is the nucleotide to which the fluorescein is attached.
For the other symbols, "as" is the antisense sequence,
HEX is hexachlorofluorescein,
TET is tetrachlorofluorescein, and when more than one exon is indicated, the reaction mixture is multiplexed under the conditions described below Example 6

Taq DNA Polymerase exhibits 5' to 3' exonuclease activity in which hybridized probes on the template DNA are cleaved during PCR. In the subject example, sequence specific probes with fluorescent dye attached to the 5' were employed. PCR was performed with these probes in a reaction and then separation performed in a gel based capillary electrophoresis to determine the cleavage of the probe.

| Name | Location | | Mutation | SNP |
|---|---|---|---|---|
| | SNP | | | |
| CF1 | Exon 11 | | R553X | C1789T |
| CF2 | Exon 19 | | R1162X | C3616T |
| CF4 | Exon 3 | | G85E | G386A |
| CF5 | Exon 4 | | R117H | G482A |
| CF6 | Exon 7 | | R347P | G1172C |
| CF7 | Exon 10 | | V520F | G1690T |
| CF8 | Exon 11 | | 542X | G1756T |
| CF9 | Exon 11 | | G551D | G1784A |

-continued

| Name | | | |
|---|---|---|---|
| CF10* | Exon 11 | R560T | G1811C |
| CF11* | Exon 18 | D1152H | G3586C |
| CF13* | Exon 22 | G1349D | G4178A |

| | Hyb_probe_length | Probe_seq | Probe_antisense |
|---|---|---|---|
| CF1HYB | 26 | GTGGAGGTCAACGAGCAAGAATTTCT (SEQ ID NO: 8) | AGAAATTCTTGCTCGTTGACC TCCAC (SEQ ID NO: 30) |
| CF2HYB | 25 | AGATGCGATCTGTGAGCCGAGTCTT (SEQ ID NO: 9) | AAGACTCGGCTCACAGATCGC ATCT (SEQ ID NO: 31) |
| CF4HYB | 32 | TTCTGGAGATTTATGTTCTATGGAATC TTTTT (SEQ ID NO: 10) | AAAAAGATTCCATAGAACATA AATCTCCAGAA (SEQ ID NO: 32) |
| CF5HYB | 21 | AAGGAGGAACGCTCTATCGCG (SEQ ID NO: 11) | CGCGATAGAGCGTTCCTCCTT (SEQ ID NO: 33) |
| CF6HYB | 20 | ATTGTTCTGCGCATGGCGGT (SEQ ID NO: 12) | ACCGCCATGCGCAGAACAAT (SEQ ID NO: 34) |
| CF7HYB | 25 | ATACAGAAGCGTCATCAAAGCATGC (SEQ ID NO: 13) | GCATGCTTTGATGACGCTTCT GTAT (SEQ TD NO: 35) |
| CF8HYB | 29 | CAATATAGTTCTTGGAGAAGGTGGAAT CA (SEQ TD NO: 14) | TGATTCCACCTTCTCCAAGAA CTATATTG (SEQ ID NO: 36) |
| CF9HYB | 26 | CTGAGTGGAGGTCAACGAGCAAGAAT (SEQ ID NO: 15) | ATTCTTGCTCGTTGACCTCCAC TCAG (SQ ID NO: 37) |
| CF10HYB* | 32 | TTCCATTTTCTTTTTAGAGCAGTATACA AAGA (SEQ ID NO: 16) | TCTTTGTATACTGCTCTAAAA AGAAAATGGAA (SEQ ID NO: 38) |
| CF11HYB* | 28 | AAACTCCAGCATAGATGTGGATAGCTT G (SEQ ID NO: 17) | CAAGCTATCCACATCTATGCT GGAGTTT (SEQ ID NO: 39) |
| CF13HYB* | 23 | CTAAGCCATGGCCACAAGCAGTT (SEQ ID NO: 18) | AACTGCTTGTGGCCATGGCTT AG (SEQ ID NO: 40) |

| | product_size | forward seq | Reverse seq |
|---|---|---|---|
| CF1PF/R | 198 | CCTTTCAAATTCAGATTGAGCATAC (SEQ ID NO: 19) | TTTACAGCAAATGCTTGCTAG AC (SEQ ID NO: 41) |
| CF2PF/R | 127 | TGTGAAATTGTCTGCCATTCTTA (SEQ ID NO: 20) | GGTTTGGTTGACTTGGTAGGT TTA (SEQ ID NO: 42) |
| CF4PF/R | 239 | TCTTTTGCAGAGAATGGGATAGA (SEQ ID NO: 21) | TGGAGTTGGATTCATCCTTTAT ATT (SEQ ID NO: 43) |
| CF5PF/R | 151 | CCAAAGCAGTACAGCCTCTCTTA (SEQ ID NO: 22) | CCAAAAATGGCTGGGTGTAG (SEQ ID NO: 44) |
| CF6PF/R | 137 | TCTGTGCTTCCCTATGCACTAA (SEQ ID NO: 23) | CCAAGAGAGTCATACCATGTT TGTA (SEQ ID NO: 45) |
| CF7PF/R | 146 | TGGAGCCTTCAGAGGGTAAA (SEQ ID NO: 24) | TGCTTTGATGACGCTTCTGTA (SEQ ID NO: 46) |
| CF8PF/R | 198 | CCTTTCAAATTCAGATTGAGCATAC (SEQ ID NO: 25) | TTTACAGCAAATGCTTGCTAG C (SEQ ID NO: 47) |
| CF9PF/R | 198 | CCTTTCAAATTCAGATTGAGCATAC (SEQ ID NO: 26) | TTTACAGCAAATGCTTGCTAG AC (SEQ ID NO: 48) |
| CF10PF/R | 108 | GACCAGGCAAATAGAGAGGAAATGTA (SEQ ID NO: 27) | CATCTAGGTATCCAAAAGGAG AGTCTA (SEQ ID NO: 49) |
| CF11PF/R* | 188 | GAAGGAGAAGGAAGAGTTGGTATTAT C (SEQ ID NO: 28) | CGGTATATAGTTCTTCCTCATG CTATT (SEQ ID NO: 50) |
| CF13PF/R* | 138 | TTGGGCTCAGATCTGTGATAG (SEQ ID NO: 29) | GCAAGATCTTCGCCTTACTG (SEQ ID NO: 51) |

| Name | m_prob, Tm_forward, Tm_reverse, oC | orward_length, everse_length |
|---|---|---|
| CF1HYB | CF1PF/R | 66.83, 60.36, 58.78 | 25, 23 |
| CF2HYB | CF2PF/R | 68.65, 59.64, 60.51 | 23, 24 |
| CF4HYB | CF4PF/R | 64.24, 60.21, 59.2 | 23, 25 |
| CF5HYB | CF5PF/R | 65.06, 60.08, 60.36 | 23, 20 |
| CF6NYB | CF6PF/R | 68.18, 59.9, 59.48 | 22, 25 |

The procedure employed in carrying out the Single-plex PCR reaction was as follows:

1. Make up Master Mix

| 1x | 6.5x | |
|---|---|---|
| 13.2ul | 85.8ul | Water |
| 3ul | 19.5ul | 25mM MgCl$_2$ |
| 2.5ul | 16.25ul | 10x PCR Buffer |
| 1ul | 6.5ul | 20ng/ul DNA template |
| 0.2ul | 1.3ul | 25mM dNTPs |
| 0.3ul | 1.95ul | 5u/ul Taq Gold (this is added just |

-continued prior to start of reaction)
2. Aliquot .8ul of 5uM probe and 4ul of 10uM primer set to PCR tubes.
3. Primer sets    Probe
   10s           CF10s
   10as          CF10as
   11s           CF11s
   11as          CF11as
   13s           CF13s
   13as          CF13as
4. Aliquot 20.2ul of the Master Mix to each tube.
5. In a PE2400 cycler,
   96C; 10 MIN
   35CYCLES
   95C; 10 SEC
   55C; 30 SEC
   70C; 45 SEC
   35CYCLES
   70C; 10 MIN
   4C; 24 hours
6. After PCR, run the 2.5ul of each sample on a 2.5% agarose gel.
7. EtBr stain the gel, take image with camera equipped UV source.
   Results clearly demonstrated the formation of a unique
   electrophoretic tag with distinct mobility (Table 1) for each amplified
   sequence
   Multiplex Amplification of CFTR Fragments with e tag Probes In this study the reaction involved a plurality of probes in the same PCR
reaction mixture for different snps in CFTR. In the subject system,
sequence specific probes with fluoroscent dye attached to the 5'
terminus of the probe were employed. PCR was performed with these
probes and then separation performed in gel based capillary
electrophoresis to determine the cleavage of the probe. The following
table indicates the fragment, the mutation reference and the specific
nucleotide difference and number inb the sequence.
The procedure employed for performing the multiplex amplification
was as follows:
Make up Master Mix
   1x       2.2x
   8ul      17.6ul    25mM MgCl$_2$
   2.5ul    5.5ul     10x PCR Buffer
   8ul      17.6ul    10ng/ul DNA template
   .2ul     .44ul     25mM dNTPs
   1ul      2.2ul     5u/ul Taq Gold (this is added just
                      prior to start of reaction)
8. Aliquot 0.8ul of each 5uM probes CF10s, CF11s, CF10as,
   CF11as, CF13as and 1ul of each 10uM primer sets 10s, 11s, 10as,
   11as, 13as in one PCR tube.
9. Aliquot 19.7ul of the Master Mix to each tube.
10. In a PE2400 cycler,
    96C; 10 MIN
    40 CYCLES
    95C; 10 SEC
    55C; 30 SEC
    65C; 1 MIN
    40 CYCLES
    70C; 10 MIN
    4C; storage
11. After PCR, The amplified products were separated as described in the
    previous section. The results are shown in FIG. 7. Even in the
    multiplexed amplification each detection probe gives rise to a unique
    e-tag with distinct mobility.

Example 7

Electroseparation of Nine Electrophoretic Tags on Microfluidic Chip

Label conjugates comprising 9 different fluorescein derivatives linked to thymine, (Table 1 in Example 6; 1–9): Poly deoxy thymidine (20-mer; with a 5' thiol group) is reacted with different maleamide functionalized fluoresceins. After the reaction the product is ethanol precipitated. In a reaction of 12 µl in volume, 10 µl of 25 µM oligo, 1.0 µl 10×S1 nuclease reaction buffer, 1 µl of S1 nuclease, incubate at 37° C. for 30 min followed by 96° C. for 25 min. The digested fragments are purified by HPLC.

Figure 8:
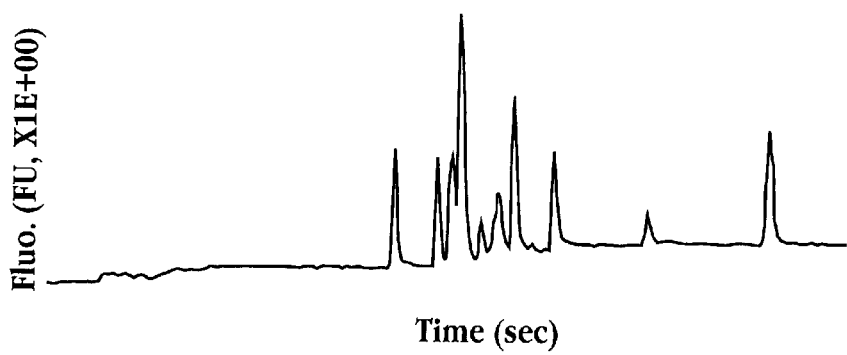
FIG. 8 is an electropherogram of a separation of 9 negatively charged e-tag probes.

The nine different e-tags prepared as described above and fluorescein were combined in an aqueous buffered and were separated and detected in an electrophoresis chip. Detection was 0.5 cm for the injection point on the anodal side of an electrophoresis channel. The results are shown in FIG. 8.

Example 8

RT-PCR Conditions:

Ten ul from a total volume of 25 uls of each mRNA was analyzed in a total volume of 50 uls containing 0.5 uM of each of the oligonucleotide primers, 0.2 mM of each dNTP, 100 nM of each e-tag labeled oligonucleotide probe, 1×RT PCR buffer, 2.5 mM MgCl2, 0.1 U/ul Tfl DNA polymerase and 0.1 U/ul AMV Reverse Transcriptase (Promega Access, RT-PCR system).

Reverse Transcription was performed for 45 minutes at 48° C. followed by PCR. (40 thermal cycles of 30 s at 94° C., 1 min at 60° C. and 2 min at 69° C. mRNA was obtained from M. Williams, Genentech Inc. Probe and primer design was performed as described in Analytical Biochemistry, 270, 41–49 (1999). Phosphorothioates were attached to 2, 3,4 and 5 phosphate moieties from the 5' end. Separation was performed as described in the previous section.

Figure 9A:
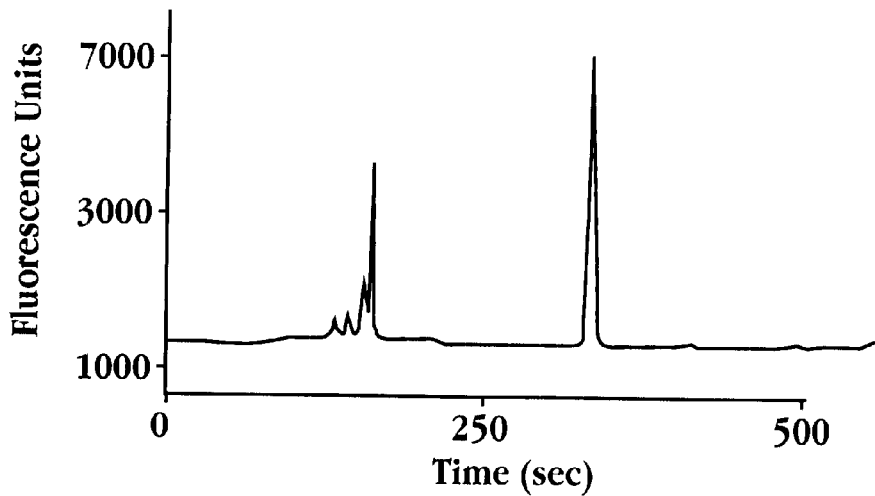
FIGS. 9A and 9B are electropherograms of probes employing a penultimate thiophosphate linkage in the e-tag probes to discourage cleavage after the first phosphate linkage.

FIG. 9a: Demonstrates the formation of 5 different cleavage products in the PCR amplification of ANF with electrophoretic tag labeled at the 5' end of the sequence detection probe. In the second experiment, phosphate group at 2,3,4 and 5 position is converted into thiophosphate group. PCR amplification of ANF using thiophospate modified sequence detection probe yield only one cleavage product.

Figure 9B:
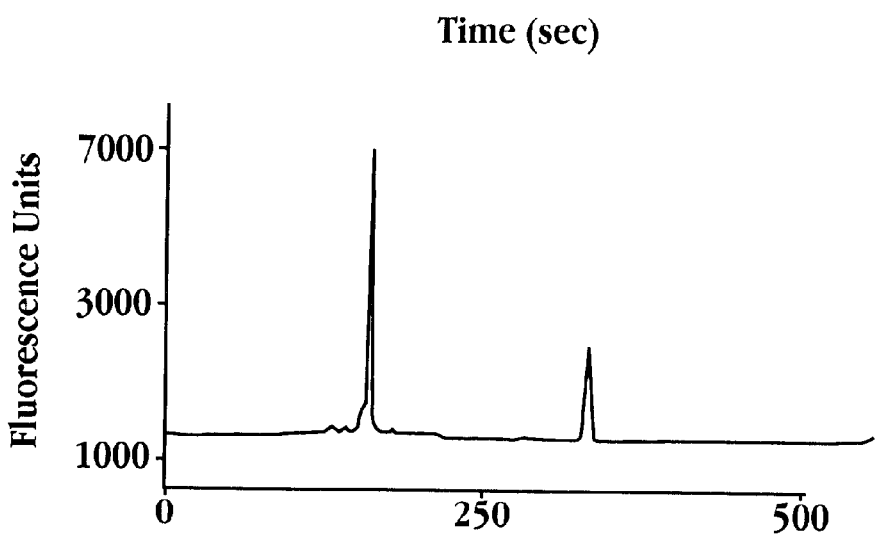
Figure 9C:
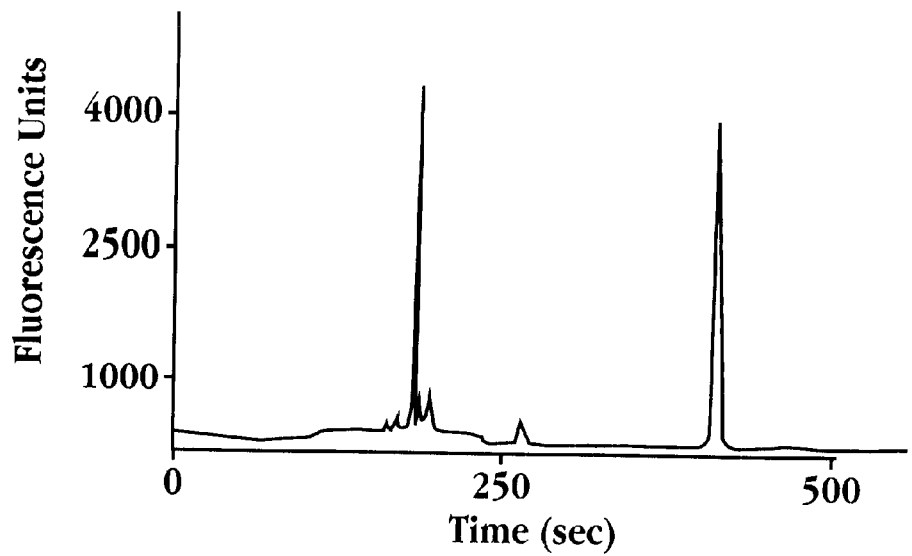
Figure 9D:
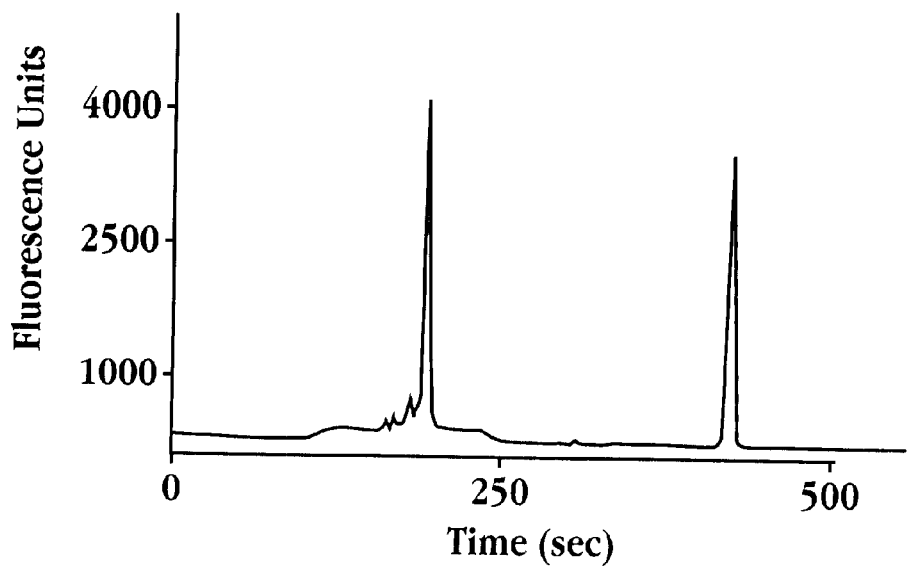

FIG. 9b Demonstrates the formation of 3 different cleavage products in the PCR amplification of GAPDH with e-tag labeled at the 5' end of the sequence detection probe. In the second experiment, phosphate group at 2 and 3 position is converted into thiophosphate group. PCR amplification of ANF using thiophospate modified sequence detection probe yield only one predominant cleavage product.

Results clearly demonstrate that for two different genes that thiophosphates prevent cleavage at multiple sites of detection probes.

A single detectable entity (a single electrophoretic tag: FIGS. 9a and 9b) is generated as a consequence of amplification reaction.

Example 9

General Procedure for Synthesis of 6-Carboxyfluorescein Phosphoramidite Derivatives To a solution of 6-carboxyfluorescein (0.5 g, 1.32 mmol) in dry pyridine (5 mL) was added dropwise, isobutyric anhydride (0.55 mL, 3.3 mmol). The reaction was allowed to stir at room temperature under an atmosphere of nitrogen for 3 h. After removal of pyridine in vacuo the residue was redissolved in ethyl acetate (150 mL) and washed with water (150 mL). The organic layer was separated, dried over Na$_2$SO$_4$, filtered, and concentrated in vacuo to yield a brownish residue. This material was dissolved in CH$_2$Cl$_2$ (5 mL) after which N-hydroxy succinimide (0.23 g, 2.0 mmol) and dicyclohexylcarbodiimide (0.41 g, 1.32 mmol) were added. The reaction was allowed to stir at room temperature for 3 h and then filtered through a fritted funnel to remove the white solid, which had formed. To the filtrate was added aminoethanol (0.12 mL, 2.0 mmol) dissolved in 1 mL of CH$_2$Cl$_2$. After 3 h the reaction was again filtered to remove a solid which had formed and then diluted with additional CH$_2$Cl$_2$ (50 mL). The solution was washed with water (150 mL) and then separated. The organic layer was dried over Na$_2$SO$_4$, filtered, and concentrated in vacuo to yield a white foam (0.7 g, 95%, 3 steps). $^1$H NMR: (DMSO) δ 8.68 (t, 1H), 8.21 (d, 1H), 8.14 (d, 1H), 7.83 (s, 1H), 7.31 (s, 2H), 6.95 (s, 4H), 4.69 (t, 1H), 3.45 (q, 2H), 3.25 (q, 2H), 2.84 (h, 2H), 1.25 (d, 12 H). Mass (LR FAB$^+$) calculated for $C_{31}H_{29}NO_9$ (M+H$^+$) 559.2, found: 560.

It is evident from the above results that the subject invention provides an accurate, efficient and sensitive process, as well as compositions for use in the process, to perform multiplexed reactions. The protocols provide for great flexibility in the manner in which determinations are carried out and maybe applied to a wide variety of situations involving hpatens, antigens, nucleic acids, cells, etc., where one may simultaneously perform a number of determinations on a single or plurality of samples and interrogate the samples for a plurality of events. The events may vary from differences in nucleic acid sequence to proteomics to enzyme activities. The results of the determination are readily read in a simple manner using electrophoresis or mass spectrometry. Systems are provided where the entire process, after addition of the sample and reagents, maybe performed under the control of a data processor with the results automatically recorded.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting at least one target nucleic acid sequence in a nucleic acid sample, said method comprising:

combining said nucleic acid sample and at least one reagent pair consisting of a primer and an e-tag linked by a cleavable bond to a target-binding sequence, where at least one nucleotide linkage at positions immediately 3' of the second nucleotide at the 5'-end of said target-binding sequence is resistant to nuclease hydrolysis, each reagent pair having a sequence homologous to each nucleic acid sequence to be determined, wherein each said primer specifically binds to said target nucleic acid and said target-binding sequence binds to said target nucleic acid downstream from said primer, wherein each said target-binding sequence is characterized by being linked to a non-oligomeric e-tag specific for each said nucleic acid sequence;

executing at least one cycle of cleavage of said cleavable bond, whereby said e-tag is released substantially free of said target-binding sequence, such that cleavage of the target-binding sequence at its 5' end produces a single released product comprised of the e tag and the 5'-end nucleotide of the target-binding sequence, wherein each said released product produced from a given target-binding sequence has a known, unique electrophoretic mobility with respect to the released products produced from all other such target-binding sequences, by virtue of a unique charge/mass ratio associated with the e tag;

separating released products into individual fractions of released products specific for each target nucleic acid sequence; and detecting said released product fractions, whereby the presence in said target nucleic acid sample of said at least one nucleic acid sequence is detected.

2. A method according to claim 1, wherein said combining further comprises a 5'-3'-exonuclease to achieve said cleavage.

3. A method according to claim 1, wherein said primer further comprises a cleavage reagent on said primer to achieve said cleavage.

4. A method according to claim 3, wherein said cleavage reagent is an enzyme that produces singlet oxygen or hydrogen peroxide and said cleavable bond is oxidatively cleaved.

5. A method according to claim 1 wherein at least one link in said nucleic acid sequence of said target-binding sequence is resistant to nuclease cleavage.

6. A method according to claim 1, wherein a ligand is bonded to said e-tag linked target binding sequence where upon release of said e-tag, said ligand is retained with the remaining portion of said target-binding sequence, and further including the step after said combining, binding said ligand with a receptor to diminish any interference in said separating from ligand containing components.

7. A method according to claim 1, wherein said at least one target nucleic acid sequence comprises a snp and said cleavage is achieved by a 5'-3' exonuclease, wherein either said target-binding sequence or said primer includes a nucleotide complementary to said snp.

* * * * *